US008092796B2

(12) United States Patent
Lee et al.

(10) Patent No.: US 8,092,796 B2
(45) Date of Patent: *Jan. 10, 2012

(54) MONOCLONAL ANTIBODIES AGAINST ANGPTL4

(75) Inventors: E-Chiang Lee, The Woodlands, TX (US); Gregory M. Landes, The Woodlands, TX (US); Kyu Chung, Granger, IN (US); Ling Chen, Blue Bell, PA (US); Urvi Desai, The Woodlands, TX (US); David Reed Powell, Houston, TX (US); Seokjoo Hong, The Woodlands, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/631,598

(22) Filed: Dec. 4, 2009

(65) Prior Publication Data

US 2011/0008359 A1    Jan. 13, 2011

Related U.S. Application Data

(63) Continuation of application No. 11/327,844, filed on Jan. 6, 2006, now Pat. No. 7,655,762.

(60) Provisional application No. 60/642,022, filed on Jan. 7, 2005.

(51) Int. Cl.
C07K 16/18 (2006.01)
A61K 39/395 (2006.01)

(52) U.S. Cl. ............ 424/130.1; 530/387.9; 530/388.1; 424/139.1; 424/141.1; 424/142.1; 424/133.1

(58) Field of Classification Search .................. None
See application file for complete search history.

(56) References Cited

U.S. PATENT DOCUMENTS

| 7,371,384 B2 | 5/2008 | Gerber et al. |
| 2004/0138430 A1 | 7/2004 | Zhongchao et al. |

FOREIGN PATENT DOCUMENTS

| CN | 1312294 A | 9/2001 |
| WO | WO 99/67382 A2 | 12/1999 |
| WO | WO 01/77151 A2 | 10/2001 |
| WO | WO 03/010205 A1 | 2/2003 |
| WO | WO 2006/014678 A2 | 2/2006 |
| WO | WO 2006/014729 A2 | 2/2006 |

OTHER PUBLICATIONS

Granlund et al., Impaired lipid accumulation by trans 10, cis 12 CLA during adipocyte differentiation is dependent on timing and length of treatment, Biochim. Biophys. Acta 1687: 11-22 (2005).
Inoue et al., Increased expression of PPAR-gamma in high fat diet-induced liver steatosis in mice, Biochem. Biophys. Res. Comm. 336: 215-222 (2005).
Sonnenburg et al., "Glycosylphosphatidylinositol-anchored HDL binding protein stabilizes lipoprotein lipase and prevents its inhibition by angiopoietin-like 3 and angiopoietin-like 4," *J. Lipid Res.*, 50:2421-2429 (2009).
Janeway et al., *Immunobiology*, section 3-5, pp. 3:7 to 3:9 (Current Biology Ltd./Garland Publishing Inc. 1994).
Romeo et al., "Population-based resequencing of *ANGPTL4* uncovers variations that reduce triglycerides and increase HDL," *Nature Genetics*, 39: 513-516 (2007).
Desai et al., "Lipid-lowering effects of anti-angiopoietin-like 4 antibody recapitulate the lipid phenotype found in angiopoietin-like 4 knockout mice," *Proc. Natl. Acad. Sci.*, 104:11766-11771 (2007).
Li, "Genetics and regulation of angiopoietin-like proteins 3 and 4," *Curr. Opin. Lipidol.* 17: 152-156 (2006).
Sukonina et al., "Angiopoietin-like protein 4 converts lipoprotein lipase to inactive monomers and modulates lipase activity in adipose tissue," *Proc. Natl. Acad. Sci.*, 103:17450-17455 (2006).
Yoshida et al., "Angiopoietin-like protein 4 is a potent hyperlipidemia-inducing factor in mice and inhibitor of lipoprotein lipase," *J. Lipid Res.*, 43:1770-1772 (2002).
Ando et al., "A decreased expression of angiopoietin-like 3 is protective against atherosclerosis in apoE-deficient mice," *J. Lipid Res.*, 44:1216-1223 (2003).
Chait et al., "Chylomicronemia syndrome," *Adv. Intern. Med.*, 37:249-273 (1992).
Ge et al., "Oligomerization and regulated proteolytic processing of angiopoietin-like protein 4," *J. Biol. Chem.*, 279:2038-2045 (2004).
Ge et al., "Oligomerization state-dependent hyperlipidemic effect of angiopoietin-like protein 4," *J. Lipid Res.*, 45:2071-2079 (2004).
Ge et al., "Differential regulation and properties of angiopoietin-like proteins 3 and 4," *J. Lipid Res.*, 46:1484-1490 (2005).
Hermann et al., "Angiopoietin-like-4 is a potential angiogenic mediator in arthritis," *Clinical Immunology*, 115:93-101 (2005).
Kersten et al., "Characterization of the fasting-induced adipose factor FIAF, a novel peroxisome proliferator-activated receptor target gene," *J. Biol. Chem.*, 275:28488-28493 (2000).
Kersten, "Regulation of lipid metabolism via angiopoietin-like proteins," *Biochemical Society Transactions*, 33:1059-1062 (2005).
Kim et al., "Hepatic expression, synthesis and secretion of a novel fibrinogen/angiopoietin-related protein that prevents endothelial-cell apoptosis," *Biochem. J.*, 346:603-610 (2000).
Koishi et al., "*Angptl3* regulates lipid metabolism in mice," *Nature Genetics*, 30:151-157 (2002).
Korstanje et al., "Locating *AthB*, a locus for murine atherosclerosis susceptibility and testing several of its candidate genes in mice and humans," *Atherosclerosis*, 177:443-450 (2004).
Köster et al., "Transgenic Angptl4 overexpression and targeted disruption of Angptl4 and Angptl3: regulation of triglyceride metabolism," *Endocrinology*, Published online Aug. 4, 2005, as doi:10.1210/en.2005-0476.
Kratky et al., "Endothelial lipase provides an alternative pathway for FFA uptake in lipoprotein lipase-deficient mouse adipose tissue," *J. Clin. Invest.*, 115:161-167 (2005).
Mandard et al., "The direct peroxisome proliferator-activated receptor target fasting-induced adipose factor (FIAF/PGAR/ANGPTL4) is present in blood plasma as a truncated protein that is increased by fenofibrate treatment," *J. Biol. Chem.*, 279:34411-34420 (2004).

(Continued)

*Primary Examiner* — Marianne P Allen
(74) *Attorney, Agent, or Firm* — Andrus, Sceales, Starke & Sawall, LLP

(57) ABSTRACT

Monoclonal antibodies that specifically bind to ANGPTL4 are provided. Monoclonal antibodies that neutralize at least one activity of ANGPTL4 are provided. Methods of treating a disorder of lipid metabolism using neutralizing monoclonal antibodies are provided.

18 Claims, 43 Drawing Sheets

OTHER PUBLICATIONS

Mandard et al., "The fasting-induced adipose factor/angiopoietin-like protein 4 is physically associated with lipoproteins and governs plasma lipid levels and adiposity," *JBC Papers in Press*, published Nov. 4, 2005, www-jbc.org/cqi/doi/m1074/jbc.M506519200.

Moller, "New drug targets for type 2 diabetes and the metabolic syndrome," *Nature*, 414:821-827 (2001).

Nishimura et at, "Effects of NO-1886 (Ibrolipim), a lipoprotein lipase-promoting agent, on gene induction of cytochrome P450s, carboxylesterases, and sulfotransferases in primary cultures of human hepatocytes," *Drug Meta. Phannacokinet.*, 19:422-429 (2004).

Oike et al., "Angiopoietin-like proteins: potential new targets for metabolic syndrome therapy," Trends in *Molecular Medicine*, Article in Press (2005) doi:10.1 016/j.molmed.2005.08.002.

Schuetz et al., "Molecular classification of renal tumors by gene expression profiling," *J. Mol. Diagn.*, 7:206-218 (2005).

Sharkey et al., "Novel antiangiogenic agents for use in contraception," *Contraception*, 71 :263-271 (2005).

Shimizugawa et at, "ANGPTL3 decreases very low density lipoprotein triglyceride clearance by inhibition of lipoprotein lipase," *J. Biol. Chem.*, 277:33742-33746 (2002).

Weinstock et al., "Severe hypertriglyceridemia, reduced high density lipoprotein, and neonatal death in lipoprotein lipase knockout mice," *J Clin Invest.*, 96:2555-2568 (1995).

Yin et at, "Lipoprotein lipase activator NO-1886," *Cardiovascular Drug Reviews*, 21:133-142 (2003).

Yu et at, "Inhibition of cardiac lipoprotein utilization by transgenic overexpression of Angptl4 in the heart," *PNAS*, 102:1767-1772 (2005).

International Nonproprietary Names for Pharmaceuticals Substances (INN), *WHO Drug Infonnation*, 17:267-286 (2003).

FIG. 9
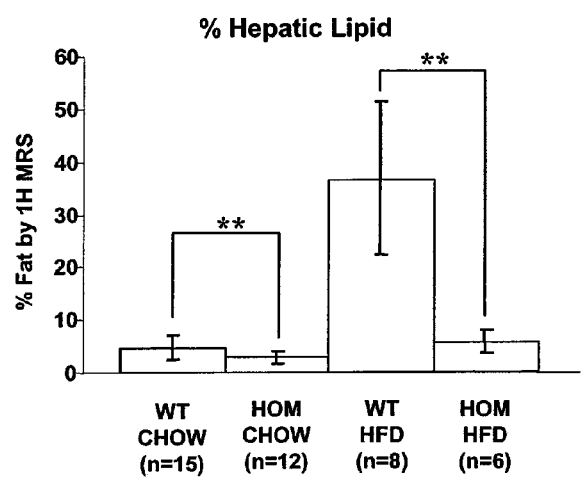
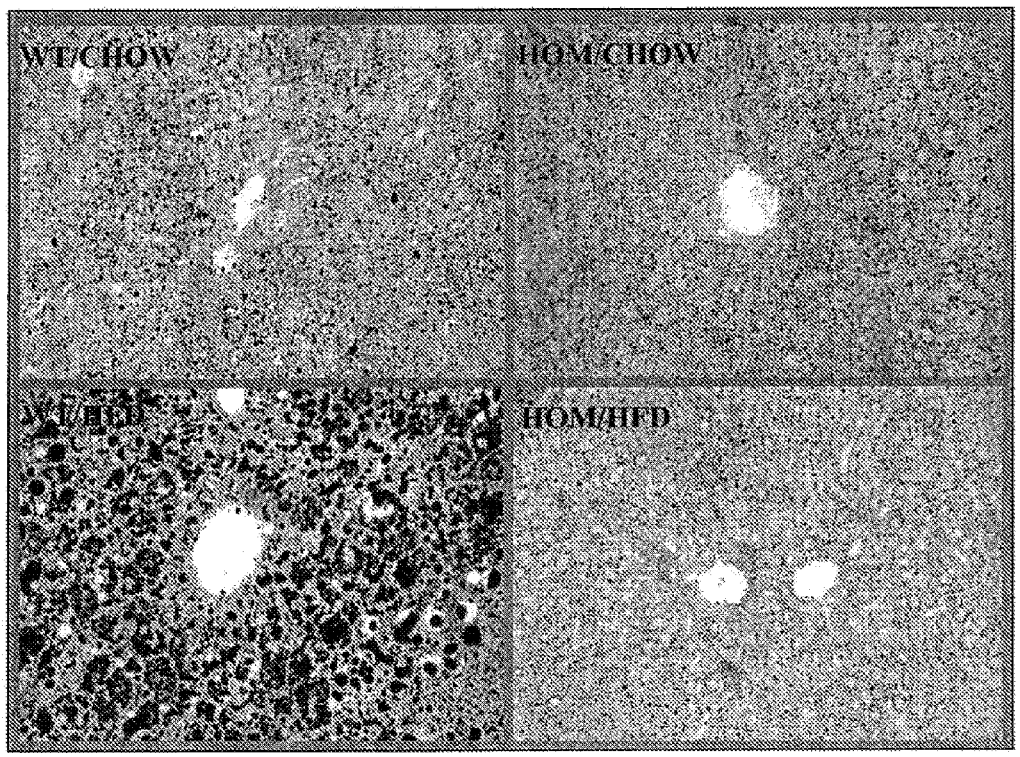

DIO Mice: Plasma Triglycerides after 5-Week mAb Injection
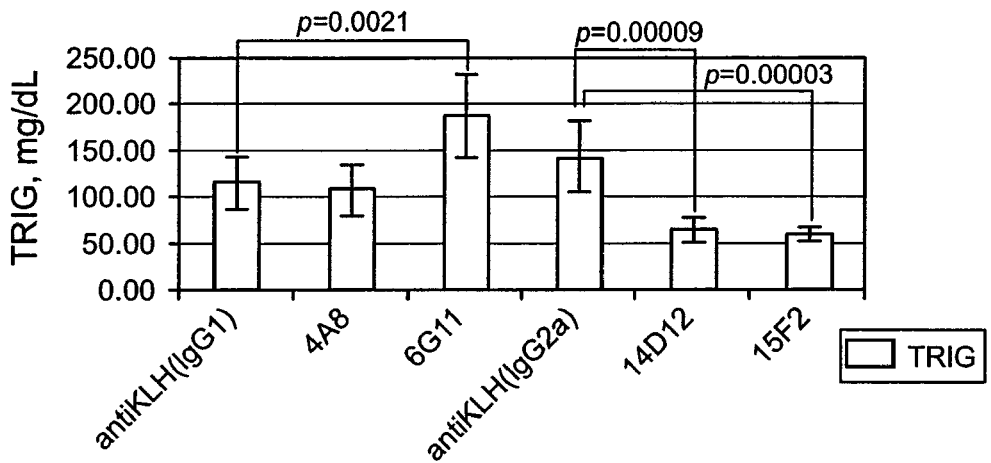
| % Increased (antiKLH) - 6G11 | 60.94 |
|---|---|
| % Decreased (antiKLH) - 14D12 | 53.22 |
| % Decreased (antiKLH) - 15F2 | 56.61 |
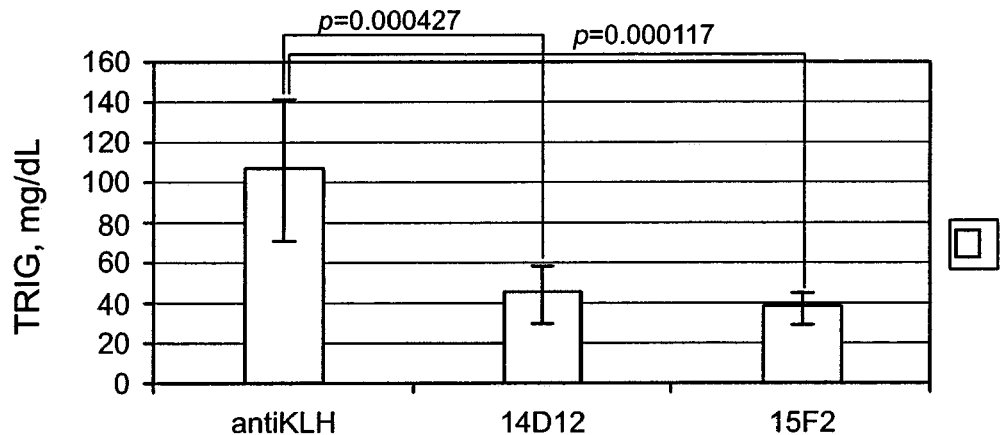
| % Decreased (antiKLH) - 14D12 | 59.35545 |
|---|---|
| % Decreased (antiKLH) - 15F2 | 64.45498 |
FIG. 22

DIO Mice: Plasma Cholesterol after 5-Week mAb Injection
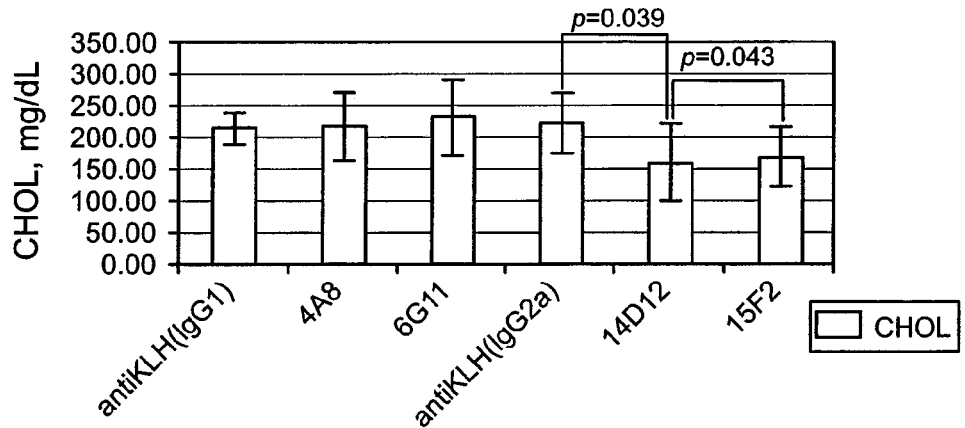
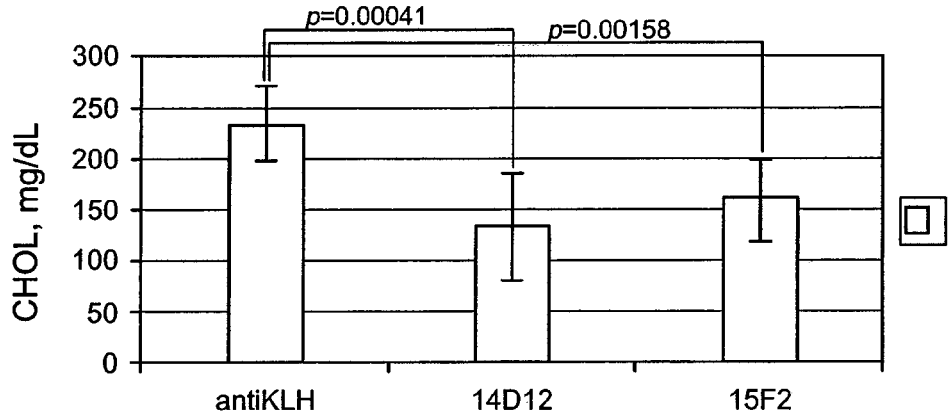
FIG. 23

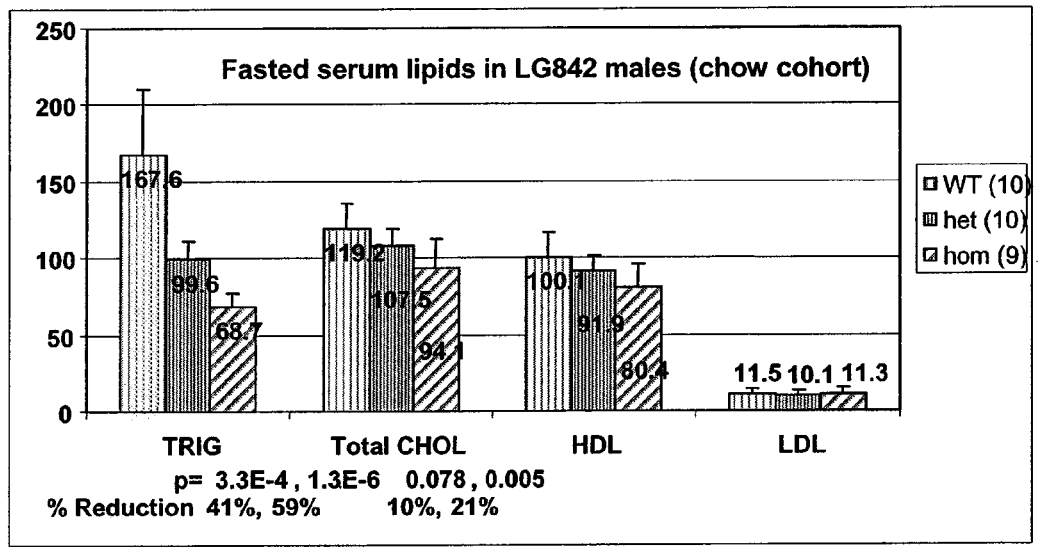
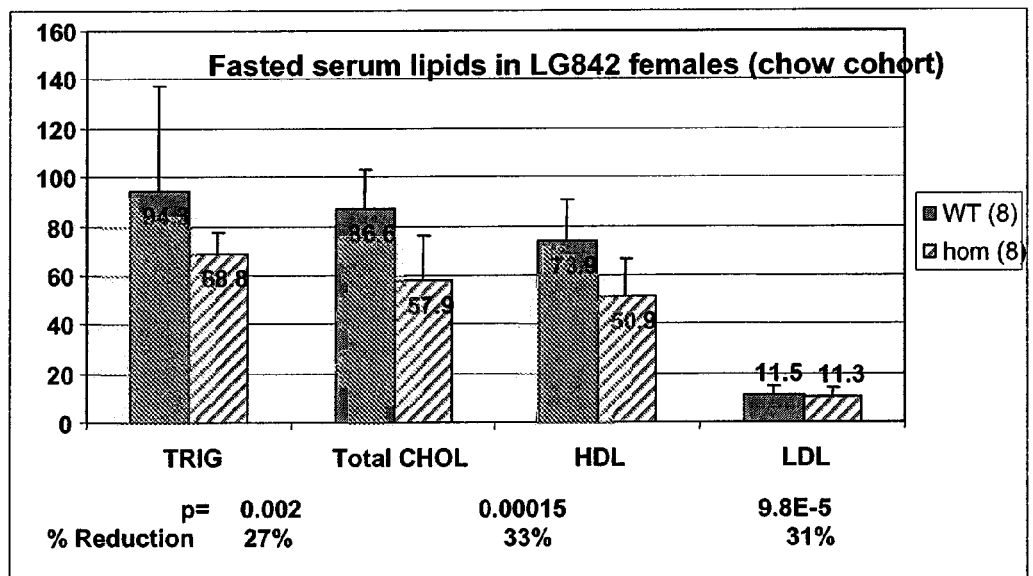
FIG. 25

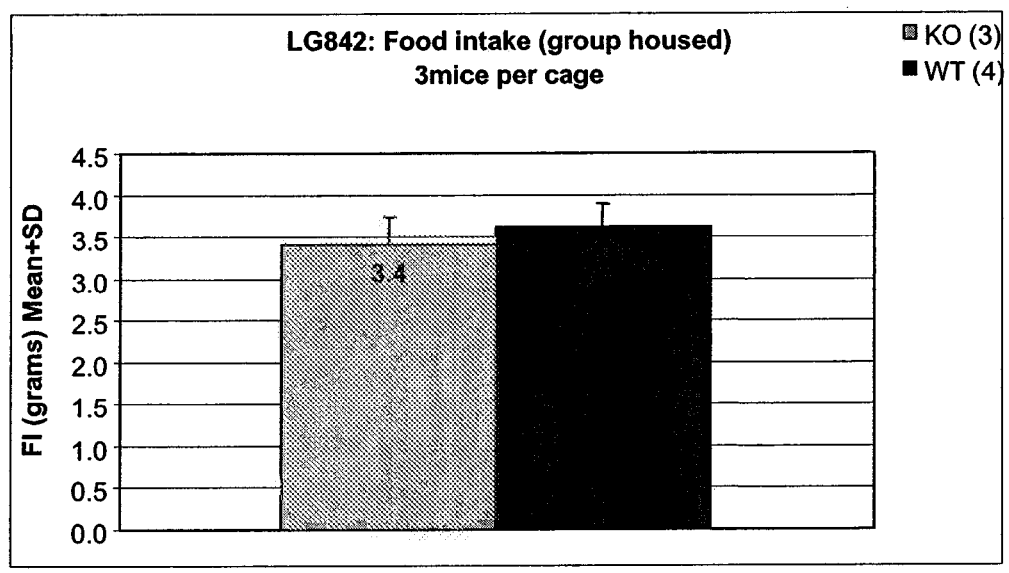
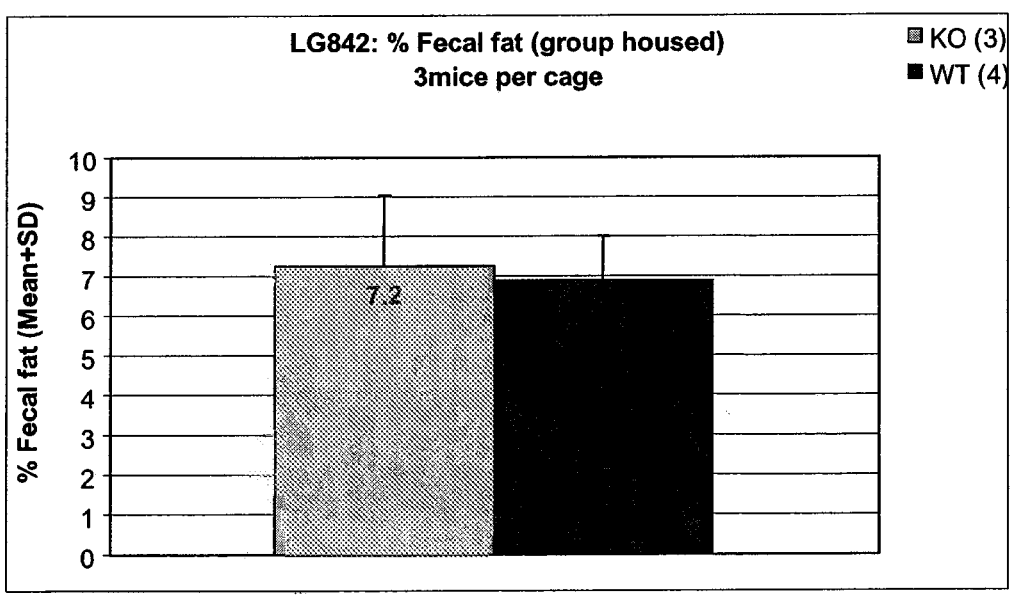
FIG. 28

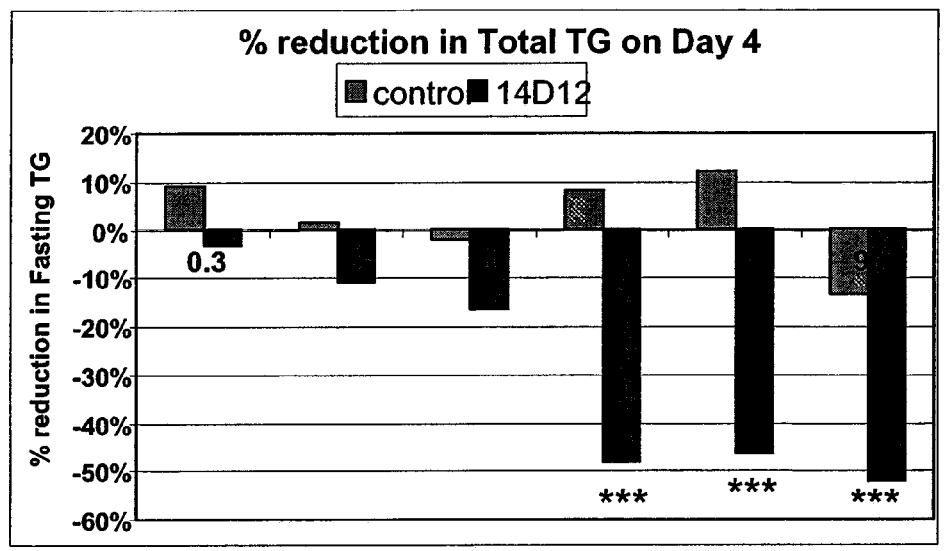
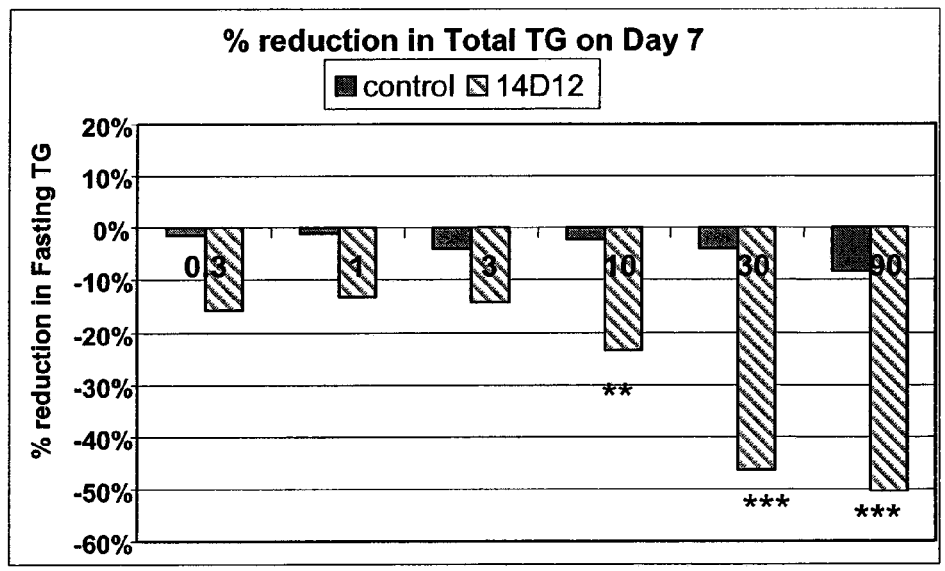
FIG. 34

FIG. 47

|        | 14D12 VH | 15F2 VH | 90B4 VH |
|--------|----------|---------|---------|
| 14D12 VH | 100    | 99      | 40      |
| 15F2 VH  |        | 100     | 40      |
| 90B4 VH  |        |         | 100     |

14D12 VH  SEQ ID NO: 12
15F2 VH   SEQ ID NO: 13
90B4 VH   SEQ ID NO: 14
Consensus SEQ ID NO: 15

FIG. 48

|  | FR1 | | CDR1 | | FR2 | | CDR2 | |
|---|---|---|---|---|---|---|---|---|
|  | 1 | 10 | 20 | 30 | 40 | 50 | 60 | 70 | 84 |

```
              1         10        20        30        40        50        60        70        84
14D12 VK  (1) --MVSTSQLLGELLFWTSMSRCEIVMTQSPATLSVTPGDRVSLSCRASQSIGDYLHWYQQKSHESPRLLIKYASQSISGIPSRF   SEQ ID NO: 16
15F2 VK   (1) MDMRAPAQFLGILLLWFPGARCEIQMTQSPSSMSASLGDRITITCQATQDIVKNLNWYQQKPGKPPSFLIHYATELAEGVPSRF   SEQ ID NO: 17
90B4 VK   (1) MDMRAPAQFLGILLLWFPGARCEIQMTQSPSSMSASLGDRITITCQATQDIVKNLNWYQQKPGKPPSFLIHYATELAEGVPSRF   SEQ ID NO: 18
Consensus (1) MDMRAPAQFLGILLLWFPGARCEIQMTQSPSSMSASLGDRITITCQATQDIVKNLNWYQQKPGKPPSFLIHYATELAEGVPSRF   SEQ ID NO: 19
```

|  | FR3 | | | CDR3 | | FR4 | |
|---|---|---|---|---|---|---|---|
|  | 85 | 90 | 100 | 110 | 120 | 130 |

```
              85        90        100       110       120       130
14D12 VK (85) SGSGSGSDFTLSIDSVEPEDVGVYYCQNGHSFPFTFGSGTKLEINR
15F2 VK  (83) SGSGSGSDYSLTISNLESEDFADYYCLQSYDFHYTFGGGTKLEINR
90B4 VK  (85) SGSGSGSDYSLTISNLESEDFADYYCLQSYDFHYTFGGGTKLEIN-
Consensus(85) SGSGSGSDYSLTISNLESEDFADYYCLQSYDFHYTFGGGTKLEINR
```

|  | 14D12 VK | 15F2 VK | 90B4 VK |
|---|---|---|---|
| 14D12 VK | 100 | 52 | 51 |
| 15F2 VK | 52 | 100 | 99 |
| 90B4 VK | 51 | 99 | 100 |

MONOCLONAL ANTIBODIES AGAINST ANGPTL4

This application is a continuation of U.S. application Ser. No. 11/327,844, filed Jan. 6, 2006, now U.S. Pat. No. 7,655,762, which claims the benefit of U.S. Provisional Application No. 60/642,022, filed Jan. 7, 2005, which are incorporated by reference herein for any purpose.

I. TECHNICAL FIELD

Monoclonal antibodies that specifically bind to angiopoietin-like protein 4 (ANGPTL4) are provided. Methods of using monoclonal antibodies that specifically bind to angiopoietin-like protein 4 (ANGPTL4) are provided. Pharmaceutical compositions comprising monoclonal antibodies that specifically bind to angiopoietin-like protein 4 (ANGPTL4) are provided.

II. INTRODUCTION

Angiopoeitin-like protein 4 is conserved among several mammalian species. Ge et al. (2004) *J. Biol. Chem.* 279: 2038-2045. Angiopoeitin-like protein 4 contains an N-terminal coiled-coil domain and a C-terminal fibrinogen-like domain. Kim et al. (2000) *Biochem. J.* 346:603-610. The N-terminal coiled-coil domain mediates oligomerization of angiopoeitin-like protein 4. Ge et al. (2004) *J. Biol. Chem.* 279:2038-2045. Oligomerized angiopoeitin-like protein 4 undergoes proteolytic processing in vivo, resulting in the cleavage of the fibrinogen-like domain. Ge et al. (2004) *J. Biol. Chem.* 279:2038-2045.

III. SUMMARY

In certain embodiments, a monoclonal antibody that specifically binds to ANGPTL4 and neutralizes at least one activity of ANGPTL4 is provided. In certain embodiments, the monoclonal antibody is a mouse monoclonal antibody. In certain embodiments, the monoclonal antibody is a humanized monoclonal antibody. In certain embodiments, the monoclonal antibody is a human monoclonal antibody. In certain embodiments, the monoclonal antibody increases LPL activity. In certain embodiments, the monoclonal antibody decreases the level of at least one serum lipid in vivo.

In certain embodiments, the monoclonal antibody binds to an epitope within a region of SEQ ID NO: 1 or SEQ ID NO: 50 from residue 21 to residue 174. In certain embodiments, the monoclonal antibody binds to an epitope within a region of SEQ ID NO:2 from residue 21 to residue 169. In certain embodiments, the monoclonal antibody is 14D12. In certain embodiments, the monoclonal antibody is 15F2. In certain embodiments, the monoclonal antibody is 90B4. In certain embodiments, the monoclonal antibody specifically binds to the same epitope as 14D12. In certain embodiments, the monoclonal antibody specifically binds to the same epitope as 15F2. In certain embodiments, the monoclonal antibody specifically binds to the same epitope as 90B4.

In certain embodiments, an antibody is provided that specifically binds to ANGPTL4 comprising a heavy chain and a light chain, wherein the heavy chain comprises an amino acid sequence as set forth in any one of SEQ ID NOs: 12 to 14; at least one CDR comprising an amino acid sequence as set forth in any one of SEQ ID NOs: 21, 39, and 20; or at least one CDR comprising an amino acid sequence as set forth in any one of SEQ ID NOs: 27 to 29; wherein the antibody neutralizes at least one activity of ANGPTL4. In certain embodiments, an antibody is provided that specifically binds to ANGPTL4 comprising a light chain, wherein the light chain comprises an amino acid sequence as set forth in any one of SEQ ID NOs: 16 to 18; at least one CDR comprising an amino acid sequence as set forth in any one of SEQ ID NOs: 30 to 32; or at least one CDR comprising an amino acid sequence as set forth in any one of SEQ ID NOs: 33 to 35, wherein the antibody neutralizes at least one activity of ANGPTL4.

In certain embodiments, an antibody comprising a heavy chain that comprises an amino acid sequence as set forth in any one of SEQ ID NOs: 12 to 14 is provided. In certain embodiments, an antibody comprising a heavy chain that comprises at least one CDR comprising an amino acid sequence as set forth in any one of SEQ ID NOs: 21, 39, and 20 is provided. In certain embodiments, an antibody comprising a heavy chain that comprises at least one CDR comprising an amino acid sequence as set forth in any one of SEQ ID NOs: 27 to 29 is provided. In certain embodiments, an antibody comprising a light chain that comprises an amino acid sequence as set forth in any one of SEQ ID NOs: 16 to 18 is provided. In certain embodiments, an antibody comprising a light chain that comprises at least one CDR comprising an amino acid sequence as set forth in any one of SEQ. ID NOs: 30 to 32 is provided. In certain embodiments, an antibody comprising a light chain that comprises at least one CDR comprising an amino acid sequence as set forth in any one of SEQ ID NOs: 33 to 35 is provided.

In certain embodiments, an antibody comprises a heavy chain that comprises an amino acid sequence as set forth in SEQ ID NO: 12. In certain embodiments, an antibody comprises a heavy chain that comprises an amino acid sequence as set forth in SEQ ID NO: 13. In certain embodiments, an antibody comprises a heavy chain that comprises an amino acid sequence as set forth in SEQ ID NO: 14.

In certain embodiments, an antibody comprises a light chain that comprises an amino acid sequence as set forth in SEQ ID NO: 16. In certain embodiments, an antibody comprises a light chain that comprises an amino acid sequence as set forth in SEQ ID NO: 17. In certain embodiments, an antibody comprises a light chain that comprises an amino acid sequence as set forth in SEQ ID NO: 18.

In certain embodiments, an antibody comprising a heavy chain comprising a CDR1 as set forth in SEQ ID NO: 21, a CDR2 as set forth in SEQ ID NO: 39, and a CDR3 as set forth in SEQ ID NO: 20 is provided. In certain embodiments, the X is SEQ ID NO: 20 is any amino acid. In certain embodiments, the X is SEQ ID NO: 20 is a hydrophobic amino acid. In certain embodiments, the X is SEQ ID NO: 20 is glycine, leucine, isoleucine, valine, or alanine. In certain embodiments, the X is SEQ ID NO: 20 is valine or isoleucine. In certain embodiments, the X is SEQ ID NO: 20 is valine or isoleucine. In certain embodiments, the X in SEQ ID NO: 39 is any amino acid. In certain embodiments, the X in SEQ ID NO: 39 is glycine, aspartate, or tyrosine. In certain embodiments, an antibody comprising a heavy chain comprising a CDR1 as set forth in SEQ ID NO: 27, a CDR2 as set forth in SEQ ID NO: 28, and a CDR3 as set forth in SEQ ID NO: 29 is provided.

In certain embodiments, an antibody comprising a light chain comprising a CDR1 as set forth in SEQ ID NO: 30, a CDR2 as set forth in SEQ ID NO: 31, and a CDR3 as set forth in SEQ ID NO: 32 is provided. In certain embodiments, an antibody comprising a light chain comprising a CDR1 as set forth in SEQ ID NO: 33, a CDR2 as set forth in SEQ ID NO: 34, and a CDR3 as set forth in SEQ ID NO: 35 is provided.

In certain embodiments, an antibody is an antibody fragment. In certain embodiments, an is a scFv fragment. In certain embodiments, an antibody is a Fab fragment. In certain embodiments, an antibody is a F(ab')$_2$ fragment. In certain embodiments, an antibody is a Fab' fragment.

In certain embodiments, an antibody against ANGPTL4 binds to a peptide having the amino acid sequence of SEQ ID NO: 40. In certain embodiments, an antibody against ANGPTL4 binds to a peptide having the amino acid sequence of SEQ ID NO: 41. In certain embodiments, an antibody against ANGPTL4 binds to a peptide having the amino acid sequence of SEQ ID NO: 43. In certain embodiments, an antibody against ANGPTL4 binds to a peptide having the amino acid sequence of SEQ ID NO: 41 and binds to a peptide having the amino acid sequence of SEQ ID NO: 43.

In certain embodiments, a pharmaceutical composition comprising a monoclonal antibody that specifically binds to ANGPTL4 and neutralizes at least one activity of ANGPTL4 is provided. In certain embodiments, a method of treating a disorder of lipid metabolism is provided, wherein the method comprises administering to a patient an effective amount of the pharmaceutical composition. In certain embodiments, a method of decreasing the level of one or more serum lipids is provided, wherein the method comprises administering to a patient an effective amount of the pharmaceutical composition. In certain embodiments, a method of treating hypertriglyceridemia is provided, wherein the method comprises administering to a patient an effective amount of the pharmaceutical composition. In certain embodiments, a method of treating hypercholesterolemia is provided, wherein the method comprises administering to a patient an effective amount of the pharmaceutical composition. In certain embodiments, a method of treating obesity is provided, wherein the method comprises administering to a patient an effective amount of the pharmaceutical composition. In certain embodiments, a method of treating diabetes is provided, wherein the method comprises administering to a patient an effective amount of the pharmaceutical composition.

IV. BRIEF DESCRIPTION OF THE FIGURES

FIG. 9A shows lipid levels in the livers from wild-type (WT) mice and Angptl4 knockout (HOM) mice fed a standard ("chow") diet or a high fat diet (HFD). FIG. 9B shows histochemical staining of liver sections from wild-type (WT) mice and Angptl4 knockout (HOM) mice fed a standard ("chow") diet or a high fat diet (HFD), as described in Example E.

Figure 11:
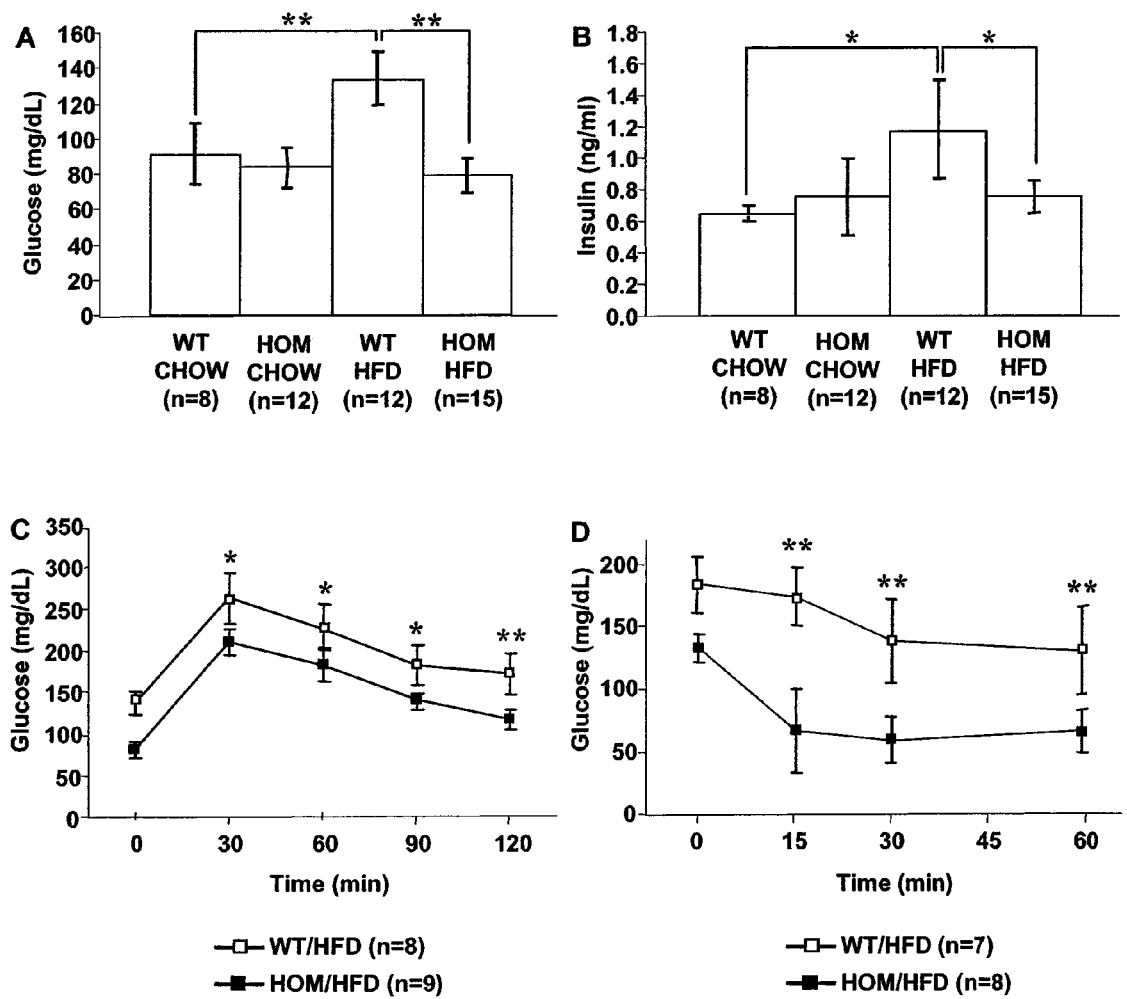

FIG. 11, panels A and B, show glucose and insulin levels in wild-type (WT) and Angptl4 knockout (HOM) mice fed a standard ("chow") diet or high fat diet (HFD), as described in Example F. Panels C and D show glucose and insulin tolerance in wild-type (WT) and Angptl4 knockout (HOM) mice fed a high fat diet (HFD).

Figure 12:
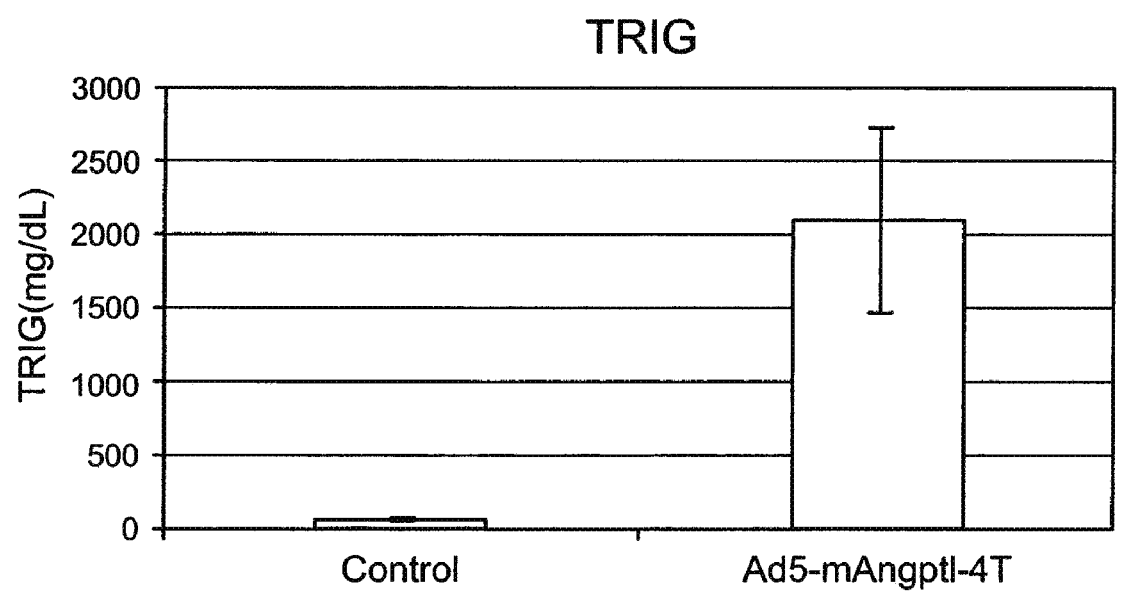

FIG. 12 shows fasted serum triglyceride levels in Angptl4 knockout mice three days after injection with an adenovirus construct (Ad5-mAngptl-4T) expressing full-length mouse ANGPTL4, as described in Example G.

Figure 13:
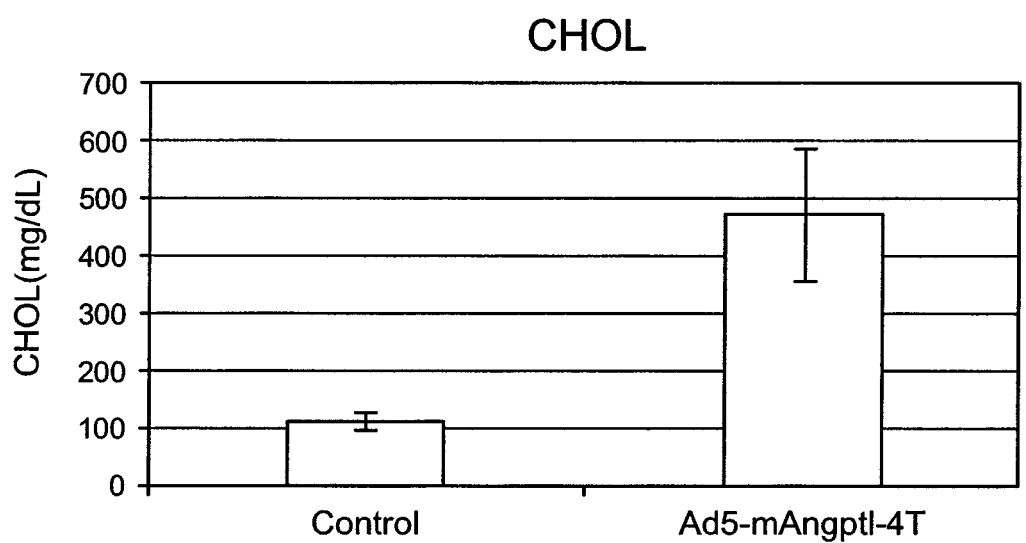

FIG. 13 shows fasted serum cholesterol levels in Angptl4 knockout mice three days after injection with an adenovirus construct (Ad5-mAngptl-4T) expressing full-length mouse ANGPTL4, as described in Example G.

Figure 14:
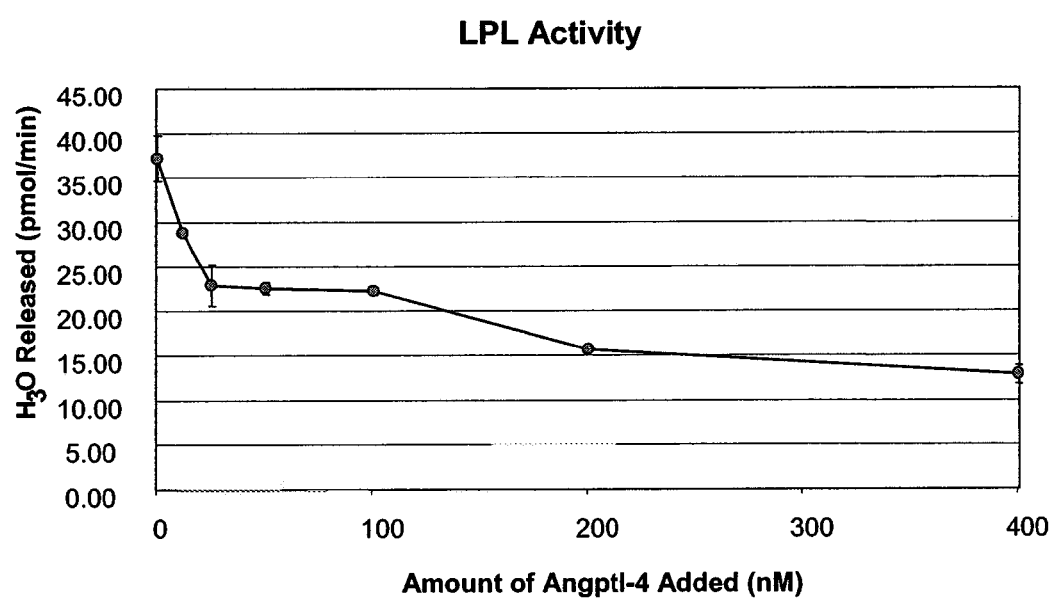

FIG. 14 shows the activity of lipoprotein lipase (LPL) in vitro in the presence of increasing amounts of full-length mouse ANGPTL4, as described in Example I.

Figure 15:
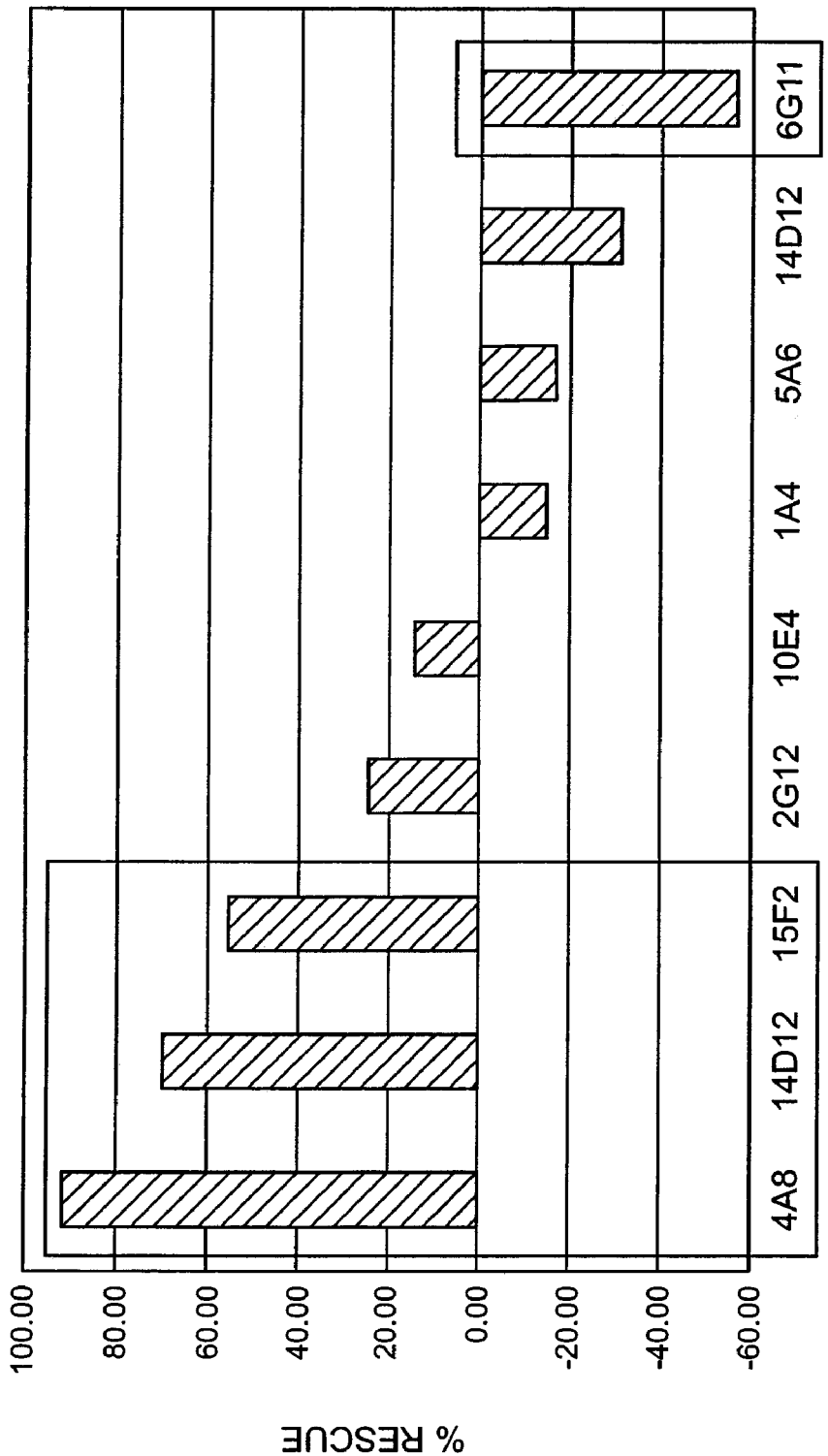

FIG. 15 shows certain neutralizing monoclonal antibodies against mouse ANGPTL4 (4A8, 14D12, and 15F2) that rescued LPL activity from inhibition by ANGPTL4 in vitro, as described in Example L.

Figure 16:
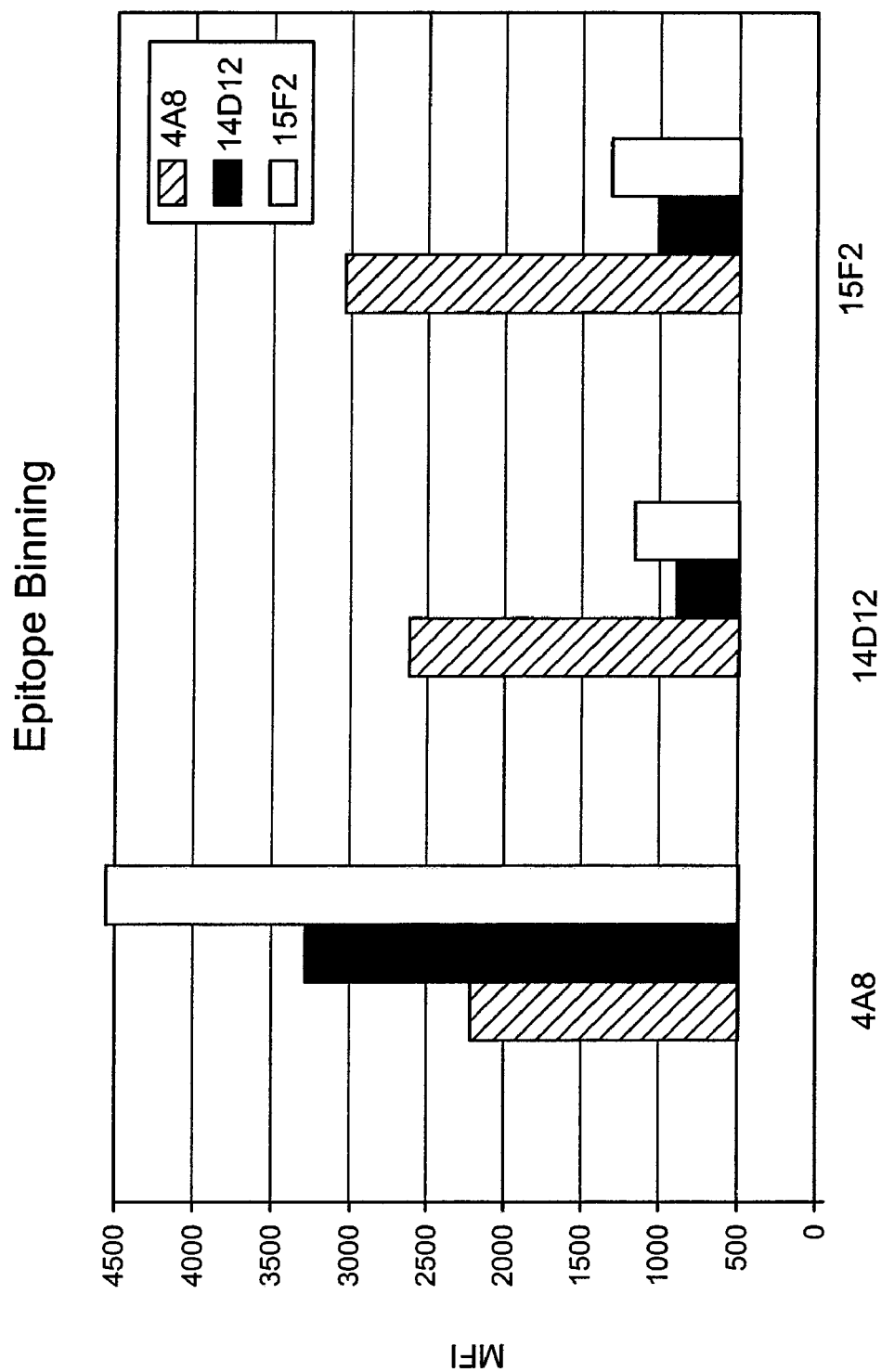

FIG. 16 shows the results of epitope binning experiments for monoclonal antibodies 4A8, 14D12, and 15F2, as described in Example 0.

Figure 17:
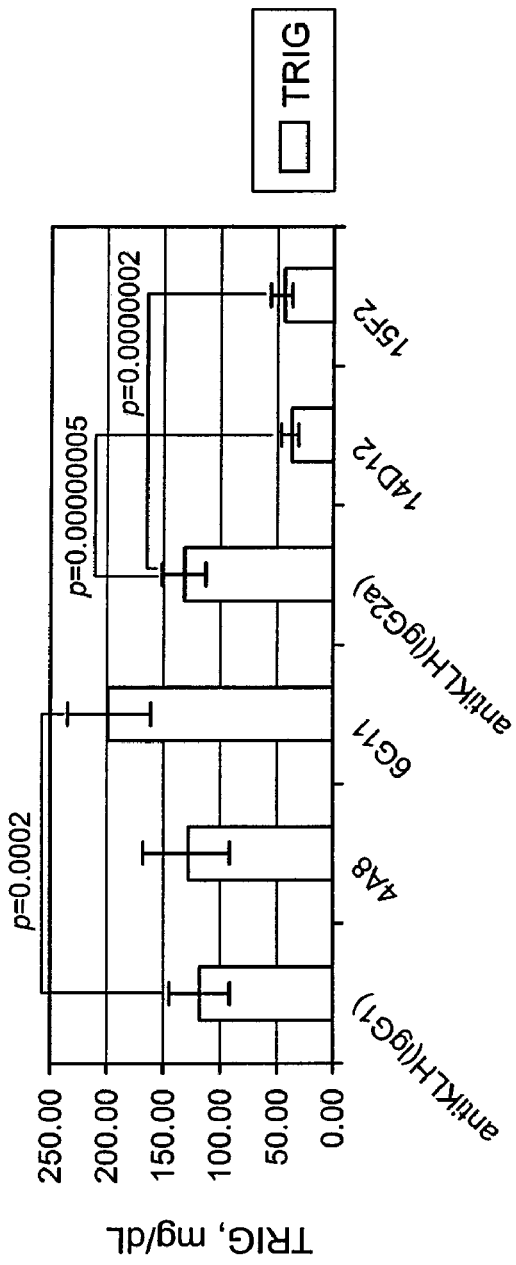

FIG. 17 shows fasted serum triglyceride levels in wild-type mice fed a standard diet four days after injection of monoclonal antibodies against mouse ANGPTL4, as described in Example P.

Figure 18:
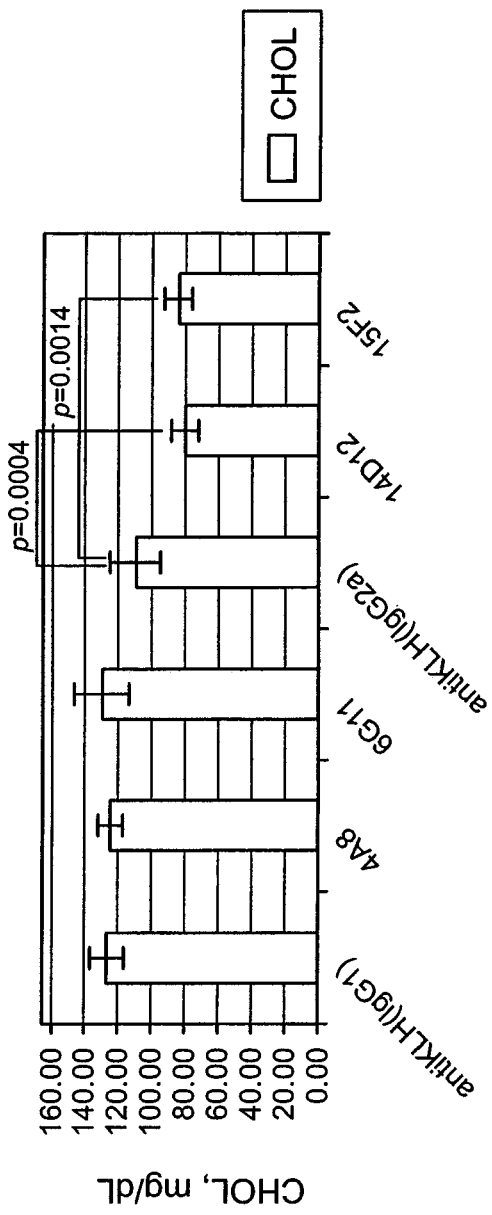

FIG. 18 shows fasted serum cholesterol levels in wild-type mice fed a standard diet four days after injection of monoclonal antibodies against mouse ANGPTL4, as described in Example P.

Figure 19:
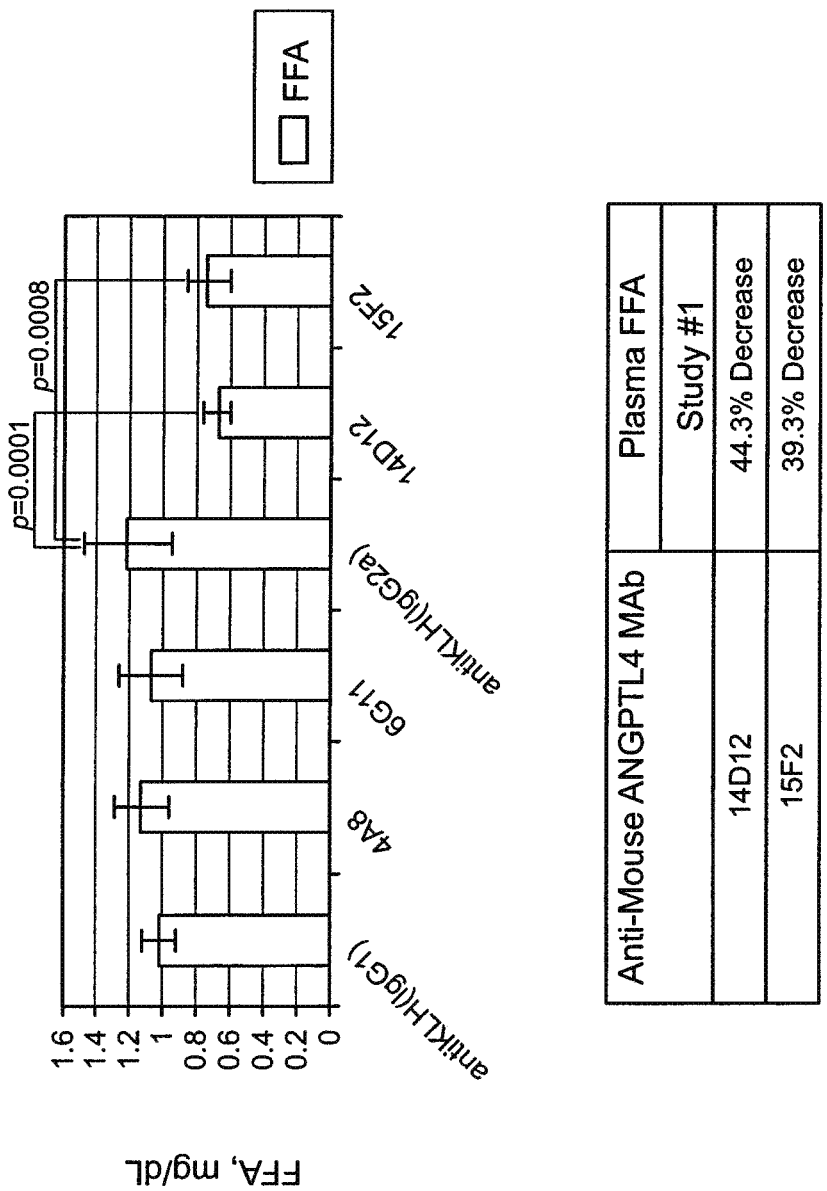

FIG. 19 shows fasted serum free fatty acid (FFA) levels in wild-type mice fed a standard diet four days after injection of monoclonal antibodies against mouse ANGPTL4, as described in Example P.

Figure 20:
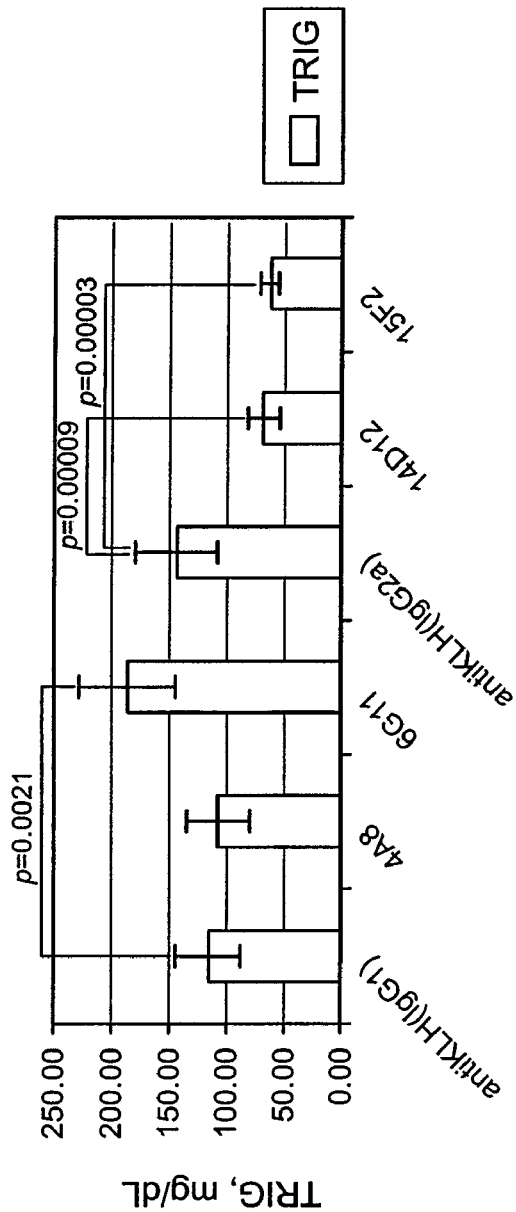

FIG. 20 shows fasted serum triglyceride levels in wild-type mice fed a high fat diet four days after injection of monoclonal antibodies against mouse ANGPTL4, as described in Example P.

Figure 21:
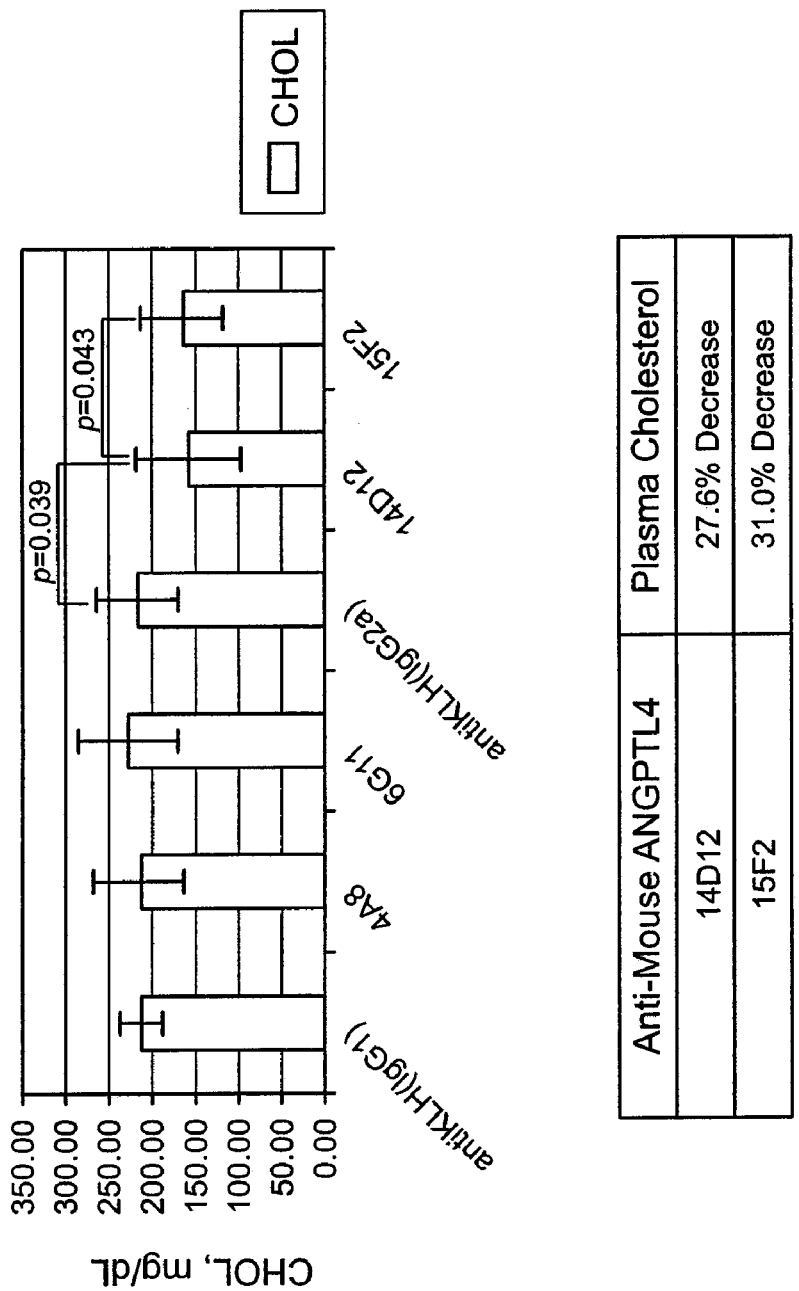

FIG. 21 shows fasted serum cholesterol levels in wild-type mice fed a high fat diet four days after injection of monoclonal antibodies against mouse ANGPTL4, as described in Example P.

FIG. 22 shows fasted serum triglyceride levels in wild-type mice fed a high fat diet after a single injection of monoclonal antibodies against mouse ANGPTL4 and after weekly injection of monoclonal antibodies against mouse ANGPTL4 for five weeks, as described in Example P.

FIG. 23 shows fasted serum cholesterol levels in wild-type mice fed a high fat diet after a single injection of monoclonal antibodies against mouse ANGPTL4 and after weekly injection of monoclonal antibodies against mouse ANGPTL4 for five weeks, as described in Example P.

Figure 24:
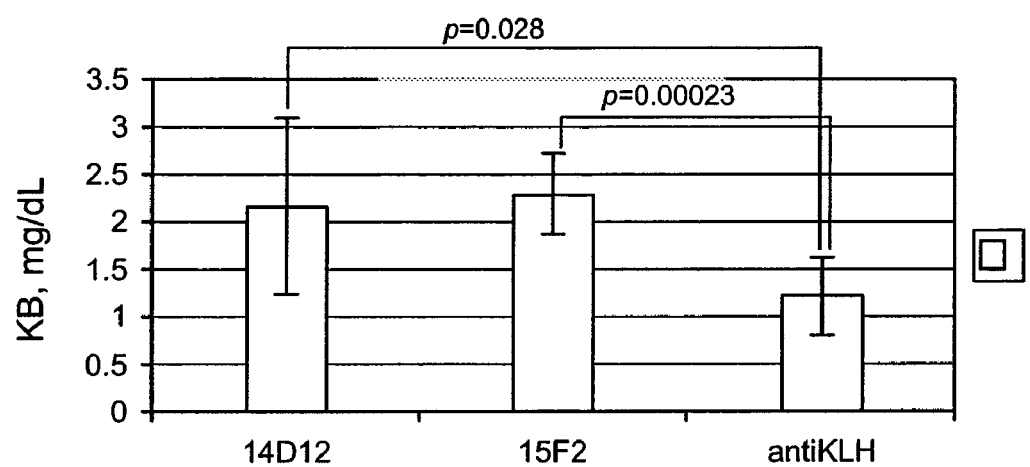

FIG. 24 shows fasted serum levels of ketone bodies in wild-type mice fed a high fat diet (HFD) after weekly injection of monoclonal antibodies against mouse ANGPTL4 for five weeks, as described in Example P.

FIG. 25 shows fasted serum triglyceride, total cholesterol, high density lipoprotein (HDL), and low density lipoprotein (LDL) levels in male wild-type ("WT"), heterozygous ("het"), and knockout ("hom") mice (panel A) and wild-type ("WT") and knockout ("hom") female mice (panel B) fed a standard ("chow") diet, as described in Example C.

Figure 26:
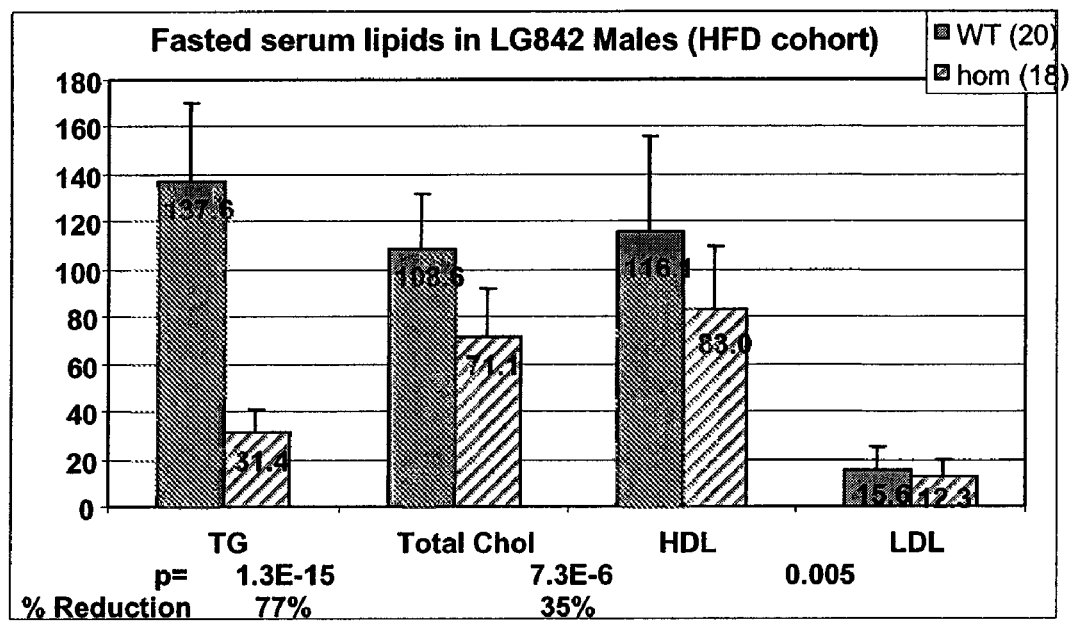

FIG. 26 shows fasted serum triglyceride, total cholesterol, high density lipoprotein (HDL), and low density lipoprotein (LDL) levels in male wild-type ("WT") and knockout ("hom") mice fed a high fat diet (HFD), as described in Example C.

Figure 27:
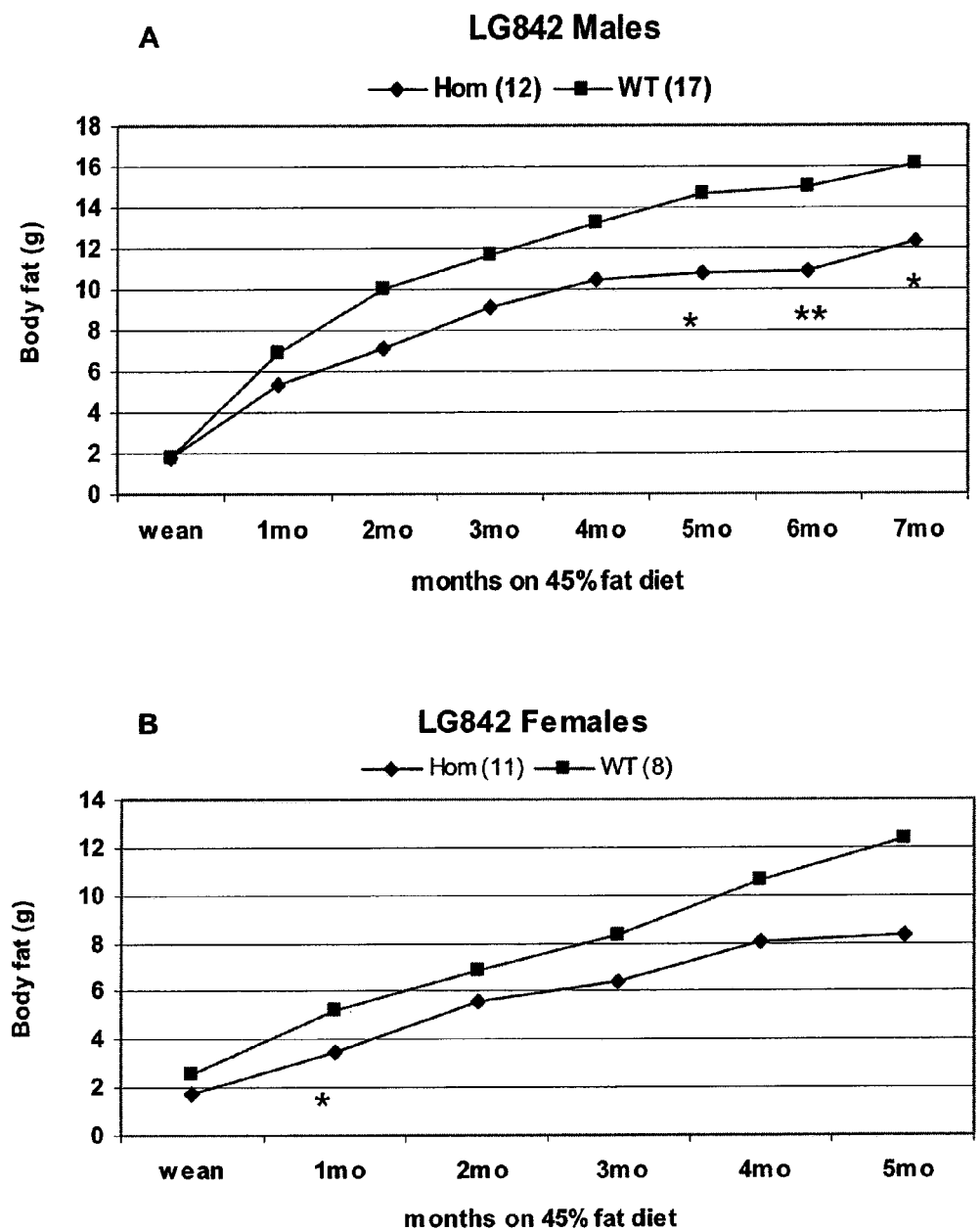

FIG. 27 shows grams of body fat in wild-type ("WT") and ANGPTL4 knockout ("Hom") male (panel A) and female (panel B) mice fed a high fat diet, as described in Example C.

FIG. 28 shows the food intake (panel A) and percent fecal fat (panel B) in wild-type ("WT") and ANGPTL4 knockout ("Hom") mice fed a high fat diet, as described in Example C.

Figures 29, 30:
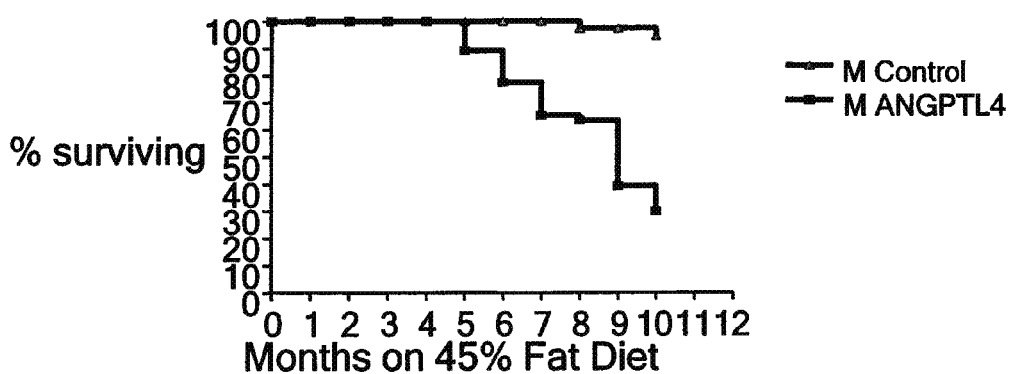

FIG. 29 shows the number of wild-type, heterozygous, and knockout pups born to interbred heterozygous parents, as discussed in Example C.

FIG. 30 shows the survival of wild-type and knockout mice fed a high fat diet (HFD), as discussed in Example C.

Figure 31:
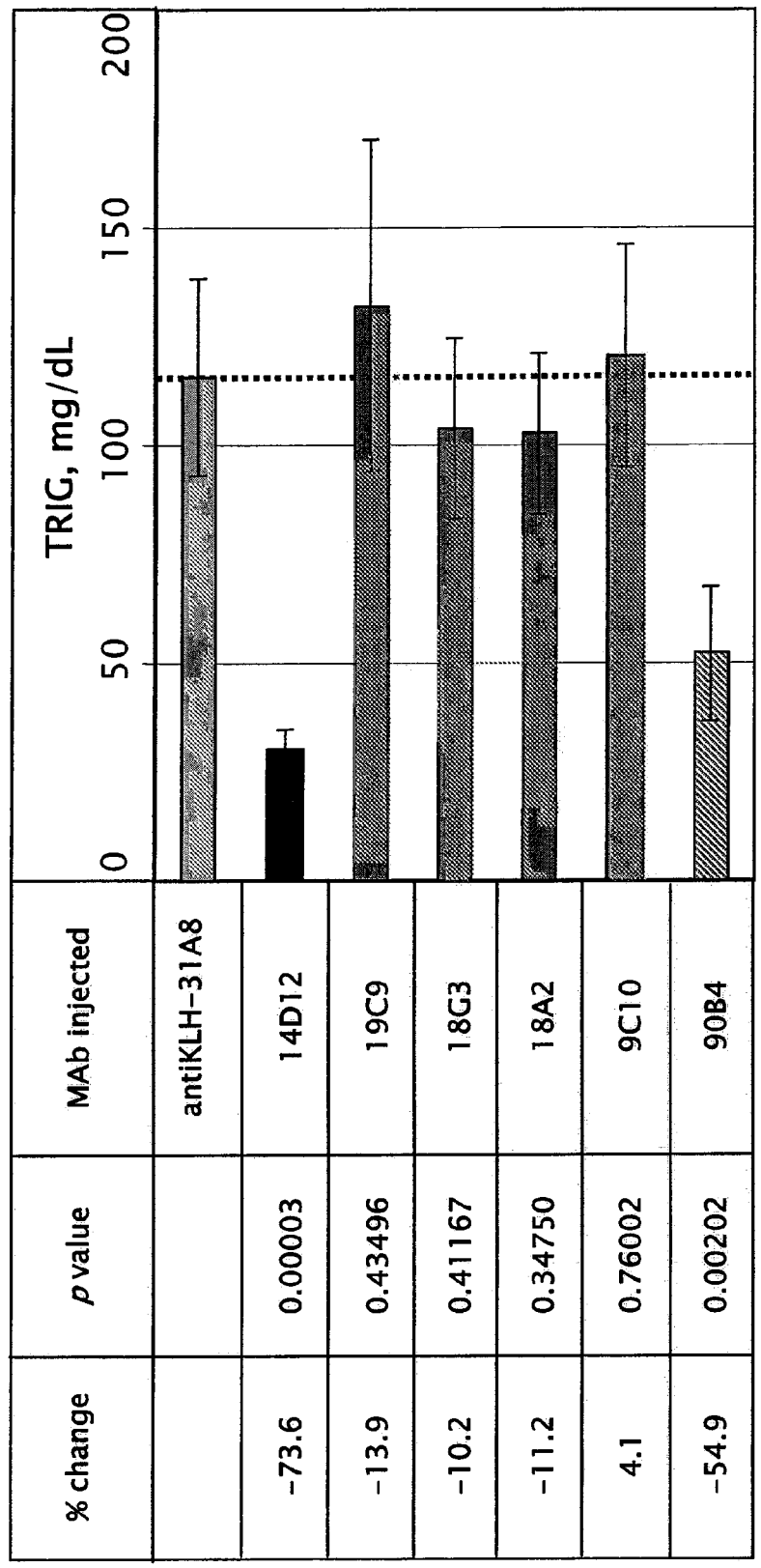

FIG. 31 shows fasted serum triglyceride levels in wild-type mice injected with monoclonal antibodies against ANGPTL4, as described in Example R.

Figure 32:
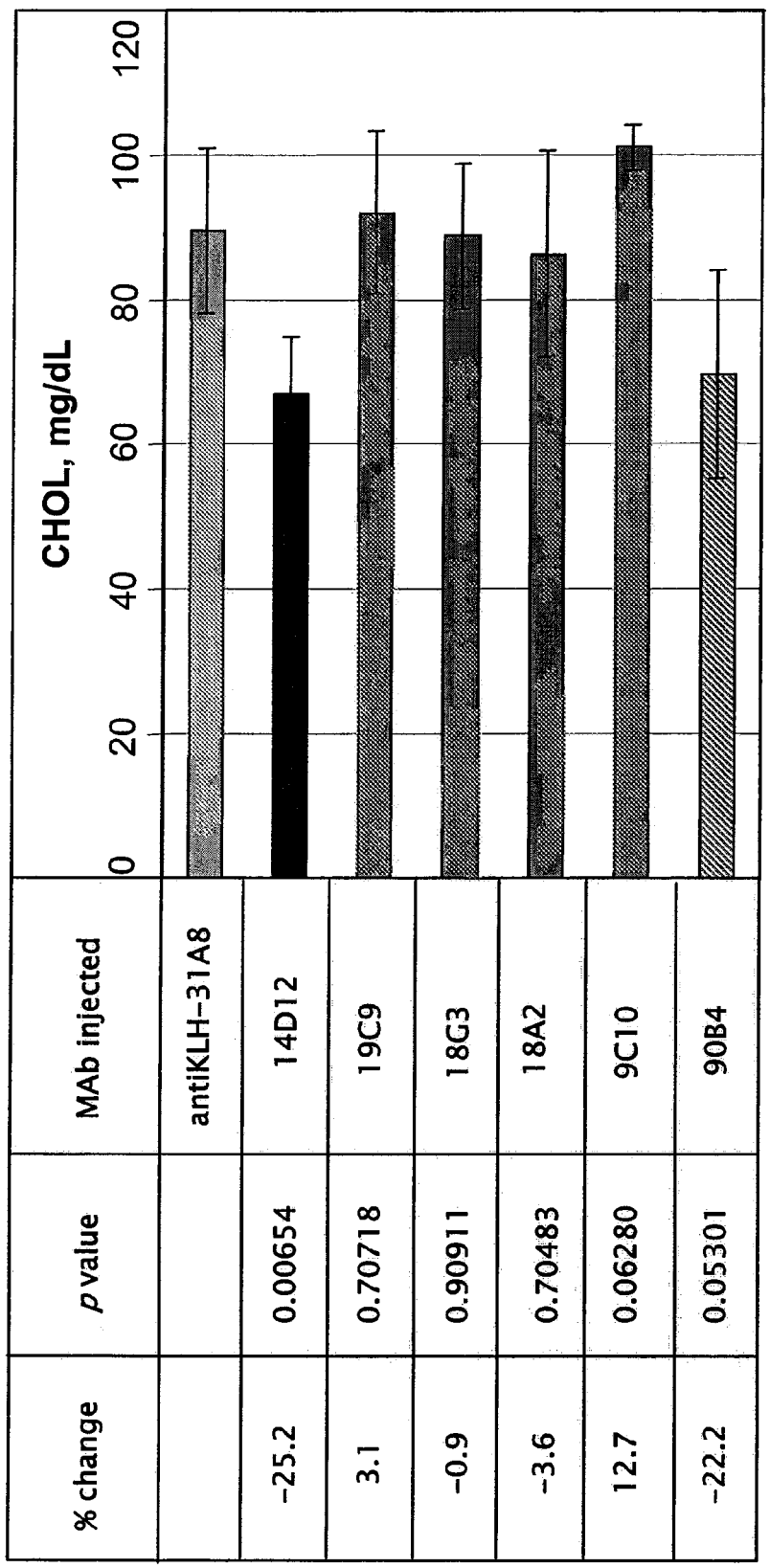

FIG. 32 shows fasted total cholesterol levels in wild-type mice injected with monoclonal antibodies against ANGPTL4, as described in Example R.

Figure 33:
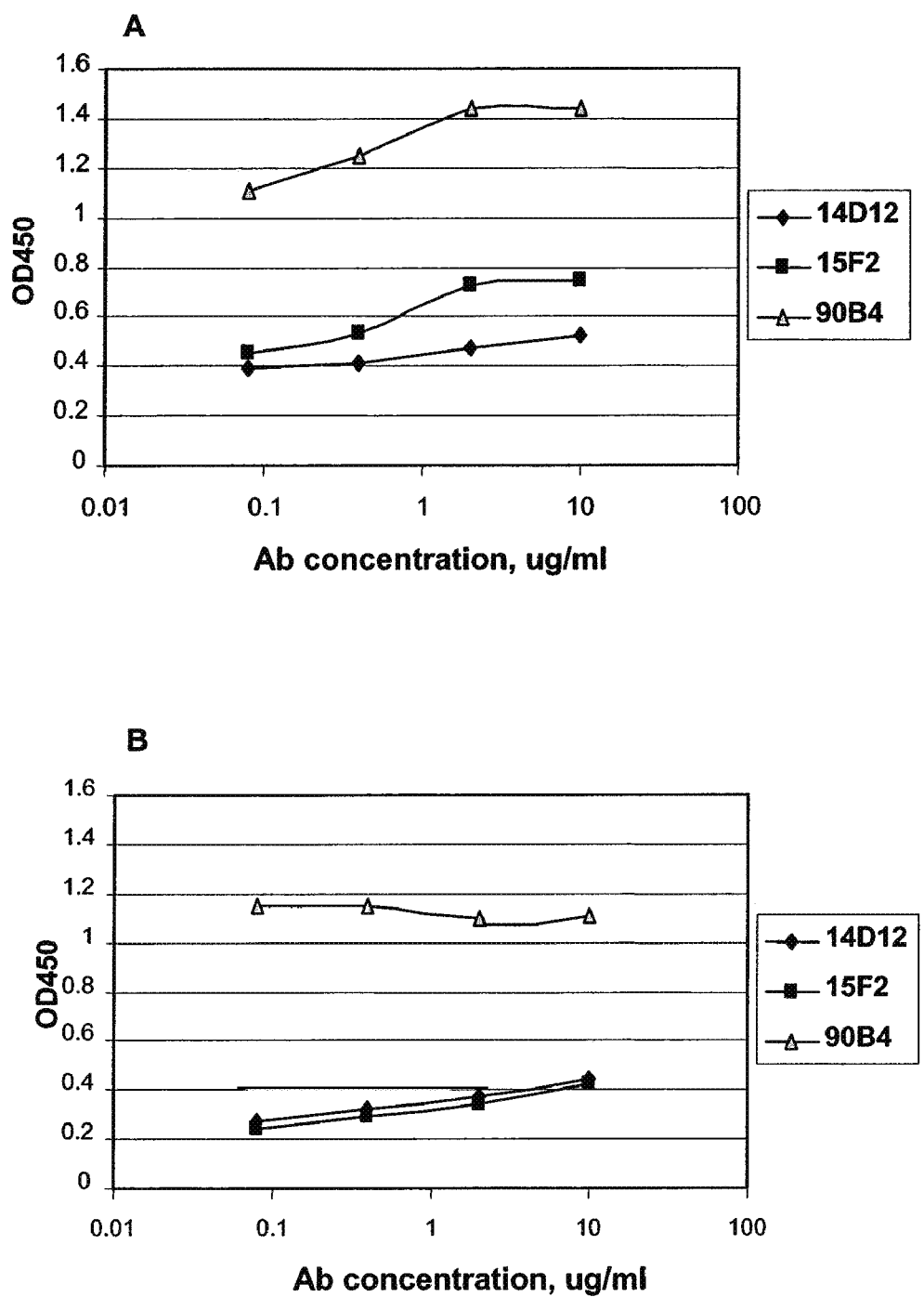

FIG. 33 shows the relative binding affinity of monoclonal antibodies 14D12, 15F2, and 90B4 for N-mANGPTL4 (panel A) and N-hANGPTL4 (panel B), as described in Example S.

FIG. 34 shows percent reduction in fasted serum triglycerides in wild-type mice at day 4 (panel A) and day 7 (panel B) after injection with either 14D12 or anti-KLH, as described in Example T.

Figure 35:
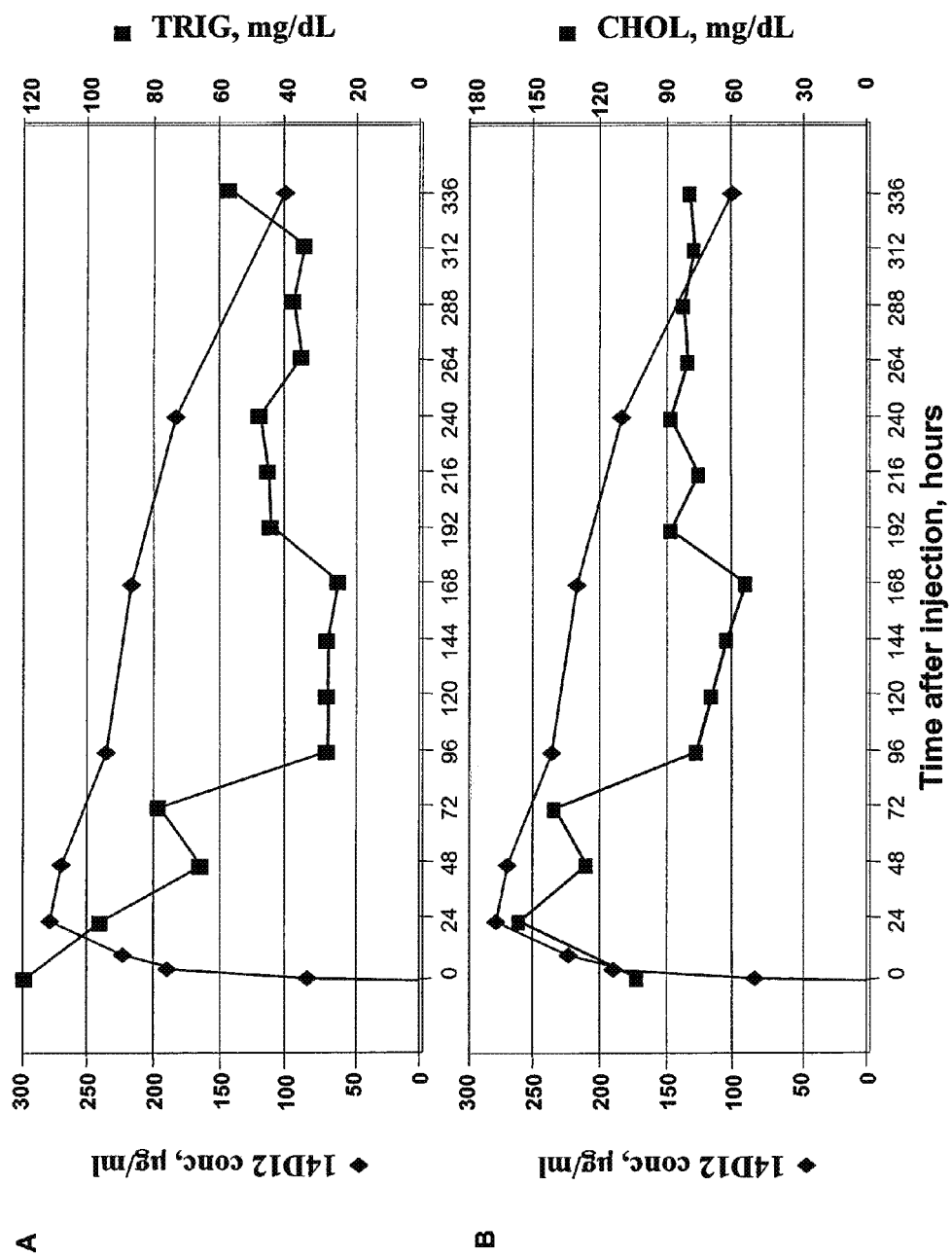

FIG. 35, panel A, shows a plot of 14D12 concentration and fasted serum triglyceride levels in wild-type mice over time after a single injection of 14D12, as described in Example U. Panel B shows a plot of 14D12 concentration and fasted total cholesterol levels in wild-type mice over time after a single injection of 14D12, as described in Example U.

Figure 36:
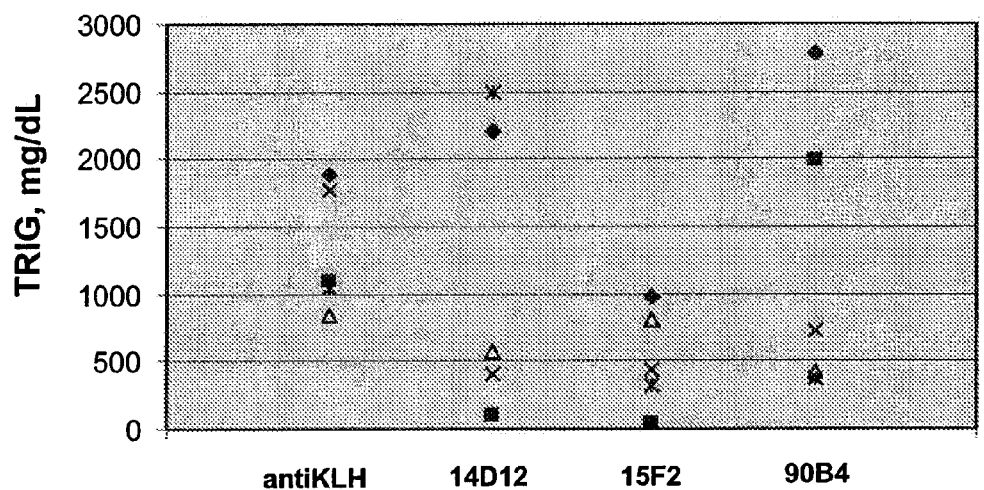

FIG. 36 shows fasted serum triglyceride levels in mice that overexpress human ANGPTL4 four days after injection with monoclonal antibody anti-KLH, 14D12, 15F2, or 90B4, as described in Example V.

Figure 37:
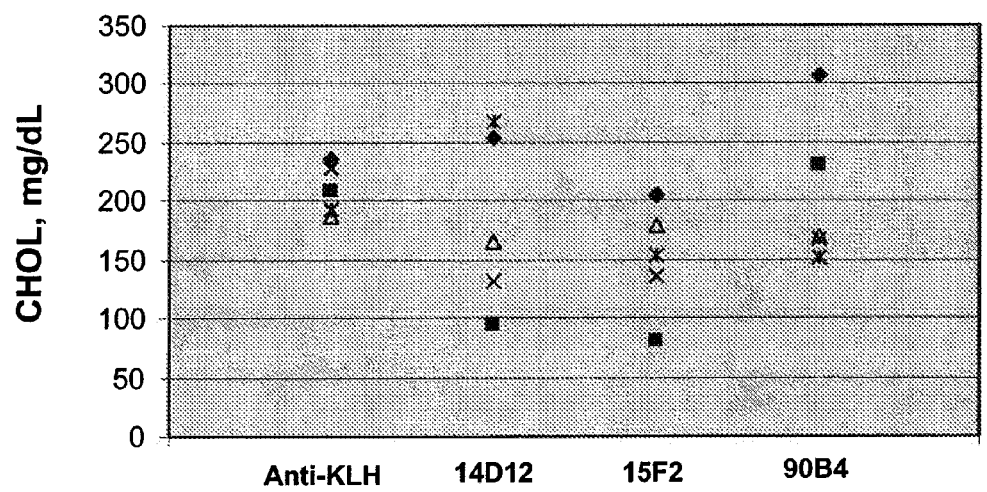

FIG. 37 shows fasted total cholesterol levels in mice that overexpress human ANGPTL4 four days after injection with monoclonal antibody anti-KLH, 14D12, 15F2, or 90B4, as described in Example V.

Figure 38:
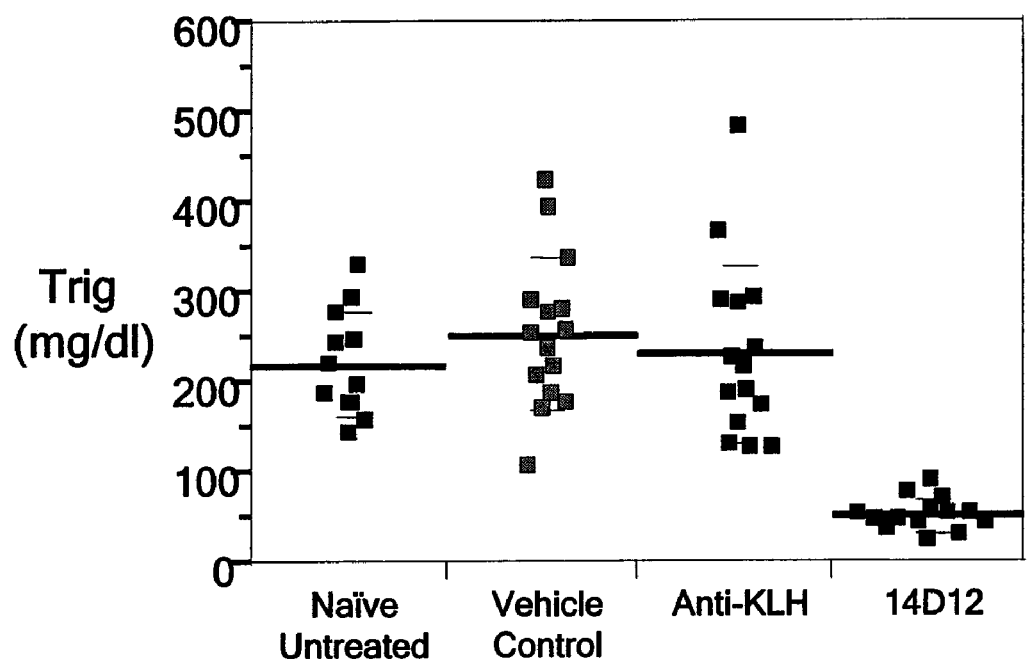

FIG. 38 shows fasted serum triglyceride levels in LDLr knockout mice after fifteen weekly injections with vehicle, anti-KLH, or 14D12, as discussed in Example W.

Figure 39:
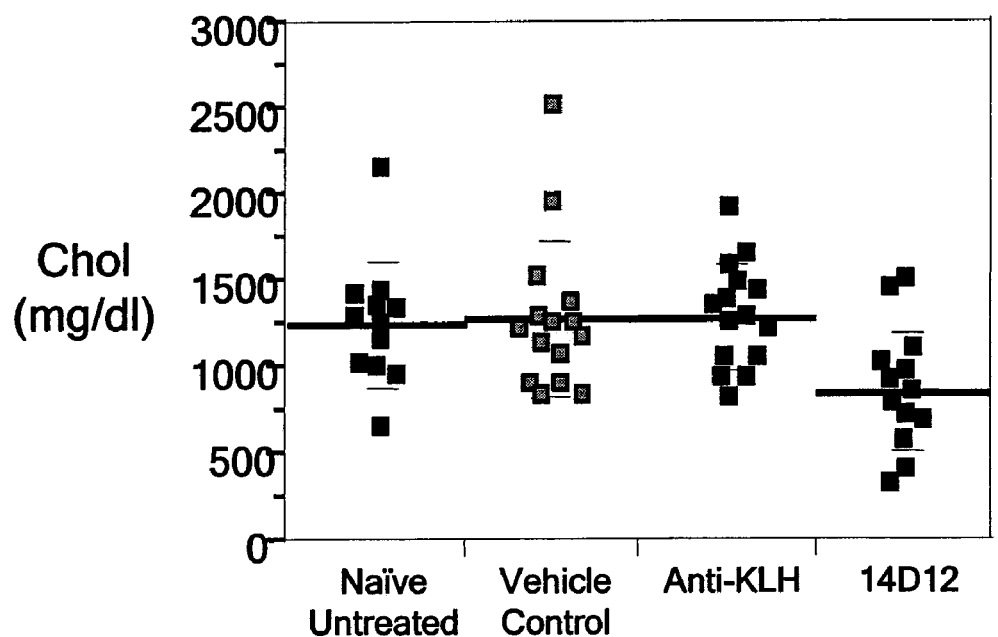

FIG. 39 shows fasted total cholesterol levels in LDLr knockout mice after fifteen weekly injections with vehicle, anti-KLH, or 14D12, as discussed in Example W.

Figure 40:
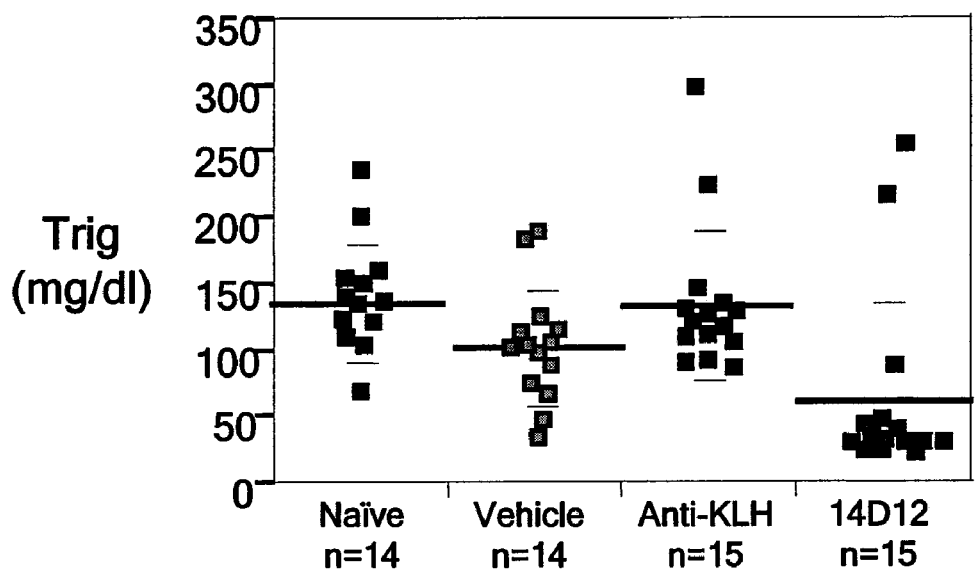

FIG. 40 shows fasted serum triglyceride levels in ApoE knockout mice after fifteen weekly injections with vehicle, anti-KLH, or 14D12, as discussed in Example X.

Figure 41:
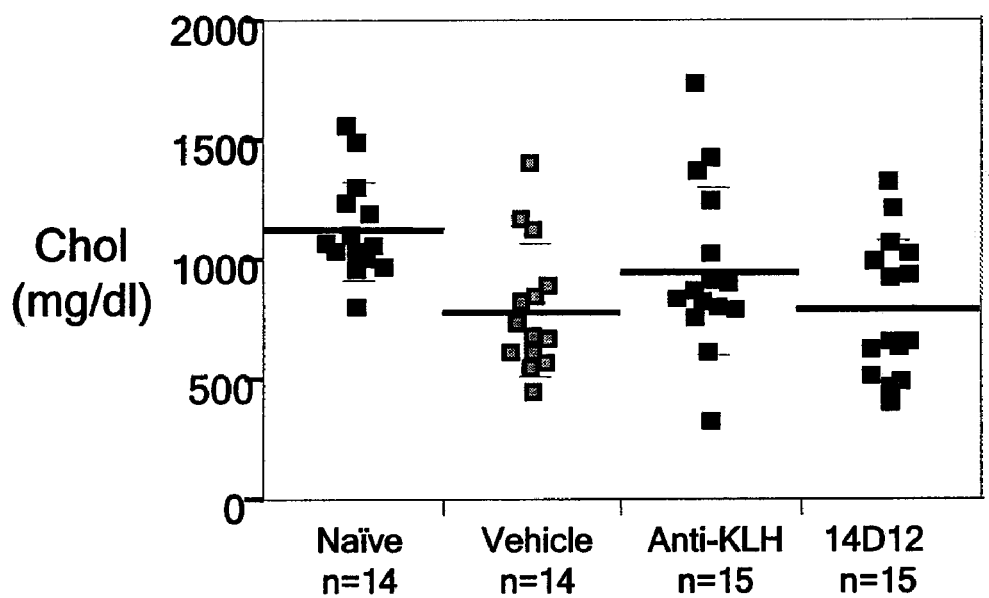

FIG. 41 shows fasted total cholesterol levels in ApoE knockout mice after fifteen weekly injections with vehicle, anti-KLH, or 14D12, as discussed in Example X.

Figure 42:
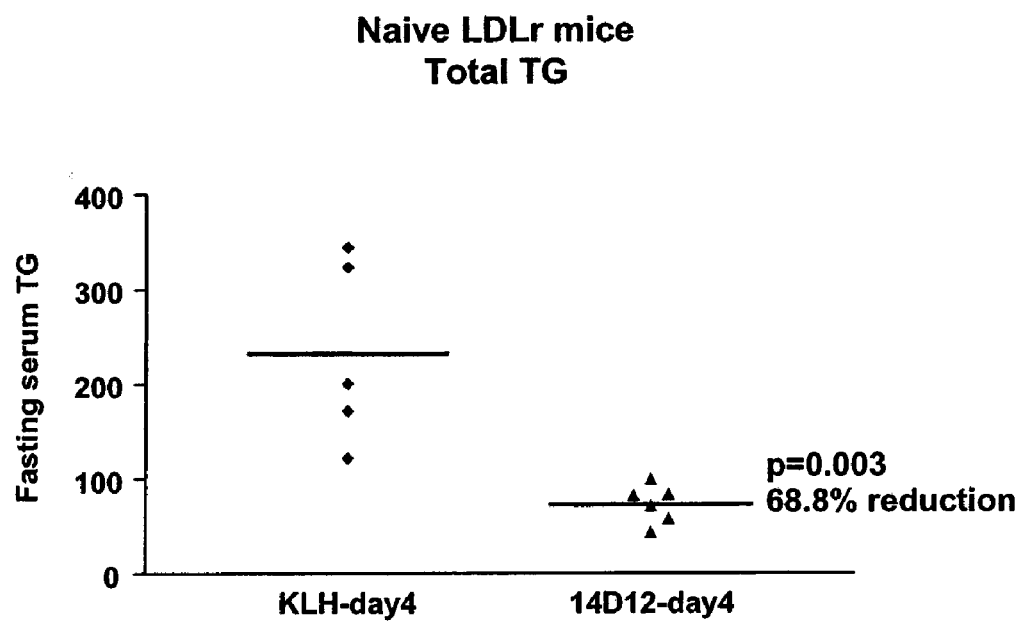

FIG. 42 shows fasted serum triglyceride levels in LDLr knockout mice four days after a single injection with anti-KLH or 14D12, as discussed in Example W.

Figure 43:
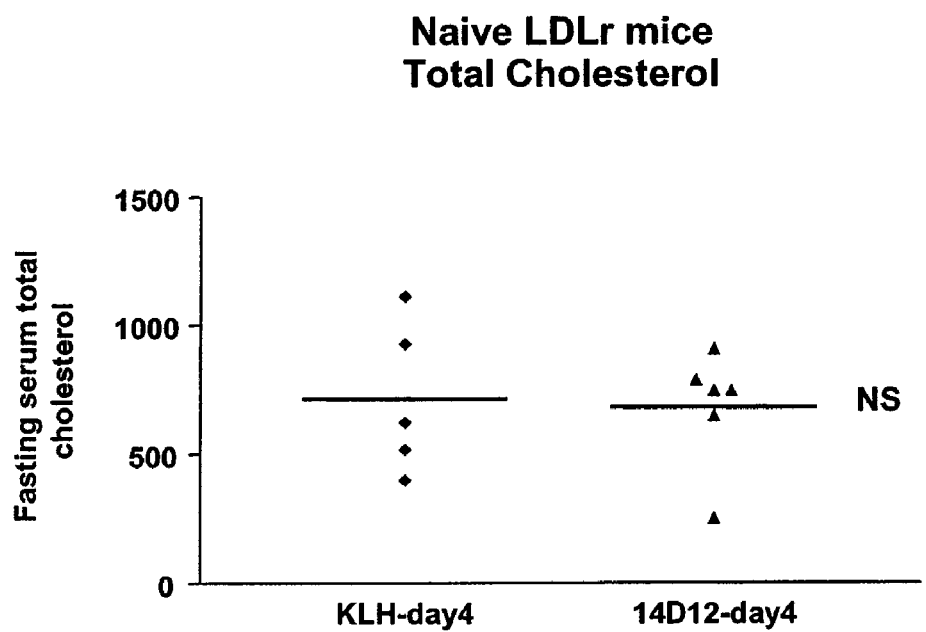

FIG. 43 shows fasted total cholesterol levels in LDLr knockout mice four days after a single injection with anti-KLH or 14D12, as discussed in Example W.

Figure 44:
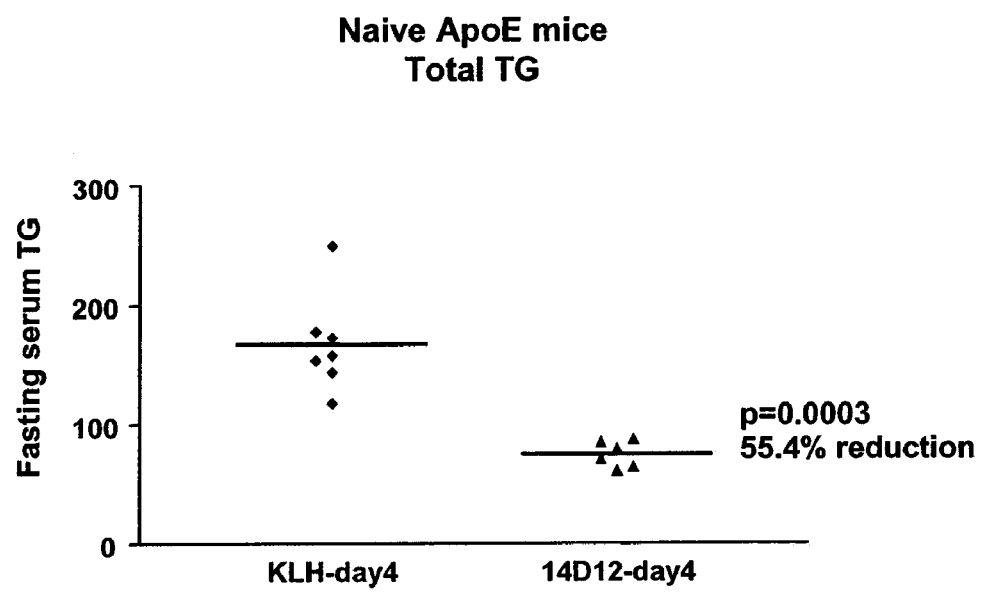

FIG. 44 shows fasted serum triglyceride levels in ApoE knockout mice four days after a single injection with anti-KLH or 14D12, as discussed in Example X.

Figure 45:
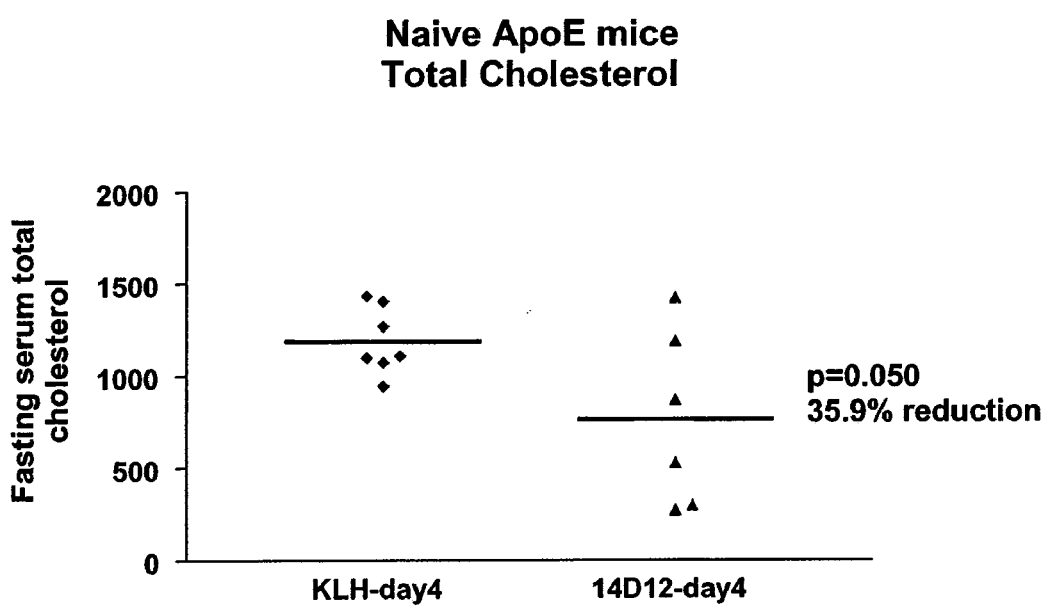

FIG. 45 shows fasted total cholesterol levels in ApoE knockout mice four days after a single injection with anti-KLH or 14D12, as discussed in Example X.

Figure 46:
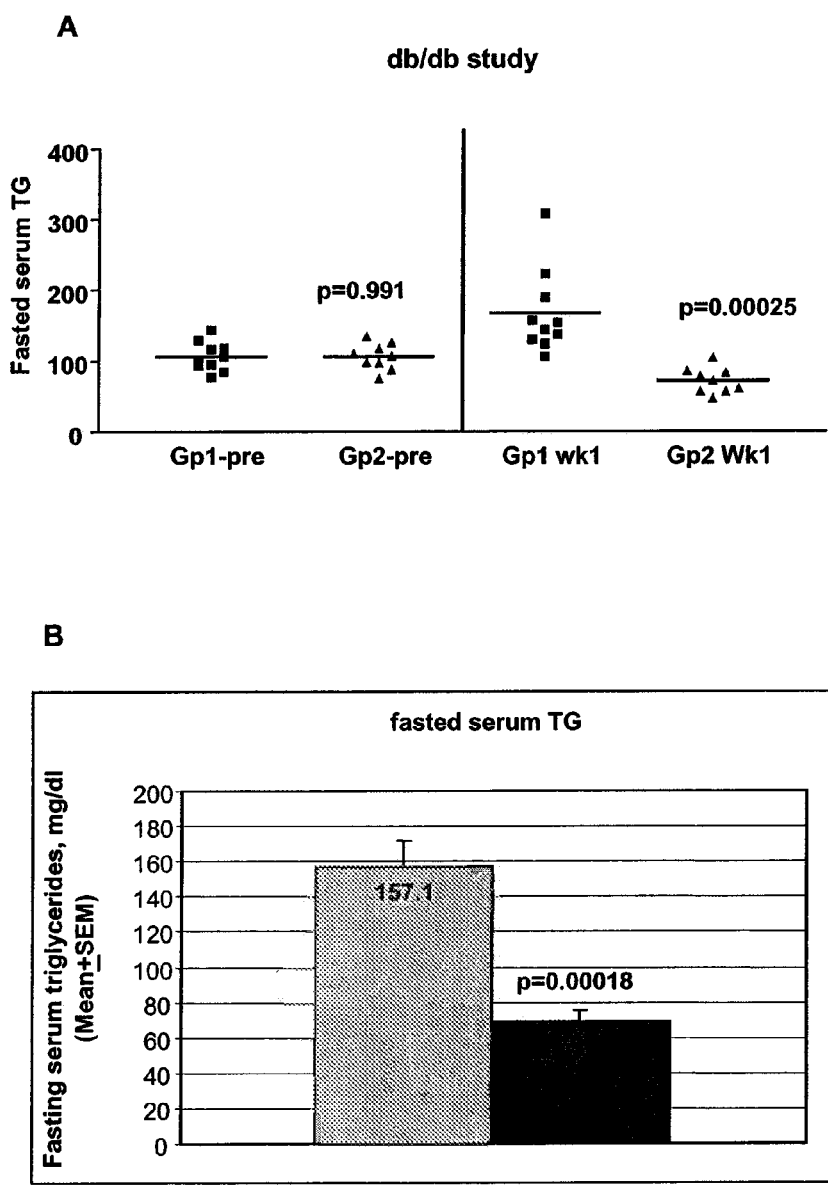

FIG. 46, panel A shows fasted serum triglycerides in db/db mice before and one week after injection with injection with anti-KLH (Grp-1) and 14D12 (Grp-2), as described in Example Y. Panel B shows serum triglycerides in db/db mice after 8 weekly injections with anti-KLH or 14D12, as discussed in Example Y.

FIG. 47 shows an alignment of the heavy chain variable regions of 14D12 (SEQ ID NO: 12), 15F2 (SEQ ID NO: 13), and 90B4 (SEQ ID NO: 14), as described in Example Z. The consensus sequence (SEQ ID NO: 15) is also shown. The percent homology between each pair of heavy chain variable regions is shown below.

FIG. 48 shows an alignment of the light chain variable regions of 14D12 (SEQ ID NO: 16), 15F2 (SEQ ID NO: 17), and 90B4 (SEQ ID NO: 18), as described in Example Z. The consensus sequence (SEQ ID NO: 19) is also shown. The percent homology between each pair of light chain variable regions is shown below.

Figure 49:
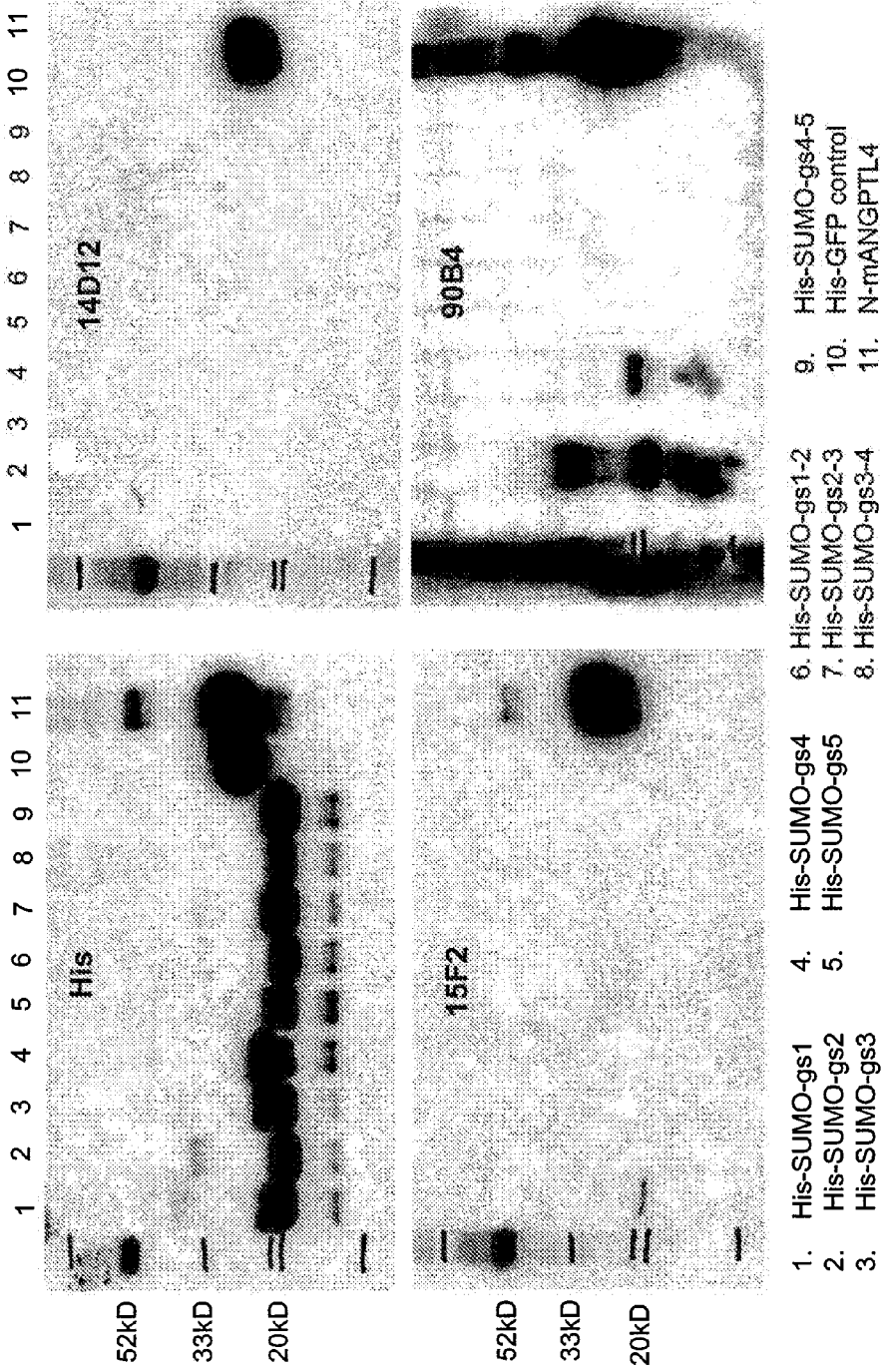

FIG. 49 shows binding of certain monoclonal antibodies against ANGPTL4 to fragments of ANGPTL4, as discussed in Example AA.

V. DETAILED DESCRIPTION OF VARIOUS EMBODIMENTS

It is to be understood that both the foregoing general description and the following detailed description are exemplary and explanatory only and are not restrictive of the invention, as claimed.

In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated literature and similar materials defines a term that contradicts that term's definition in this application, this application controls.

A. CERTAIN DEFINITIONS

The terms "polypeptide," "peptide," and "protein" are used interchangeably herein to refer to a polymer of amino acid residues. The terms apply to amino acid polymers containing naturally occurring amino acids as well as amino acid polymers in which one or more amino acid residues is an artificial chemical analogue of a corresponding naturally occurring amino acid. The amino acid polymers can be of any length.

The term "antibody," as used herein, refers to an intact antibody or a fragment of an antibody that competes with the intact antibody for antigen binding. Antibody fragments include, but are not limited to, Fab, Fab', F(ab')$_2$, Fv, scFv, Fd, diabodies, and other antibody fragments that retain at least a portion of the variable region of an intact antibody. See, e.g., Hudson et al. (2003) *Nature Med.* 9:129-134. In certain embodiments, antibody fragments are produced by enzymatic or chemical cleavage of intact antibodies. In certain embodiments, antibody fragments are produced by recombinant DNA techniques.

The term "native polypeptide" refers to a naturally occurring polypeptide. The term "native antibody" refers to a naturally occurring antibody.

The term "monoclonal antibody" refers to an antibody from a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) *Nature,* 256: 495-499). In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library (see, e.g., Clackson et al. (1991) *Nature* 352: 624-628, and Marks et al. (1991) *J. Mol. Biol.* 222: 581-597). For various other monoclonal antibody production techniques, see, e.g., Harlow and Lane (1988) *Antibodies: A Laboratory Manual* (Cold Spring Harbor Laboratory, Cold Spring Harbor, N.Y.).

A "chimeric" antibody refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

An antibody "specifically binds" an antigen when it preferentially recognizes the antigen in a complex mixture of proteins and/or macromolecules. In certain embodiments, an antibody comprises an antigen-binding site that specifically binds to a particular epitope. In certain such embodiments, the antibody is capable of binding different antigens so long as the different antigens comprise that particular epitope. In certain instances, for example, homologous proteins from different species may comprise the same epitope. In certain embodiments, an antibody is said to specifically bind an antigen when the dissociation constant ($K_D$) is $\leq 1$ µM, in certain embodiments, when the dissociation constant is $\leq 100$ nM, and in certain embodiments, when the dissociation constant is $\leq 10$ nM.

The term "ANGPTL4" refers to an angiopoietin like protein 4 from any vertebrate or mammalian source, including, but not limited to, human, bovine, chicken, rodent, mouse, rat, porcine, ovine, primate, monkey, and guinea pig, unless specified otherwise. The term also refers to fragments and variants of native ANGPTL4 that maintain at least one in vivo or in vitro activity of a native ANGPTL4. The term encompasses full-length unprocessed precursor forms of ANGPTL4 as well as mature forms resulting from post-translational cleavage of the signal peptide and forms resulting from proteolytic processing of the fibrinogen domain. In certain embodiments, a full-length, unprocessed mouse ANGPTL4 has the amino acid sequence set forth in SEQ ID NO: 1. In certain embodiments, a full-length, unprocessed mouse ANGPTL4 has the amino acid sequence set forth in SEQ ID NO: 50. In certain embodiments, a full-length, unprocessed human ANGPTL4 has the amino acid sequence set forth in SEQ ID NO:2.

The term "Angptl4" refers to a nucleic acid encoding ANGPTL4.

The term "LPL" refers to a lipoprotein lipase from any vertebrate or mammalian source, including, but not limited to, human, bovine, chicken, rodent, mouse, rat, porcine, ovine, primate, monkey, and guinea pig. In certain embodiments, a lipoprotein lipase catalyzes the hydrolysis of triacylglycerol in chylomicrons and very low density lipoproteins (VLDLs) into diacylglycerol and a free fatty acid anion. In certain embodiments, a lipoprotein lipase is also able to hydrolyze diacylglycerol.

The term "agent" refers to a chemical compound, a mixture of chemical compounds, a biological macromolecule, or an extract made from biological materials.

The term "antagonist" refers to an agent that reduces an activity of ANGPTL4.

The term "agonist" refers to an agent that increases an activity of ANGPTL4.

The term "patient" includes human and animal subjects. In certain embodiments, a patient is a mammal. In certain such embodiments, a patient is a human.

A "fragment" of a reference polypeptide refers to a contiguous stretch of amino acids from any portion of the reference polypeptide. A fragment may be of any length that is less than the length of the reference polypeptide.

A "variant" of a reference polypeptide refers to a polypeptide having one or more amino acid substitutions, deletions, or insertions relative to the reference polypeptide.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: H is, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of a human antibody that are homologous with non-human antibodies, or into the non-homologous regions of the molecule.

In making substitutions, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein, in certain instances, is understood in the art. Kyte et al., *J. Mol. Biol.*, 157:105-131 (1982). It is known that in certain instances, certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residue | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4 Diaminobutyric Acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

A skilled artisan will be able to determine suitable variants of a polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, in certain embodiments, one skilled in the art can review structure-function studies identifying residues in similar polypeptides that are important for activity or structure. In view of such a comparison, in certain embodiments, one can predict the importance of amino acid residues in a protein that correspond to amino acid residues which are important for activity or structure in similar proteins. In certain embodiments, one skilled in the art may opt for chemically similar amino acid substitutions for such predicted important amino acid residues.

In certain embodiments, one skilled in the art can also analyze the three-dimensional structure and amino acid sequence in relation to that structure in similar polypeptides. In certain embodiments, in view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, in certain embodiments, one skilled in the art may generate test variants containing a single amino acid substitution at each desired amino acid residue. In certain embodiments, the variants can then be screened using activity assays known to those skilled in the art. In certain embodiments, such variants could be used to gather information about suitable variants. For example, in certain embodiments, if one discovered that a change to a particular amino acid residue resulted in destroyed, undesirably reduced, or unsuitable activity, variants with such a change may be avoided. In other words, in certain embodiments, based on information gathered from such routine experiments, one skilled in the art can readily determine the amino acids where further substitutions should be avoided either alone or in combination with other mutations.

A number of scientific publications have been devoted to the prediction of secondary structure. See, e.g., Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The growth of the protein structural database (PDB) has provided enhanced predictability of secondary structure, including the potential number of folds within a polypeptide's structure. See, e.g., Holm et al., *Nucl. Acid. Res.*, 27(1):244-247 (1999). It has been suggested (Brenner et al., *Curr. Op. Struct. Biol.*, 7(3):369-376 (1997)) that there are a limited number of folds in a given polypeptide or protein and that once a critical number of structures have been resolved, structural prediction will become dramatically more accurate.

Additional methods of predicting secondary structure include "threading" (see, e.g., Jones, D., *Curr. Opin. Struct. Biol.*, 7(3):377-87 (1997); Sippl et al., *Structure*, 4(1):15-19 (1996)), "profile analysis" (see, e.g., Bowie et al., *Science*, 253:164-170 (1991); Gribskov et al., *Meth. Enzym.*, 183:146-159 (1990); Gribskov et al., *Proc. Nat. Acad. Sci.*, 84(13): 4355-4358 (1987)), and "evolutionary linkage" (see, e.g., Holm et al., *Nucl. Acid. Res.*, 27(1):244-247 (1999), and Brenner et al., *Curr. Op. Struct. Biol.*, 7(3):369-376 (1997)).

In certain embodiments, a variant of a reference antibody includes a glycosylation variant wherein the number and/or type of glycosylation sites have been altered relative to the amino acid sequence of the reference antibody. In certain embodiments, a variant of a polypeptide comprises a greater or a lesser number of N-linked glycosylation sites relative to a native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. In certain embodiments, a rearrangement of N-linked carbohydrate chains is provided, wherein one or more N-linked glycosylation sites (typically those that are naturally occurring) are eliminated and one or more new N-linked sites are created. Exemplary antibody variants include cysteine variants wherein one or more cysteine residues are deleted from or substituted for another amino acid (e.g., serine) relative to the amino acid sequence of the reference antibody. In certain embodiments, cysteine variants may be useful when antibodies must be refolded into a biologically active conformation such as after the isolation of insoluble inclusion bodies. In certain embodiments, cysteine variants have fewer cysteine residues than the native polypeptide. In certain embodiments, cysteine variants have an even number of cysteine residues to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in a naturally-occurring sequence (in certain embodiments, in the portion of the polypeptide outside the domain(s) forming intermolecular contacts). In certain embodiments, a conservative amino acid substitution typically may not substantially change the structural characteristics of the reference sequence (e.g., in certain embodiments, a replacement amino acid should not tend to break a helix that occurs in the reference sequence, or disrupt other types of secondary structure that characterizes the reference sequence). Examples of certain art-recognized polypeptide secondary and tertiary structures are described, for example, in *Proteins, Structures and Molecular Principles* (Creighton, Ed., W.H. Freeman and Company, New York (1984)); Introduction to Protein Structure (C. Branden and J. Tooze, eds., Garland Publishing, New York, N.Y. (1991)); and Thornton et at. Nature 354:105 (1991).

"Percent identity" or "% identity," with reference to nucleic acid sequences, refers to the percentage of identical nucleotides between at least two polynucleotide sequences aligned using the Basic Local Alignment Search Tool (BLAST) engine. See Tatusova et al. (1999) *FEMS Microbiol Lett.* 174:247-250. The BLAST engine (version 2.2.10) is provided to the public by the National Center for Biotechnology Information (NCBI), Bethesda, Md. To align two polynucleotide sequences, the "Blast 2 Sequences" tool is used, which employs the "blastn" program with parameters set at default values as follows:

Matrix: not applicable
Reward for match: 1
Penalty for mismatch: −2
Open gap: 5 penalties
Extension gap: 2 penalties
Gap_x dropoff: 50
Expect: 10.0
Word size: 11
Filter: on "Percent identity" or "% identity," with reference to polypeptide sequences, refers to the percentage of identical amino acids between at least two polypeptide sequences aligned using the Basic Local Alignment Search Tool (BLAST) engine. See Tatusova et al. (1999) *FEMS Microbiol Lett.* 174:247-250. The BLAST engine (version 2.2.10) is provided to the public by the National Center for Biotechnology Information (NCBI), Bethesda, Md. To align two polypeptide sequences, the "Blast 2 Sequences" tool is used, which employs the "blastp" program with parameters set at default values as follows:

Matrix: BLOSUM62
Open gap: 11 penalties
Extension gap: 1 penalty
Gap_x dropoff: 50
Expect: 10.0
Word size: 3
Filter: on The term "effective dose" or "effective amount" refers to an amount of an agent, e.g., a neutralizing antibody, that results in the reduction of symptoms in a patient or results in a desired biological outcome. In certain embodiments, an effective dose or effective amount is sufficient to reduce at least one activity of ANGPTL4. In certain embodiments, an effective dose or effective amount is determined as described below, Part V.G.

The term "treatment" encompasses both therapeutic and prophylactic/preventative measures unless otherwise indicated. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic agent" refers to an agent that may be administered in vivo to bring about a therapeutic and/or prophylactic/preventative effect.

A "therapeutic antibody" refers to an antibody that may be administered in vivo to bring about a therapeutic and/or prophylactic/preventative effect.

The terms "isolated nucleic acid" and "isolated polynucleotide" are used interchangeably and refer to a polynucleotide of genomic, cDNA, or synthetic origin or some combination thereof. An "isolated polynucleotide" (1) is not associated with all or a portion of a polynucleotide in which the "isolated polynucleotide" is found in nature, (2) is linked to a polynucleotide to which it is not linked in nature, or (3) does not occur in nature as part of a larger sequence.

B. STRUCTURE OF NATIVE ANTIBODIES AND CERTAIN ANTIBODY FRAGMENTS

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_H1$, $C_H2$, and $C_H3$. The $V_H$ domain is at the amino-terminus of the heavy chain, and the $C_H3$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., *Fundamental Immunology* (1989) ch. 7 (Paul, W., ed., 2nd ed. Raven Press, N.Y.).

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) *Sequences of Proteins of Immunological Interest* (National Institutes of Health, Publication No. 91-3242, vols. 1-3, Bethesda, Md.); Chothia & Lesk *J. Mol. Biol.* 196:901-917 (1987); or Chothia et al. *Nature* 342:878-883 (1989). In the present application, the term "CDR" refers to a CDR from either the light or heavy chain, unless otherwise specified.

A "Fab" fragment comprises one light chain and the $C_H1$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_H1$ and $C_H2$ domains. An interchain disulfide bond can be formed between two heavy chains of a Fab' fragment to form a "F(ab')$_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203. In certain instances, a single variable region (one-half of an Fv) may have the ability to recognize and bind antigen, albeit with lower affinity than the Fv.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

C. CERTAIN ANTIBODIES

In certain embodiments, monoclonal antibodies that, specifically bind to ANGPTL4 are provided. In certain such embodiments, the monoclonal antibodies are neutralizing monoclonal antibodies that reduce at least one activity of ANGPTL4 in vivo and/or in vitro.

In certain embodiments, a neutralizing monoclonal antibody against ANGPTL4 rescues LPL activity in the presence of ANGPTL4 in vitro. In certain embodiments, a neutralizing monoclonal antibody against ANGPTL4 reduces at least one serum lipid level in vivo. In certain embodiments, a neutralizing monoclonal antibody against ANGPTL4 reduces serum triglyceride levels in vivo. In certain embodiments, a neutralizing monoclonal antibody reduces total cholesterol levels in vivo. In certain embodiments, a neutralizing monoclonal antibody against ANGPTL4 reduces free fatty acid (FFA) levels in vivo.

In certain embodiments, a neutralizing monoclonal antibody against ANGPTL4 reduces serum triglycerides in LDLr knockout mice in vivo. In certain embodiments, a neutralizing monoclonal antibody against ANGPTL4 reduces total cholesterol in LDLr knockout mice in vivo. In certain embodiments, a neutralizing monoclonal antibody against ANGPTL4 reduces serum triglycerides in ApoE knockout mice in vivo. In certain embodiments, a neutralizing monoclonal antibody against ANGPTL4 reduces total cholesterol in ApoE knockout mice in vivo. In certain embodiments, a neutralizing monoclonal antibody against ANGPTL4 reduces serum triglycerides in db/db mice in vivo. In certain embodiments, a neutralizing monoclonal antibody against ANGPTL4 reduces total cholesterol in db/db mice in vivo.

In certain embodiments, neutralizing monoclonal antibodies that specifically bind to mouse ANGPTL4 are provided. In certain embodiments, neutralizing monoclonal antibodies that specifically bind to human ANGPTL4 are provided. In certain embodiments, neutralizing monoclonal antibodies that specifically bind to the same epitope in ANGPTL4 from different species (i.e., antibodies that demonstrate cross-reactivity) are provided. In certain such embodiments, the antibodies specifically bind to both mouse ANGPTL4 and human ANGPTL4.

In certain embodiments, neutralizing monoclonal antibodies that specifically bind to an epitope within the N-terminal coiled-coil domain of ANGPTL4 are provided. In certain embodiments, neutralizing monoclonal antibodies that specifically bind to an epitope within the N-terminal coiled-coil domain of mouse ANGPTL4 are provided. In certain embodiments, neutralizing monoclonal antibodies specifically bind to an epitope within a region of mouse ANGPTL4 (SEQ ID NO:1 or SEQ ID NO: 50) from residue 21 to residue 174. In certain embodiments, neutralizing monoclonal antibodies that specifically bind to an epitope within the N-terminal coiled-coil domain of human ANGPTL4 are provided. In certain embodiments, neutralizing monoclonal antibodies specifically bind to an epitope within a region of human ANGPTL4 (SEQ ID NO:2) from residue 21 to residue 169.

In certain embodiments, neutralizing monoclonal antibodies are non-human monoclonal antibodies. In certain such embodiments, neutralizing monoclonal antibodies are rodent monoclonal antibodies. In certain such embodiments, neutralizing monoclonal antibodies are mouse monoclonal antibodies. In certain embodiments, neutralizing monoclonal antibodies are chimeric monoclonal antibodies. In certain embodiments, neutralizing monoclonal antibodies are humanized monoclonal antibodies. In certain embodiments, neutralizing monoclonal antibodies are human monoclonal antibodies. In certain embodiments, chimeric, humanized, and/or human monoclonal antibodies are useful as therapeutic antibodies in humans.

In certain embodiments, neutralizing monoclonal antibodies are antibody fragments. Exemplary antibody fragments include, but are not limited to, Fab, Fab', F(ab')$_2$, Fv, scFv, Fd, diabodies, and other antibody fragments.

Exemplary neutralizing monoclonal antibodies, designated 14D12, 90B4, and 15F2, are provided. Those antibodies bind to an epitope within residues 21 to 174 of mouse ANGPTL4 (SEQ ID NO: 1 or SEQ ID NO: 50). Those antibodies also neutralize ANGPTL4 activity. Thus, antibodies that bind the same epitope (e.g., in either human or mouse ANGPTL4) would be expected to also possess neutralizing activity. Certain neutralizing monoclonal antibodies against ANGPTL4 bind to one or more peptides chosen from SEQ ID NOs: 40 to 48. Certain neutralizing monoclonal antibodies against ANGPTL4 bind to one or more peptides chosen from SEQ ID NOs: 40 to 43. In certain embodiments, a neutralizing monoclonal antibody against ANGPTL4 binds to a peptide having the sequence of SEQ ID NO: 40. In certain embodiments, a neutralizing monoclonal antibody against ANGPTL4 binds to a peptide having the sequence of SEQ ID NO: 41. In certain embodiments, a neutralizing monoclonal antibody against ANGPTL4 binds to a peptide having the sequence of SEQ ID NO: 43. In certain embodiments, a neutralizing monoclonal antibody against ANGPTL4 binds to both a peptide having the sequence of SEQ ID NO: 41 and a peptide having the sequence of SEQ ID NO: 43.

In certain embodiments, neutralizing monoclonal antibodies are provided that bind to the same epitope to which monoclonal antibody 14D12 binds. In certain embodiments, neutralizing monoclonal antibodies are provided that bind to the same epitope to which monoclonal antibody 15F2 binds. In certain embodiments, neutralizing monoclonal antibodies are provided that bind to the same epitope to which monoclonal antibody 90B4 binds.

Certain neutralizing antibodies comprise a heavy chain comprising an amino acid sequence as set forth in SEQ ID NO: 12. Certain neutralizing antibodies comprise a heavy chain comprising an amino acid sequence as set forth in SEQ ID NO: 13. Certain neutralizing antibodies comprise a heavy chain comprising an amino acid sequence as set forth in SEQ ID NO: 14. Certain neutralizing antibodies comprise a light chain comprising an amino acid sequence as set forth in SEQ ID NO: 16. Certain neutralizing antibodies comprise a light chain comprising an amino acid sequence as set forth in SEQ ID NO: 17. Certain neutralizing antibodies comprise a light chain comprising an amino acid sequence as set forth in SEQ ID NO: 18.

Certain neutralizing antibodies comprise a heavy chain comprising an amino acid sequence as set forth in SEQ ID NO: 12 and a light chain comprising an amino acid sequence as set forth in SEQ ID NO: 16. Certain neutralizing antibodies comprise a heavy chain comprising an amino acid sequence as set forth in SEQ ID NO: 13 and a light chain comprising an amino acid sequence as set forth in SEQ ID NO: 17. Certain neutralizing antibodies comprise a heavy chain comprising an amino acid sequence as set forth in SEQ ID NO: 14 and a light chain comprising an amino acid sequence as set forth in SEQ ID NO: 18.

1. Chimerized and Humanized Monoclonal Antibodies

In certain embodiments, non-human antibodies are chimerized. In certain embodiments, mouse monoclonal antibodies that specifically bind human ANGPTL4 are chimerized. Certain exemplary methods for making chimeric antibodies are provided, for example, in Morrison et al. (1984) *Proc. Nat'l Acad. Sci. USA* 81:6851-6855; Neuberger et al. (1984) *Nature* 312:604-608; Takeda et al. (1985) *Nature* 314:452-454; and U.S. Pat. Nos. 6,075,181 and 5,877,397.

In certain embodiments, non-human antibodies are "humanized." In certain embodiments, mouse monoclonal antibodies that specifically bind human ANGPTL4 are humanized. In certain embodiments, mouse monoclonal antibodies raised against mouse ANGPTL4, but which specifically bind (i.e., cross react) with human ANGPTL4, are humanized. In certain embodiments, humanized antibodies retain their binding specificity and have reduced immunogenicity (e.g., reduced human anti-mouse antibody (HAMA) response) when administered to a human. In certain embodiments, humanization is achieved by methods including, but not limited to, CDR grafting and human engineering, as described in detail below.

In certain embodiments of humanized antibodies, one or more complementarity determining regions (CDRs) from the light and heavy chain variable regions of an antibody with the desired binding specificity (the "donor" antibody) are grafted onto human framework regions (FRs) in an "acceptor" antibody. Exemplary CDR grafting is described, e.g., in U.S. Pat. Nos. 6,180,370, 5,693,762, 5,693,761, 5,585,089, and 5,530,101; Queen et al. (1989) *Proc. Nat'l Acad. Sci. USA* 86:10029-10033. In certain embodiments, one or more CDRs from the light and heavy chain variable regions are grafted onto consensus human FRs in an acceptor antibody. To create consensus human FRs, in certain embodiments, FRs from several human heavy chain or light chain amino acid sequences are aligned to identify a consensus amino acid sequence.

In certain embodiments, certain FR amino acids in the acceptor antibody are replaced with FR amino acids from the donor antibody. In certain such embodiments, FR amino acids from the donor antibody are amino acids that contribute to the affinity of the donor antibody for the target antigen. See, e.g., in U.S. Pat. Nos. 6,180,370, 5,693,762, 5,693,761, 5,585,089, and 5,530,101; Queen et al. (1989) *Proc. Nat'l Acad. Sci. USA* 86:10029-10033. In certain embodiments, computer programs are used for modeling donor and/or acceptor antibodies to identify residues that are likely to be involved in binding antigen and/or to contribute to the structure of the antigen binding site, thus assisting in the selection of residues, such as FR residues, to be replaced in the donor antibody.

In certain embodiments, CDRs from a donor antibody are grafted onto an acceptor antibody comprising a human constant region. In certain such embodiments, FRs are also grafted onto the acceptor. In certain embodiments, CDRs from a donor antibody are derived from a single chain Fv antibody. In certain embodiments, FRs from a donor antibody are derived from a single chain Fv antibody. In certain embodiments, grafted CDRs in a humanized antibody are further modified (e.g., by amino acid substitutions, deletions, or insertions) to increase the affinity of the humanized antibody for the target antigen. In certain embodiments, grafted FRs in a humanized antibody are further modified (e.g., by amino acid substitutions, deletions, or insertions) to increase the affinity of the humanized antibody for the target antigen.

In certain embodiments, non-human antibodies may be humanized using a "human engineering" method. See, e.g., U.S. Pat. Nos. 5,766,886 and 5,869,619. In certain embodiments of human engineering, information on the structure of antibody variable domains (e.g., information obtained from crystal structures and/or molecular modeling) is used to assess the likelihood that a given amino acid residue in a variable region is (a) involved in antigen binding, (b) exposed on the antibody surface (i.e., accessible to solvent), or (c) buried within the antibody variable region (i.e., involved in maintaining the structure of the variable region). Furthermore, in certain embodiments, human variable region consensus sequences are generated to identify residues that are conserved among human variable regions. In certain embodiments, that information provides guidance as to whether an amino acid residue in the variable region of a non-human antibody should be substituted.

Certain neutralizing antibodies comprise a heavy chain comprising CDR1, CDR2, and CDR3 of 14D12. Certain neutralizing antibodies comprise a heavy chain comprising CDR1, CDR2, and CDR3 of 15F2. Certain neutralizing antibodies comprise a heavy chain comprising CDR1, CDR2, and CDR3 of 90B4. Certain neutralizing antibodies comprise a heavy chain comprising at least one CDR of 14D12. Certain neutralizing antibodies comprise a heavy chain comprising at least one CDR of 15F2. Certain neutralizing antibodies comprise a heavy chain comprising at least one CDR of 90B4. Certain neutralizing antibodies comprise a heavy chain comprising at least two CDRs of 14D12. Certain neutralizing antibodies comprise a heavy chain comprising at least two CDRs of 15F2. Certain neutralizing antibodies comprise a heavy chain comprising at least two CDRs of 90B4.

Certain neutralizing antibodies comprise a light chain comprising CDR1, CDR2, and CDR3 of 14D12. Certain neutralizing antibodies comprise a light chain comprising CDR1, CDR2, and CDR3 of 15F2. Certain neutralizing antibodies comprise a light chain comprising CDR1, CDR2, and CDR3 of 90B4. Certain neutralizing antibodies comprise a light chain comprising at least one CDR of 14D12. Certain neutralizing antibodies comprise a light chain comprising at least one CDR of 15F2. Certain neutralizing antibodies comprise a light chain comprising at least one CDR of 90B4. Certain neutralizing antibodies comprise a light chain comprising at least two CDRs of 14D12. Certain neutralizing antibodies comprise a light chain comprising at least two CDRs of 15F2. Certain neutralizing antibodies comprise a light chain comprising at least two CDRs of 90B4.

2. Antibody Isotypes

In certain embodiments, an antibody against ANGPTL4 is of any isotype selected from IgM, IgD, IgG, IgA, and IgE. In certain embodiments, an antibody against ANGPTL4 is of the IgG isotype. In certain such embodiments, an antibody is of the subclass IgG1, IgG2, IgG3, or IgG4. In certain embodiments, an antibody against ANGPTL4 is of the IgM isotype. In certain such embodiments, an antibody is of the subclass IgM1 or IgM2. In certain embodiments, an antibody against ANGPTL4 is of the IgA isotype. In certain such embodiments, an antibody is of the subclass IgA1 or IgA2. In certain embodiments, an antibody against ANGPTL4 comprises a human kappa light chain and a human IgG1 or IgG2 heavy chain. In certain embodiments, an antibody against ANGPTL4 comprises a mouse kappa light chain and a mouse IgG1 or IgG2 heavy chain.

3. Modified Antibodies

In various embodiments, an antibody is modified to alter one or more of its properties. In certain embodiments, a modified antibody may possess advantages over an unmodified antibody, such as increased stability, increased time in circulation, or decreased immunogenicity (see, e.g., U.S. Pat. No. 4,179,337). In certain embodiments, an antibody is modified by linking it to a nonproteinaceous moiety. In certain embodiments, an antibody is modified by altering the glycosylation state of the antibody, e.g., by altering the number, type, linkage, and/or position of carbohydrate chains on the antibody. In certain embodiments, an antibody is altered so that it is not glycosylated.

In certain embodiments, one or more chemical moieties are linked to the amino acid backbone and/or carbohydrate residues of the antibody. Certain exemplary methods for linking a chemical moiety to an antibody are known to those skilled in the art. Such methods include, but are not limited to, acylation reactions or alkylation reactions. See, for example, EP 0 401 384; Malik et al. (1992), *Exp. Hematol.*, 20:1028-1035; Francis (1992), *Focus on Growth Factors*, 3(2):4-10, published by Mediscript, Mountain Court, Friern Barnet Lane, London N20 OLD, UK; EP 0 154 316; EP 0 401 384; WO 92/16221; WO 95/34326; WO 95/13312; WO 96/11953; WO 96/19459 and WO 96/19459. In certain embodiments, any of these reactions are used to generate an antibody that is chemically modified at its amino-terminus.

In certain embodiments, an antibody is linked to a detectable label, such as an enzymatic, fluorescent, isotopic or affinity label. In certain such embodiments, a detectable label allows for the detection or isolation of the antibody. In certain embodiments, a detectable label allows for the detection of an antigen bound by the antibody.

In certain embodiments, an antibody is modified by linking it to one or more polymers. In certain embodiments, an antibody is linked to one or more water-soluble polymers. In certain such embodiments, linkage to a water-soluble polymer reduces the likelihood that the antibody will precipitate in an aqueous environment, such as a physiological environment. In certain embodiments, a therapeutic antibody is linked to a water-soluble polymer. In certain embodiments, one skilled in the art can select a suitable water-soluble polymer based on considerations including, but not limited to, whether the polymer/antibody conjugate will be used in the treatment of a patient and, if so, the pharmacological profile of the antibody (e.g., half-life, dosage, activity, antigenicity, and/or other factors).

Certain exemplary clinically acceptable, water-soluble polymers include, but are not limited to, polyethylene glycol (PEG); polyethylene glycol propionaldehyde; copolymers of ethylene glycol/propylene glycol; monomethoxy-polyethylene glycol; carboxymethylcellulose; dextran; polyvinyl alcohol (PVA); polyvinyl pyrrolidone, poly-1,3-dioxolane; poly-1,3,6-trioxane; ethylene/maleic anhydride copolymer; poly-β-amino acids (either homopolymers or random copolymers); poly(n-vinyl pyrrolidone)polyethylene glycol; polypropylene glycol homopolymers (PPG) and other polyalkylene oxides; polypropylene oxide/ethylene oxide copolymers; polyoxyethylated polyols (POG) (e.g., glycerol) and other polyoxyethylated polyols; polyoxyethylated sorbitol, polyoxyethylated glucose, colonic acids or other carbohydrate polymers; and Ficoll, dextran, or mixtures thereof. Certain exemplary PEGs include, but are not limited to, certain forms known in the art to be useful in antibody modification, such as mono-($C_1$-$C_{10}$) alkoxy- or aryloxy-PEG. In certain embodiments, PEG propionaldehyde may have advantages in manufacturing due to its stability in water.

In certain embodiments, a water-soluble polymer is of any molecular weight. In certain embodiments, a water-soluble polymer is branched or unbranched. In certain embodiments, a water-soluble polymer has an average molecular weight of about 2 kDa to about 100 kDa, including all points between the end points of the range. In certain embodiments, a water-soluble polymer has an average molecular weight of about 5 kDa to about 40 kDa. In certain embodiments, a water-soluble polymer has an average molecular weight of about 10 kDa to about 35 kDa. In certain embodiments, a water-soluble polymer has an average molecular weight of about 15 kDa to about 30 kDa.

In certain embodiments, an antibody is linked to PEG (i.e., an antibody is "pegylated"). In various embodiments, PEG has low toxicity in mammals. See Carpenter et al. (1971) *Toxicol. Appl. Pharmacol.*, 18, 35-40. Notably, a PEG adduct of adenosine deaminase was approved in the United States for use in humans for the treatment of severe combined immunodeficiency syndrome. In various embodiments, PEG may reduce the immunogenicity of antibodies. For example, in certain embodiments, linkage of PEG to an antibody having non-human sequences may reduce the antigenicity of that antibody when administered to a human.

In certain embodiments, a polymer is linked to one or more reactive amino acid residues in an antibody. Certain exemplary reactive amino acid residues include, but are not limited to, the alpha-amino group of the amino-terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, and activated glycosyl chains linked to certain asparagine, serine or threonine residues. Certain exemplary activated forms of PEG ("PEG reagents") suitable for direct reaction with proteins are known to those skilled in the art. For example, in certain embodiments, PEG reagents suitable for linkage to amino groups include, but are not limited to, active esters of carboxylic acid or carbonate derivatives of PEG, for example, those in which the leaving groups are N-hydroxysuccinimide, p-nitrophenol, imidazole or 1-hydroxy-2-nitrobenzene-4-sulfonate. In certain embodiments, PEG reagents containing maleimido or haloacetyl groups are used to modify sulfhydryl groups. In certain embodiments, PEG reagents containing amino, hydrazine and/or hydrazide groups may be used in reactions with aldehydes generated by periodate oxidation of carbohydrate groups in proteins.

In certain embodiments, a water-soluble polymer has at least one reactive group. In certain embodiments, an activated derivative of a water-soluble polymer, such as PEG, is created by reacting the water-soluble polymer with an activating group. In certain embodiments, an activating group may be monofunctional, bifunctional, or multifunctional. Certain exemplary activating groups that can be used to link a water-soluble polymer to two or more antibodies include, but are not limited to, the following groups: sulfone (e.g., chlorosulfone, vinylsulfone and divinylsulfone), maleimide, sulfhydryl, thiol, triflate, tresylate, azidirine, oxirane and 5-pyridyl. In certain embodiments, a PEG derivative is typically stable against hydrolysis for extended periods in aqueous environments at pHs of about 11 or less. In certain embodiments, a PEG derivative linked to another molecule, such as an antibody, confers stability from hydrolysis on that molecule. Certain exemplary homobifunctional PEG derivatives include, but are not limited to, PEG-bis-chlorosulfone and PEG-bis-vinylsulfone (see WO 95/13312).

D. CERTAIN METHODS OF MAKING MONOCLONAL ANTIBODIES

1. Certain Hybridoma Methods

In certain embodiments, monoclonal antibodies are produced by standard techniques. In certain embodiments, monoclonal antibodies are produced by hybridoma-based methods. Certain such methods are known to those skilled in the art. See, e.g., Kohler et al. (1975) *Nature* 256:495-497; Harlow and Lane (1988) *Antibodies: A Laboratory Manual* Ch. 6 (Cold Spring Harbor Laboratory, Cold Spring Harbor, N.Y.). In certain such embodiments, a suitable animal, such as a mouse, rat, hamster, monkey, or other mammal, is immunized with an immunogen to produce antibody-secreting cells. In certain embodiments, the antibody-secreting cells are B-cells, such as lymphocytes or splenocytes. In certain embodiments, lymphocytes (e.g., human lymphocytes) are immunized in vitro to generate antibody-secreting cells. See, e.g., Borreback et al. (1988) *Proc. Nat'l Acad. Sci. USA* 85:3995-3999.

In certain embodiments, antibody secreting cells are fused with an "immortalized" cell line, such as a myeloid-type cell line, to produce hybridoma cells. In certain embodiments, hybridoma cells that produce the desired antibodies are identified, for example, by ELISA. In certain embodiments, such cells can then be subcloned and cultured using standard methods. In certain embodiments, such cells can also be grown in vivo as ascites tumors in a suitable animal host. In certain embodiments, monoclonal antibodies are isolated from hybridoma culture medium, serum, or ascites fluid using standard separation procedures, such as affinity chromatography. Guidance for the production of hybridomas and the purification of monoclonal antibodies according to certain embodiments is provided, for example, in Harlow and Lane (1988) *Antibodies: A Laboratory Manual* Ch. 8 (Cold Spring Harbor Laboratory, Cold Spring Harbor, N.Y.).

In certain embodiments, mouse monoclonal antibodies are produced by immunizing genetically altered mice with an immunogen. In certain such embodiments, the mice are ANGPTL4-deficient mice, which partially or completely lack ANGPTL4 function. In certain such embodiments, the mice are "knockout" mice that lack all or part of a gene encoding ANGPTL4. In certain embodiments, such knockout mice are immunized with mouse ANGPTL4. In certain embodiments, such knockout mice are immunized with human ANGPTL4.

In certain embodiments, human monoclonal antibodies are raised in transgenic animals (e.g., mice) that are capable of producing human antibodies. See, e.g., U.S. Pat. Nos. 6,075, 181 A and 6,114,598 A; and WO 98/24893 A2. For example, in certain embodiments, human immunoglobulin genes are introduced (e.g., using yeast artificial chromosomes, human chromosome fragments, or germline integration) into mice in which the endogenous Ig genes have been inactivated. See, e.g., Jakobovits et al. (1993) *Nature* 362:255-258; Tomizuka et al. (2000) *Proc. Nat'l Acad. Sci. USA* 97:722-727; and Mendez et al. (1997) *Nat. Genet.* 15:146-156 (describing the XenoMouse II® line of transgenic mice).

In certain embodiments, such transgenic mice are immunized with an immunogen. In certain such embodiments, lymphatic cells (such as B-cells) from mice that express antibodies are obtained. In certain such embodiments, such recovered cells are fused with an "immortalized" cell line, such as a myeloid-type cell line, to produce hybridoma cells.

In certain such embodiments, hybridoma cells are screened and selected to identify those that produce antibodies specific to the antigen of interest. Certain exemplary methods and transgenic mice suitable for the production of human monoclonal antibodies are described, e.g., in Jakobovits et al. (1993) *Nature* 362:255-258; Jakobovits (1995) *Curr. Opin. Biotechnol.* 6:561-566; Lonberg et al. (1995) *Int. Rev. Immunol.* 13:65-93; Fishwild et al. (1996) *Nat. Biotechnol.* 14:845-851; Mendez et al. (1997) *Nat. Genet.* 15:146-156; Green (1999) *J. Immunol. Methods* 231:11-23; Tomizuka et al. (2000) *Proc. Nat'l Acad. Sci. USA* 97:722-727; and reviewed in Little et al. (2000) *Immunol. Today* 21:364-370; and WO 98/24893. In certain embodiments, human monoclonal antibodies against ANGPTL4 are suitable for use as therapeutic antibodies. See Part V.G., below.

2. Certain Display-Based Methods

In certain embodiments, human monoclonal antibodies are produced using a display-based method, such as, for example, any of those described below.

In certain embodiments, a monoclonal antibody is produced using phage display techniques. Certain exemplary antibody phage display methods are known to those skilled in the art and are described, for example, in Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.). For example, in certain embodiments, a library of antibodies are displayed on the surface of a filamentous phage, such as the nonlytic filamentous phage fd or M13. In certain embodiments, the antibodies are antibody fragments, such as scFvs, Fabs, Fvs with an engineered intermolecular disulfide bond to stabilize the $V_H$-$V_L$ pair, and diabodies. In certain embodiments, antibodies with the desired binding specificity can then be selected. Certain exemplary embodiments of antibody phage display methods are described in further detail below.

In certain embodiments, an antibody phage-display library can be prepared using certain methods known to those skilled in the art. See, e.g., Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.). In certain embodiments, variable gene repertoires are prepared by PCR amplification of genomic DNA or cDNA derived from the mRNA of antibody-secreting cells. For example, in certain embodiments, cDNA is prepared from mRNA of B-cells. In certain embodiments, cDNA encoding the variable regions of heavy and light chains is amplified, for example, by PCR.

In certain embodiments, heavy chain cDNA and light chain cDNA are cloned into a suitable vector. In certain embodiments, heavy chain cDNA and light chain cDNA are randomly combined during the cloning process, thereby resulting in the assembly of a cDNA library encoding diverse scFvs or Fabs. In certain embodiments, heavy chain cDNA and light chain cDNA are ligated before being cloned into a suitable vector. In certain embodiments, heavy chain cDNA and light chain cDNA are ligated by stepwise cloning into a suitable vector.

In certain embodiments, cDNA is cloned into a phage display vector, such as a phagemid vector. Certain exemplary phagemid vectors, such as pCES1, are known to those skilled in the art. In certain embodiments, cDNA encoding both heavy and light chains is present on the same vector. For example, in certain embodiments, cDNA encoding scFvs are cloned in frame with all or a portion of gene III, which encodes the minor phage coat protein pIII. In certain such embodiments, the phagemid directs the expression of the scFv-pIII fusion on the phage surface. Alternatively, in certain embodiments, cDNA encoding heavy chain (or light chain) is cloned in frame with all or a portion of gene III, and cDNA encoding light chain (or heavy chain) is cloned downstream of a signal sequence in the same vector. The signal sequence directs expression of the light chain (or heavy chain) into the periplasm of the host cell, where the heavy and light chains assemble into Fab fragments. Alternatively, in certain embodiments, cDNA encoding heavy chain and cDNA encoding light chain are present on separate vectors. In certain such embodiments, heavy chain and light chain cDNA is cloned separately, one into a phagemid and the other into a phage vector, which both contain signals for in vivo recombination in the host cell.

In certain embodiments, recombinant phagemid or phage vectors are introduced into a suitable bacterial host, such as *E. coli*. In certain embodiments using phagemid, the host is infected with helper phage to supply phage structural proteins, thereby allowing expression of phage particles carrying the antibody-pIII fusion protein on the phage surface.

In certain embodiments, "synthetic" antibody libraries are constructed using repertoires of variable genes that are rearranged in vitro. For example, in certain embodiments, individual gene segments encoding heavy or light chains (V-D-J or V-J, respectively) are randomly combined using PCR. In certain such embodiments, additional sequence diversity can be introduced into the CDRs, and possibly FRs, e.g., by error prone PCR. In certain such embodiments, additional sequence diversity is introduced into CDR3, e.g., H3 of the heavy chain.

In certain embodiments, "naïve" or "universal" phage display libraries are constructed as described above using nucleic acid from an unimmunized animal. In certain embodiments, the unimmunized animal is a human. In certain embodiments, "immunized" phage display libraries are constructed as described above using nucleic acid from an immunized animal. In certain embodiments, the immunized animal is a human, rat, mouse, hamster, or monkey. In certain such embodiments, the animals are immunized with any of the immunogens described below.

Certain exemplary universal human antibody phage display libraries are available from commercial sources. Certain exemplary libraries include, but are not limited to, the HuCAL® series of libraries from MorphoSys AG (Martinstreid/Munich, Germany); libraries from Crucell (Leiden, the Netherlands) using MAbstract® technology; the n-CoDeR™ Fab library from BioInvent (Lund, Sweden); and libraries available from Cambridge Antibody Technology (Cambridge, UK).

In certain embodiments, the selection of antibodies having the desired binding specificity from a phage display library is achieved by successive panning steps. In certain embodiments of panning, library phage preparations are exposed to antigen. In certain such embodiments, the phage-antigen complexes are washed, and unbound phage are discarded. In certain such embodiments, bound phage are recovered and subsequently amplified by infecting *E. coli*. In certain such embodiments, monoclonal antibody-producing phage may be cloned by picking single plaques. In certain embodiments, the above process is repeated.

In certain embodiments, the antigen used in panning is any of the immunogens described below. In certain embodiments, the antigen is immobilized on a solid support to allow purification of antigen-binding phage by affinity chromatography. In certain embodiments, the antigen is biotinylated, thereby allowing the separation of bound phage from unbound phage using streptavidin-coated magnetic beads. In certain embodiments, the antigen may be immobilized on cells (for direct panning), in tissue cryosections, or on membranes (e.g., nylon or nitrocellulose membranes). Other variations of certain panning procedures may be routinely determined by one skilled in the art.

In certain embodiments, a yeast display system is used to produce monoclonal antibodies. In certain such systems, an antibody is expressed as a fusion protein with all or a portion of the yeast AGA2 protein, which becomes displayed on the surface of the yeast cell wall. In certain such embodiments, yeast cells expressing antibodies with the desired binding specificity can then be identified by exposing the cells to fluorescently labeled antigen. In certain such embodiments, yeast cells that bind the antigen can then be isolated by flow cytometry. See, e.g., Boder et al. (1997) *Nat. Biotechnol.* 15:553-557.

3. Certain Affinity Maturation Methods

In certain embodiments, the affinity of an antibody for a particular antigen is increased by subjecting the antibody to affinity maturation (or "directed evolution") in vitro. In vivo, native antibodies undergo affinity maturation through somatic hypermutation followed by selection. Certain in vitro methods mimic that in vivo process, thereby allowing the production of antibodies having affinities that equal or surpass that of native antibodies.

In certain embodiments of affinity maturation, mutations are introduced into a nucleic acid sequence encoding the variable region of an antibody having the desired binding specificity. See, e.g., Hudson et al. (2003) *Nature Med.* 9:129-134; Brekke et al. (2002) *Nature Reviews* 2:52-62. In certain embodiments, mutations are introduced into the variable region of the heavy chain, light chain, or both. In certain embodiments, mutations are introduced into one or more CDRs. In certain such embodiments, mutations are introduced into H3, L3, or both. In certain embodiments, mutations are introduced into one or more FRs. In certain embodiments, a library of mutations is created, for example, in a phage, ribosome, or yeast display library, so that antibodies with increased affinity may be identified by standard screening methods. See, e.g., Boder et al. (2000) *Proc. Nat'l Acad. Sci. USA* 97:10701-10705; Foote et al. (2000) *Proc. Nat'l Acad. Sci. USA* 97:10679-10681; Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.); and Hanes et al. (1998) *Proc. Nat'l Acad. Sci. USA* 95:14130-14135.

In certain embodiments, mutations are introduced by site-specific mutagenesis based on information on the antibody's structure, e.g., the antigen binding site. In certain embodiments, mutations are introduced using combinatorial mutagenesis of CDRs. In certain embodiments, all or a portion of the variable region coding sequence is randomly mutagenized, e.g., using *E. coli* mutator cells, homologous gene rearrangement, or error prone PCR. In certain embodiments, mutations are introduced using "DNA shuffling." See, e.g., Crameri et al. (1996) *Nature Med.* 2:100-102; Fermer et al. (2004) *Tumor Biology* 25:7-13.

In certain embodiments, "chain shuffling" is used to generate antibodies with increased affinity. In certain embodiments of chain shuffling, one of the chains, e.g., the light chain, is replaced with a repertoire of light chains, while the other chain, e.g., the heavy chain, is unchanged, thus providing specificity. In certain such embodiments, a library of chain shuffled antibodies is created, wherein the unchanged heavy chain is expressed in combination with each light chain from the repertoire of light chains. In certain embodiments, such libraries may then be screened for antibodies with increased affinity. In certain embodiments, both the heavy and light chains are sequentially replaced. In certain embodiments, only the variable regions of the heavy and/or light chains are replaced. In certain embodiments, only a portion of the variable regions, e.g., CDRs, of the heavy and/or light chains are replaced. See, e.g., Hudson et al. (2003) *Nature Med.* 9:129-134; Brekke et al. (2002) *Nature Reviews* 2:52-62; Kang et al. (1991) *Proc. Nat'l Acad. Sci. USA* 88:11120-11123; Marks et al. (1992) *Biotechnology* 10:779-83.

In certain embodiments, mouse monoclonal antibodies that specifically bind human ANGPTL4 (including, but not limited to, mouse monoclonal antibodies raised against mouse ANGPTL4 but which specifically bind (i.e., cross react) with human ANGPTL4) are subject to sequential chain shuffling. In certain embodiments, for example, the heavy chain of a given mouse monoclonal antibody is combined with a new repertoire of human light chains, and antibodies with the desired affinity are selected. In certain such embodiments, the light chains of the selected antibodies are then combined with a new repertoire of human heavy chains, and antibodies with the desired affinity are selected. Thus, in certain embodiments, human antibodies having the desired antigen binding specificity and affinity are selected.

Alternatively, in certain embodiments, the heavy chain of a given mouse monoclonal antibody is combined with a new repertoire of human light chains, and antibodies with the desired affinity are selected from this first round of shuffling. In certain embodiments, the light chain of the original mouse monoclonal antibody is combined with a new repertoire of human heavy chains, and antibodies with the desired affinity are selected from this second round of shuffling. In certain embodiments, human light chains from the antibodies selected in the first round of shuffling are then combined with human heavy chains from the antibodies selected in the second round of shuffling. Thus, in certain embodiments, human antibodies having the desired antigen binding specificity and affinity are selected.

In certain embodiments, a "ribosome display" method is used that alternates antibody selection with affinity maturation. In certain embodiments of a ribosome display method, antibody-encoding nucleic acid is amplified by RT-PCR between the selection steps. Thus, in certain embodiments, error prone polymerases may be used to introduce mutations into the nucleic acid. A nonlimiting example of such a method is described in detail in Hanes et al. (1998) *Proc. Nat'l Acad. Sci. USA* 95:14130-14135.

4. Certain Recombinant Methods

In certain embodiments, a monoclonal antibody is produced by recombinant techniques. See, e.g., U.S. Pat. No. 4,816,567. In certain such embodiments, nucleic acid encoding monoclonal antibody chains are cloned and expressed in a suitable host cell. For example, in certain embodiments, RNA can be prepared from cells expressing the desired antibody, such as mature B-cells or hybridoma cells, using standard methods. In certain embodiments, the RNA can then be used to make cDNA using standard methods. In certain embodiments, cDNA encoding a heavy or light chain polypeptide is amplified, for example, by PCR, using specific oligonucleotide primers. In certain embodiments, the cDNA is cloned into a suitable expression vector. In certain embodiments, the expression vector is then transformed or transfected into a suitable host cell, such as a host cell that does not endogenously produce antibody. Certain exemplary host cells include, but are not limited to, *E. coli*, COS cells, Chinese hamster ovary (CHO) cells, and myeloma cells. In certain embodiments, wherein heavy and light chains are coexpressed in the same host, reconstituted antibody may be isolated.

In certain embodiments, cDNA encoding a heavy or light chain can be modified. For example, in certain embodiments, the constant region of a mouse heavy or light chain can be replaced with the constant region of a human heavy or light chain. In this manner, in certain embodiments, a chimeric antibody can be produced which possesses human antibody constant regions but retains the binding specificity of a mouse antibody.

In certain embodiments, recombinant antibodies can be expressed in certain cell lines. In certain embodiments, sequences encoding particular antibodies can be used for transformation of a suitable mammalian host cell. According to certain embodiments, transformation can be by any known method for introducing polynucleotides into a host cell. Certain exemplary methods include, but are not limited to, packaging the polynucleotide in a virus (or into a viral vector) and transducing a host cell with the virus (or vector) and using certain transfection procedures known in the art, as exemplified by U.S. Pat. Nos. 4,399,216, 4,912,040, 4,740,461, and 4,959,455. In certain embodiments, the transformation procedure used may depend upon the host to be transformed. Certain exemplary methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Certain exemplary mammalian cell lines available as hosts for expression are known in the art and include, but are not limited to, many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected by determining which cell lines produce high levels of antibodies that specifically bind ANGPTL4.

E. CERTAIN POLYPEPTIDE IMMUNOGENS

In certain embodiments, to generate antibodies, an animal is immunized with an immunogen. In certain embodiments, an immunogen is a polypeptide comprising ANGPTL4. In certain embodiments, an immunogen is a polypeptide comprising a fragment of ANGPTL4. In certain embodiments, an immunogen is a polypeptide comprising the N-terminal coiled-coil domain of ANGPTL4.

In certain embodiments, an immunogen comprises a mouse ANGPTL4. In certain embodiments, an immunogen comprises a mouse ANGPTL4 comprising the amino acid sequence of SEQ ID NO: 1. In certain embodiments, an immunogen comprises a mouse ANGPTL4 comprising the amino acid sequence of SEQ ID NO: 50. In certain embodiments, an immunogen comprises a fragment of mouse ANGPTL4. In certain embodiments, an immunogen comprises a fragment of SEQ ID NO: 1 from residue 21 to residue 174. In certain embodiments, an immunogen comprises a fragment of SEQ ID NO: 50 from residue 21 to residue 174. In certain embodiments, an immunogen comprises any peptide of about 10-20 contiguous amino acids from residue 21 to residue 174 of SEQ ID NO: 1. In certain embodiments, an immunogen comprises any peptide of about 10-20 contiguous amino acids from residue 21 to residue 174 of SEQ ID NO: 50. In certain embodiments, an immunogen comprises a peptide selected from any of SEQ ID NOs: 40 to 48. In certain embodiments, an immunogen comprises a peptide selected from SEQ ID NOs: 40, 41, 42, and 43. In certain embodiments, an immunogen comprises a peptide comprising one or more amino acid sequences selected from SEQ ID NOs: 40, 41, 42, and 43. In certain embodiments, an immunogen comprises a peptide comprising SEQ ID NOs: 41, 42, and 43. In certain such embodiments, a peptide is selected that is likely to be immunogenic. In certain such embodiments, a peptide is selected that is predicted to be hydrophilic and/or likely to be exposed on the surface of native mouse ANGPTL4 in its folded state. Exemplary guidance for selecting suitable immunogenic peptides is provided, for example, in Ausubel et al. (1989) *Current Protocols in Molecular Biology* Ch. 11.14 (John Wiley & Sons, NY); and Harlow and Lane (1988) *Antibodies: A Laboratory Manual* Ch. (Cold Spring Harbor Laboratory, Cold Spring Harbor, N.Y.).

Certain exemplary algorithms are known to those skilled in the art for predicting whether a peptide segment of a protein is hydrophilic and therefore likely to be exposed on the surface of the protein. Certain such algorithms use the primary sequence information of a protein to make such predictions. Certain such algorithms are based on the method of, for example, Hopp and Woods (1981) *Proc. Nat'l Acad. Sci. USA* 78:3824-3828, or Kyte and Doolittle (1982) *J. Mol. Biol.* 157:105-132. Certain exemplary algorithms are known to those skilled in the art for predicting the secondary structure of a protein based on the primary amino acid sequence of the protein. See, e.g., Corrigan et al. (1982) *Comput. Programs Biomed.* 3:163-168. Certain such algorithms are based on the method of, for example, Chou and Fasman (1978) *Ann. Rev. Biochem.* 47:25-276. In certain embodiments, peptide segments that are predicted to form β-turns, and are therefore likely to be exposed on the surface of a protein, may be selected as immunogens.

In certain embodiments, an immunogen comprises a human ANGPTL4. In certain embodiments, an immunogen comprises a human ANGPTL4 comprising the amino acid sequence of SEQ ID NO:2. In certain embodiments, an immunogen comprises a fragment of SEQ ID NO:2 from residue 21 to residue 169. In certain embodiments, an immunogen comprises any peptide of about 10-20 contiguous amino acids from residue 21 to residue 169 of SEQ ID NO:2. In certain such embodiments, a peptide is selected that is likely to be immunogenic. In certain such embodiments, a peptide is selected that is predicted to be hydrophilic and/or likely to be exposed on the surface of native human ANGPTL4 in its folded state. Exemplary guidance for selecting suitable immunogenic peptides is provided, for example, in Ausubel et al. (1989) *Current Protocols in Molecular Biology Ch.* 11.14 (John Wiley & Sons, NY); and Harlow and Lane (1988) *Antibodies: A Laboratory Manual Ch.* 5 (Cold Spring Harbor Laboratory, Cold Spring Harbor, N.Y.).

In certain embodiments, an animal is immunized with an immunogen and one or more adjuvants. In certain embodiments, an adjuvant is used to increase the immunological response, depending on the host species. Certain exemplary adjuvants include, but are not limited to, Freund's adjuvant (complete and incomplete), mineral salts such as aluminum hydroxide or aluminum phosphate, surface active substances, chitosan, lysolecithin, pluronic polyols, polyanions, peptides, oil emulsions, and potentially useful human adjuvants such as BCG (bacille Calmette-Guerin) and *Corynebacterium parvum*. In certain embodiments, the immune response to an immunogen, e.g., a peptide immunogen, is enhanced by coupling the immunogen to another immunogenic molecule or "carrier protein." Certain exemplary carrier proteins include, but are not limited to, keyhole limpet hemocyanin (KLH), tetanus toxoid, diphtheria toxoid, ovalbumin, cholera toxoid, and immunogenic fragments thereof. For exemplary guidance in coupling peptide immunogens to carrier proteins, see, e.g., Ausubel et al. (1989) *Current Protocols in Molecular Biology* Ch. 11.15 (John Wiley & Sons, NY); and Harlow and Lane (1988) *Antibodies: A Laboratory Manual* Ch. 5 (Cold Spring Harbor Laboratory, Cold Spring Harbor, N.Y.).

In certain embodiments, any of the above immunogens can be produced using standard recombinant methods. For example, in certain embodiments, a polynucleotide encoding a mouse or human ANGPTL4 or a fragment of that polynucleotide may be cloned into a suitable expression vector. In certain embodiments, the polynucleotide comprises the nucleic acid sequence of SEQ ID NO:3 or SEQ ID NO:4. In certain embodiments, the recombinant vector is then introduced into a suitable host cell. In certain embodiments, the polypeptide is then isolated from the host cell by standard methods. For certain exemplary methods of recombinant protein expression, see, e.g., Ausubel et al. (1991) *Current Protocols in Molecular Biology* Ch. 16 (John Wiley & Sons, NY).

F. CERTAIN ASSAYS

1. Certain Binding Assays

In certain embodiments, antibodies are screened for binding to ANGPTL4 using certain routine methods that detect binding of antibody to antigen. For example, in certain embodiments, the ability of a monoclonal antibody to bind ANGPTL4 is assayed by standard immunoblotting methods, such as Western blot. See, e.g., Ausubel et al. (1992) *Current Protocols in Molecular Biology* Ch. 10.8 (John Wiley & Sons, NY); Harlow and Lane (1988) *Antibodies: A Laboratory Manual* (Cold Spring Harbor Laboratory, Cold Spring Harbor, N.Y.). In certain embodiments, ANGPTL4 to be used in such assays may be isolated or may be present in a complex mixture of proteins and/or macromolecules.

In certain embodiments, the ability of a monoclonal antibody to bind ANGPTL4 is assayed using a competitive binding assay, which evaluates the ability of a candidate antibody to compete with a known anti-ANGPTL4 antibody for binding to ANGPTL4. In certain such embodiments, the known anti-ANGPTL4 antibody is any of the monoclonal antibodies described below in Part VI.J. In certain embodiments, a competitive binding assay is performed using ELISA. See, e.g., Harlow and Lane (1988) *Antibodies: A Laboratory Manual* Ch. 14 (Cold Spring Harbor Laboratory, Cold Spring Harbor, N.Y.).

In certain embodiments, a binding assay is used to quantify the binding kinetics (e.g., rate constant) or the binding affinity (e.g., association or dissociation constant) of an antibody against ANGPTL4. In certain embodiments, the kinetics or affinity of binding is determined in the "solid-phase" by immobilizing antigen (e.g., ANGPTL4) on a solid support. The immobilized antigen "captures" antibody from solution. In certain embodiments, the kinetics or affinity of binding is determined in the "solid-phase" by immobilizing antibody (e.g., antibody against ANGPTL4) on a solid support. The immobilized antibody "captures" antigen from solution.

In certain embodiments, binding kinetics or binding affinity is determined using ELISA-based methods. In certain embodiments, binding kinetics or binding affinity is determined using biosensor-based technology, such as Biacore surface plasmon resonance technology (Biacore, Piscataway, N.J.). Certain such methods are known to those skilled in the art. See, e.g., McCafferty et al. (eds.) (1996) *Antibody Engi-*

*neering: A Practical Approach* (IRL, Oxford, UK); Goldberg et al. (1993) *Curr. Opin. Immunol.* 5:278-281; Karlsson et al. (1991) *J. Immunol. Methods* 145:229-240; Malmqvist (1993) *Curr. Opin. Immunol.* 5:282-286; for review, see Hoogenboom, *Overview of Antibody Phage-Display Technology and Its Applications*, from *Methods in Molecular Biology: Antibody Phage Display: Methods and Protocols* (2002) 178:1-37 at 19 (O'Brien and Aitken, eds., Human Press, Totowa, N.J.).

In certain embodiments, the binding kinetics or binding affinity of a Fab fragment that specifically binds to ANGPTL4 is determined. In certain instances, Fab fragments have the property of not multimerizing. Multimerization can, in certain instances, complicate the measurement of binding kinetics and binding affinity in "solid phase" methods. See, e.g., Hoogenboom, *Overview of Antibody Phage-Display Technology and Its Applications*, from *Methods in Molecular Biology: Antibody Phage Display: Methods and Protocols* (2002) 178:1-37 at 19 (O'Brien and Aitken, eds., Human Press, Totowa, N.J.). Thus, in certain embodiments, a Fab fragment that specifically binds to ANGPTL4 is suitable for use in a binding assay in which antigen is immobilized to a solid support, such as, for example, an ELISA-based assay or a Biacore assay. In certain embodiments, Fab fragments are generated from an intact antibody that specifically binds to ANGPTL4 using enzymatic methods. In certain embodiments, Fab fragments are produced by expressing nucleic acids encoding Fab fragments in a recombinant expression system, such as those described above, Part V.D.3.

In certain embodiments, the binding kinetics or binding affinity of an antibody against ANGPTL4 is determined using "solution phase" methods. In such methods, the kinetics or affinity of binding is measured for an antibody-antigen complex in solution. Certain such methods are known to those skilled in the art. A nonlimiting example of such a method is the "kinetic exclusion assay," or "KinExA." See, e.g., Blake et al. (1996) *J. Biol. Chem.* 271:27677-27685; Drake et al. (2004) *Anal. Biochem.* 328:35-43 (comparing Biacore "solid phase" and KinExA "solution phase" methods). In certain embodiments, instrumentation for performing KinExA is supplied by Sapidyne Instruments, Inc. (Boise, Id.).

In certain embodiments, the binding kinetics or binding affinity of a multivalent antibody or an antibody that multimerizes is determined using a solution phase method. In certain instances, the measurement of the binding kinetics or the binding affinity of a multivalent antibody or an antibody that multimerizes is amenable to solution phase analysis.

In certain embodiments, the binding affinity of an anti-ANGPTL4 antibody, as measured by its $K_D$, is about $10^{-6}$ M or less. In certain embodiments, the binding affinity of an anti-ANGPTL4 antibody is about $10^{-7}$ M, about $10^{-8}$ M, or about $10^{-9}$ M or less. In certain such embodiments, an anti-ANGPTL4 antibody may be used as a therapeutic antibody. See, e.g., Hudson et al. (2003) *Nature Med.* 9:129-134. In certain embodiments, binding affinities of less than $10^{-9}$ M (e.g., binding affinities from about 500 pM to about 0.5 pM, including but not limited to, binding affinities from about 100 pM to about 5 pM) are achievable, e.g., using affinity maturation techniques. See, e.g., Boder et al. (2000) *Proc. Nat'l Acad. Sci. USA* 97:10701-10705.

In certain embodiments, a monoclonal antibody that was raised against mouse ANGPTL4 is screened for specific binding to human ANGPTL4 using certain routine detection methods, e.g., such as those described herein. The ability of a monoclonal antibody to bind both mouse and human ANGPTL4 (i.e., to demonstrate "cross-reactivity") indicates the presence of the same epitope in mouse and human ANGPTL4. In certain embodiments of detection methods that use denaturing conditions (e.g., Western blot), cross-reactivity indicates that a mouse monoclonal antibody binds to the same "linear" epitope in mouse and human ANGPTL4. In certain embodiments of detection methods that use nondenaturing conditions, cross-reactivity indicates that a mouse monoclonal antibody binds to the same epitope (e.g., a linear epitope or a conformational epitope) in mouse and human ANGPTL4.

2. Certain Methods for Epitope Mapping

In various embodiments, the epitope to which a monoclonal antibody binds is identified by any of a number of assays. Certain exemplary assays are described, for example, in Morris, *Methods in Molecular Biology Vol. 66: Epitope Mapping Protocols* (1996) (Humana Press, Totowa, N.J.). For example, epitope mapping may be achieved by gene fragment expression assays or peptide-based assays. In certain embodiments of a gene fragment expression assay, for example, nucleic acids encoding fragments of ANGPTL4 are expressed in prokaryotic cells and isolated. In certain such embodiments, the ability of a monoclonal antibody to bind those fragments is then assessed, e.g., by immunoprecipitation or immunoblotting. In certain embodiments, nucleic acids encoding fragments of ANGPTL4 are transcribed and translated in vitro in the presence of radioactive amino acids. The radioactively labeled fragments of ANGPTL4 are then tested for binding to a monoclonal antibody. In certain embodiments, fragments of ANGPTL4 are generated by proteolytic fragmentation. In certain embodiments, an epitope is identified using libraries of random peptides displayed on the surface of phage or yeast. In certain embodiments, an epitope is identified by testing a library of overlapping synthetic peptide fragments of ANGPTL4 for binding to a monoclonal antibody. In certain embodiments, an epitope is identified using a competition assay, such as those described below.

3. Certain Competition Assays

In certain embodiments, monoclonal antibodies that bind to the same epitope of ANGPTL4 as a monoclonal antibody of interest are identified. In certain embodiments, such monoclonal antibodies are identified by epitope mapping, e.g., as described above. In certain embodiments, such monoclonal antibodies are identified by routine competition assays. See, e.g., Harlow and Lane (1988) *Antibodies: A Laboratory Manual* ch. 14 (Cold Spring Harbor Laboratory, Cold Spring Harbor, N.Y.). In a nonlimiting exemplary competition assay, ANGPTL4 or a fragment thereof is immobilized onto the wells of a multiwell plate. In certain such embodiments, the monoclonal antibody of interest is labeled with a fluorescent label (in certain embodiments, fluorescein isothiocyanate) by standard methods. In certain such embodiments, mixtures of the labeled monoclonal antibody of interest and an unlabeled test monoclonal antibody are added to the wells. In certain such embodiments, the fluorescence in each well is quantified to determine the extent to which the unlabeled test monoclonal antibody blocks the binding of the labeled monoclonal antibody of interest. In certain embodiments, monoclonal antibodies are deemed to share an epitope if each blocks the binding of the other by 50% or greater. Exemplary competition assays are also described, e.g., in Morris, *Methods in Molecular Biology Vol. 66: Epitope Mapping Protocols* (1996) (Humana Press, Totowa, N.J.). A nonlimiting exemplary competition assay is provided below, Part VI.O.

4. Certain Assays for Identifying Neutralizing Antibodies

In certain embodiments, monoclonal antibodies are screened for those that are neutralizing antibodies, i.e., those that reduce an activity of ANGPTL4 in vivo and/or in vitro. In certain embodiments, an activity of ANGPTL4 is the ability of ANGPTL4 to inhibit LPL. Thus, in certain embodiments, a neutralizing antibody is identified by its ability to increase LPL activity in the presence of ANGPTL4. In certain such embodiments, a neutralizing antibody increases LPL activity by at least about 20%, 30%, 40%, 50%, 60%, 70%, 80%, 90%, or 95%, relative to a control antibody. Certain exemplary assays for measuring LPL activity in vivo and in vitro are provided below, Part VI.D. and VI.I, respectively.

In certain embodiments, a neutralizing antibody that reduces an activity of ANGPTL4 in vivo is identified by its ability to decrease the level of at least one serum lipid. Certain exemplary serum lipids include, but are not limited to, triglycerides, cholesterol, and free fatty acids. In certain such embodiments, a neutralizing antibody decreases the level of at least one serum lipid by at least about 10%, 20%, 30%, 40%, 50%, 60%, 70%, 80%, 90%, or 95%, relative to a control antibody. In certain embodiments, a neutralizing antibody that reduces an activity of ANGPTL4 in vivo is identified by its ability to counteract or confer protection from certain effects of a fat-containing diet. Certain exemplary effects include, but are not limited to, weight gain, obesity, glucose intolerance (hyperglycemia), insulin insensitivity (hyerpinsulinemia), hepatic steatosis (fatty liver), and intramyocellular lipid accumulation. Certain exemplary assays for measuring such effects are provided below, Part VI.C., VI.E., and VI.F.

G. CERTAIN PHARMACEUTICAL COMPOSITIONS AND METHODS OF TREATMENT USING NEUTRALIZING MONOCLONAL ANTIBODIES

In certain embodiments, a neutralizing antibody may be used as a therapeutic antibody. Certain exemplary neutralizing antibodies to be used as therapeutic antibodies include, but are not limited to, chimeric antibodies, humanized antibodies, and human antibodies. Those skilled in the art are familiar with the use of certain antibodies as therapeutic agents. For example, over a dozen antibodies have been approved by the FDA for use as therapeutic agents since the mid-1980s. See, e.g., Hudson et al. (2003) *Nature Med.* 9:129-134; Gura (2002) *Nature* 417:584-586; Brekke et al. (2002) *Nature Reviews* 2:52-62. Certain FDA-approved antibodies include those used to treat various cancers, inflammation, and viral infections and to prevent transplant rejection. See, e.g., Gura (2002) *Nature* 417:584-586; Brekke et al. (2002) *Nature Reviews* 2:52-62. Furthermore, over a dozen antibodies are currently in clinical trials. See, e.g., Brekke et al. (2002) *Nature Reviews* 2:52-62.

In certain embodiments, methods are provided for treating a disorder of lipid metabolism comprising administering an effective amount of a neutralizing antibody against ANGPTL4. In certain embodiments, methods are provided for treating an acute disorder of lipid metabolism comprising administering an effective amount of a neutralizing antibody against ANGPTL4. In certain embodiments, methods are provided for treating a chronic disorder of lipid metabolism comprising administering an effective amount of a neutralizing antibody against ANGPTL4.

As used herein, "disorders of lipid metabolism" include, but are not limited to, disorders that can lead to secondary hyperlipidemia (including hypertriglyceridemia and hypercholesterolemia). Certain exemplary disorders of lipid metabolism include, but are not limited to, atherosclerosis, dyslipidemia, hypertriglyceridemia (including drug-induced hypertriglyceridemia, diuretic-induced hypertriglyceridemia, alcohol-induced hypertriglyceridemia, β-adrenergic blocking agent-induced hypertriglyceridemia, estrogen-induced hypertriglyceridemia, glucocorticoid-induced hypertriglyceridemia, retinoid-induced hypertriglyceridemia, cimetidine-induced hypertriglyceridemia, and familial hypertriglyceridemia), acute pancreatitis associated with hypertriglyceridemia, chylomicron syndrome, chylomicronemia, Apo-E deficiency, LPL deficiency or hypoactivity, hyperlipidemia (including familial combined hyperlipidemia), hypercholesterolemia, gout associated with hypercholesterolemia, xanthomatosis (subcutaneous cholesterol deposits), coronary artery disease (also called ischaemic heart disease), inflammation associated with coronary artery disease, restenosis, peripheral vascular diseases, and stroke. Certain exemplary disorders of lipid metabolism include, but are not limited to, disorders related to body weight, such as obesity, metabolic syndrome including independent components of metabolic syndrome (e.g., central obesity, FBG/pre-diabetes/diabetes, hypercholesterolemia, hypertriglyceridemia, and hypertension), hypothyroidism, uremia, and other conditions associated with weight gain (including rapid weight gain), weight loss, maintenance of weight loss, or risk of weight regain following weight loss. Certain exemplary disorders of lipid metabolism include, but are not limited to, related blood sugar disorders, such as diabetes, hypertension, and polycystic ovarian syndrome related to insulin resistance. Certain exemplary disorders of lipid metabolism include, but are not limited to, renal transplantation, nephrotic syndrome, Cushing's syndrome, acromegaly, systemic lupus erythematosus, dysglobulinemia, lipodystrophy, glycogenosis type I, and Addison's disease.

Disorders of lipid metabolism include, but are not limited to secondary hypertriglycerolemia (HTG, including but not limited to types I, V, and IV), including but not limited to, HTG due to diet (including, but not limited to, excessive alcohol consumption, weight gain, and obesity), drugs (including but not limited to, exogenous estrogen, tamoxifen, retinoids, thiazides, chlorthalidone, beta-clockers, protease inhibitors (including but not limited to ritonavir), propofol infusion, and parenteral lipid infusions), disorders of metabolism (including but not limited to diabetes, pregnancy, chronic renal failure, hypothyroidism, familial hyperlipidemia, and pancreatitis).

Disorders of lipid metabolism include, but are not limited to, lipid disorders associated with vascular access dysfunction, lipid disorders associated with proliferative diseases, including but not limited to, neoplasia (including but not limited to prostate, kidney, liver, breast, ovarian, lung, and pancreatic cancers), disorders that occur in response to inflammation, including but not limited to, those associated with, e.g., infectious diseases, wound healing, immunodeficiency syndromes (AIDS and others, including but not limited to those syndromes associated with aberrant development), scar formation, atherosclerosis, restenosis and transplantation rejection, autoimmune disorders, and chronic inflammatory diseases and disorders, which include but are not limited to, diseases including but not limited to rheumatoid arthritis, systemic lupus erythromatosis, and disorders including but not limited to Crohn's disease, colitis, inflammatory bowel disease, reactive arthritis, including Lyme disease, insulin dependent diabetes, organ specific autoimmunity, multiple sclerosis, Hashimoto's thyroiditis and Grave's disease, Sjogren's syndrome, contact dermatitis, psoriasis, scleroderma, graft versus host disease, sarcoidosis, malaria, sepsis, pancreatitis, atopic conditions, including but not limited to asthma and allergy, including but not limited to allergic rhinitis, gastrointestinal allergies, including but not limited to food allergies, eosinophilia, conjunctivitis and glomerular nephritis, blood coagulation disorders, endotoxic shock and other inflammation mediated disorders such as sleep apnea and sleepiness.

In certain embodiments, methods are provided for treating a disorder of lipid metabolism comprising administering an effective amount of an antibody to ANGPTL4 and another therapeutic agent. In certain such embodiments, the additional therapeutic agent is administered in an effective amount. In certain embodiments, the additional therapeutic agent is another antibody to ANGPTL4. In certain embodiments, the additional therapeutic agent is a non-antibody agent. In certain embodiments, the additional therapeutic agent is an agent that lowers the level of one or more serum lipids. Certain exemplary additional therapeutic agents include, but are not limited to, cholesterol synthesis inhibitors (statins), such as HMG-CoA reductase inhibitors (e.g., lovastatin, simvastatin, pravastatin, and fluvastatin); bile sequestering agents, such as cholestyramine and other resins; VLDL secretion inhibitors, such as niacin; lipoprotein lipase stimulants, such as fibric acid derivatives; lipophilic antioxidants, such as Probucol; acyl-CoA cholesterol acyl transferase inhibitors; farnesoid X receptor antagonists; sterol regulatory binding protein cleavage activating protein (SCAP) activators; microsomal triglyceride transfer protein (MTP) inhibitors; and ApoE-related peptide. In certain embodiments, the additional therapeutic agent is an agent that raises high density lipoprotein (HDL). Nonlimiting examples of such agents include, but are not limited to, cholesteryl ester transfer protein (CETP) inhibitors.

In certain embodiments, a pharmaceutical composition is provided that comprises an effective amount of an antibody to ANGPTL4 and a pharmaceutically acceptable diluent, carrier, solubilizer, emulsifier, preservative and/or adjuvant. In certain embodiments, a pharmaceutical composition is provided that comprises an effective amount of an antibody to ANGPTL4 and an effective amount of at least one additional therapeutic agent, together with a pharmaceutically acceptable diluent, carrier, solubilizer, emulsifier, preservative and/or adjuvant. In certain embodiments, the at least one additional therapeutic agent is selected from those described above.

In certain embodiments, formulation materials for pharmaceutical compositions are nontoxic to recipients at the dosages and concentrations employed.

In certain embodiments, the pharmaceutical composition comprises formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight polypeptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants. (*Remington's Pharmaceutical Sciences*, 18$^{th}$ Edition, A. R. Gennaro, ed., Mack Publishing Company (1990).

In certain embodiments, an antibody to ANGPTL4 or other therapeutic molecule is linked to a half-life extending vehicle. Certain exemplary half-life extending vehicles are known in the art. Certain such vehicles include, but are not limited to, the Fc domain, polyethylene glycol, and dextran. Certain such vehicles are described, e.g., in published PCT Application No. WO 99/25044.

In certain embodiments, an optimal pharmaceutical composition will be determined by one skilled in the art depending upon, for example, the intended route of administration, delivery format, and desired dosage. See, e.g., *Remington's Pharmaceutical Sciences*, supra. In certain embodiments, such compositions may influence the physical state, stability, rate of in vivo release, or rate of in vivo clearance of a neutralizing antibody.

In certain embodiments, a primary vehicle or carrier in a pharmaceutical composition may be either aqueous or non-aqueous in nature. For example, in certain embodiments, a suitable vehicle or carrier may be water for injection, physiological saline solution, or artificial cerebrospinal fluid, possibly supplemented with other materials common in compositions for parenteral administration. Certain exemplary vehicles include, but are not limited to, neutral buffered saline and saline mixed with serum albumin. In certain embodiments, pharmaceutical compositions comprise Tris buffer of about pH 7.0-8.5, or acetate buffer of about pH 4.0-5.5, which may further include sorbitol or a suitable substitute therefor. In certain embodiments, a composition comprising an antibody to ANGPTL4, with or without at least one additional therapeutic agents, may be prepared for storage by mixing the selected composition having the desired degree of purity with optional formulation agents (Remington's Pharmaceutical Sciences, supra) in the form of a lyophilized cake or an aqueous solution. In certain embodiments, a composition comprising an antibody to ANGPTL4, with or without at least one additional therapeutic agent, may be formulated as a lyophilizate using appropriate excipients such as sucrose.

In certain embodiments, a pharmaceutical composition is selected for parenteral delivery. In certain embodiments, a pharmaceutical composition is selected for inhalation or for delivery through the digestive tract, such as orally. Certain exemplary techniques for preparing pharmaceutically acceptable compositions are within the skill of one skilled in the art.

In certain embodiments, formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a pharmaceutical composition may be in the form of a pyrogen-free, parenterally acceptable aqueous solution comprising the desired antibody to ANGPTL4, with or without additional therapeutic agents, in a pharmaceutically acceptable vehicle. In certain embodiments, a vehicle for parenteral injection is sterile distilled water in which the antibody to ANGPTL4, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, an antibody to ANGPTL4, with or without at least one additional therapeutic agent, may be formulated as a dry powder for inhalation. In certain embodiments, an inhalation solution comprising an antibody to ANGPTL4, with or without at least one additional therapeutic agent, may be formulated with a propellant for aerosol delivery. In certain embodiments, solutions may be nebulized.

In certain embodiments, a formulation may be administered orally. In certain embodiments, an antibody to ANGPTL4, with or without at least one additional therapeutic agent, that is administered in this fashion may be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, at least one additional agent can be included to facilitate absorption of the antibody to ANGPTL4 with or without any additional therapeutic agents. In certain embodiments, diluents, flavorings, low melting point waxes, vegetable oils, lubricants, suspending agents, tablet disintegrating agents, and/or binders may also be employed.

In certain embodiments, a pharmaceutical composition comprises an effective amount of an antibody to ANGPTL4, with or without at least one additional therapeutic agent, in a mixture with non-toxic excipients which are suitable for the manufacture of tablets. In certain embodiments, by dissolving the tablets in sterile water, or another appropriate vehicle, solutions may be prepared in unit-dose form. Certain exemplary excipients include, but are not limited to, inert diluents (for example, calcium carbonate, sodium carbonate, sodium bicarbonate, lactose, and calcium phosphate); binding agents (for example, starch, gelatin, and acacia); and lubricating agents (for example, magnesium stearate, stearic acid, and talc).

Additional pharmaceutical compositions will be evident to those skilled in the art, including formulations comprising an antibody to ANGPTL4, with or without at least one additional therapeutic agent, in sustained- or controlled-delivery formulations. Certain exemplary sustained- or controlled-delivery formulations include, but are not limited to, liposome carriers, bio-erodible microparticles, porous beads, and depot injections. Certain exemplary techniques for preparing certain formulations are known to those skilled in the art. In certain embodiments, sustained-release preparations may include semipermeable polymer matrices in the form of shaped articles, e.g. films or microcapsules. Certain exemplary sustained release matrices include, but are not limited to, polyesters, hydrogels, polylactides (see, e.g., U.S. Pat. No. 3,773,919 and EP 058,481), copolymers of L-glutamic acid and gamma ethyl-L-glutamate (see, e.g., Sidman et al. (1983) *Biopolymers* 22:547-556), poly(2-hydroxyethyl-methacrylate) (see, e.g., Langer et al. (1981) *J. Biomed. Mater. Res.* 15:167-277 and Langer (1982) *Chem. Tech.* 12:98-105), ethylene vinyl acetate (Langer et al., supra), and poly-D(−)-3-hydroxybutyric acid (EP 133,988). In certain embodiments, sustained release compositions may include liposomes, which can be prepared, in certain embodiments, by any of several methods known in the art. See e.g., Eppstein et al. (1985) *Proc. Natl. Acad. Sci. USA*, 82:3688-3692; EP 036,676; EP 088,046; and EP 143,949.

In certain embodiments, a pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., lyophilized) that is reconstituted prior to administration.

In certain embodiments, kits for producing a single-dose administration unit are provided. In certain embodiments, the kits may each contain both a first container having a dried protein and a second container having an aqueous formulation. In certain embodiments, kits containing single or multi-chambered pre-filled syringes (e.g., liquid syringes and lyo-syringes) are included.

In certain embodiments, the effective amount of a pharmaceutical composition comprising an antibody to ANGPTL4, with or without at least one additional therapeutic agent, to be employed therapeutically will depend, for example, upon the context and objectives of treatment. One skilled in the art will appreciate that the appropriate dosage levels for treatment, according to certain embodiments, will thus vary depending, in part, upon the molecule delivered, the indication for which the antibody to ANGPTL4, with or without at least one additional therapeutic agent, is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 μg/kg of patient body weight, up to about 100 mg/kg or more, depending on the factors mentioned above. In certain embodiments, the dosage may range from 0.1 μg/kg up to about 100 mg/kg; 1 μg/kg up to about 100 mg/kg; or 5 μg/kg up to about 100 mg/kg, including all points (including fractions) between any of the foregoing endpoints. In certain embodiments, the dosage is between about 10 mg/kg body weight and about 60 mg/kg body weight. In certain embodiments, the dosage is about 10 mg/kg body weight, about 20 mg/kg body weight, about 30 mg/kg body weight, about 40 mg/kg body weight, about 50 mg/kg body weight, or about 60 mg/kg body weight.

In certain embodiments, a suitable dosage may be determined based on animal studies, such as those provided below, for example, in Parts VI.P, R, and T to Y.

In certain embodiments, the frequency of dosing will take into account the pharmacokinetic parameters of an antibody to ANGPTL4 and, if applicable, any additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. In certain embodiments, further refinement of the appropriate dosage is routinely made by those skilled in the art and is within the ambit of tasks routinely performed by them. In certain embodiments, appropriate dosages may be ascertained through use of appropriate dose-response data. In certain embodiments, a patient receives one dose of a pharmaceutical composition comprising an antibody to ANGPTL4. In certain embodiments, a patient receives one, two, three, or four doses per day of a pharmaceutical composition comprising an antibody to ANGPTL4. In certain embodiments, a patient receives one, two, three, four, five, or six doses per week of a pharmaceutical composition comprising an antibody to ANGPTL4. In certain embodiments, a patient receives one or two doses per month of a pharmaceutical composition comprising an antibody to ANGPTL4.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising an antibody to ANGPTL4, with or without at least one additional therapeutic agent, in an ex vivo manner. In certain such instances, cells, tissues and/or organs that have been removed from the patient are exposed to a pharmaceutical composition comprising an antibody to ANGPTL4, with or without at least one additional therapeutic agent, after which the cells, tissues and/or organs are subsequently implanted back into the patient.

In certain embodiments, an antibody to ANGPTL4, with or without at least one additional therapeutic agent, is delivered by implanting certain cells that have been genetically engineered, using methods such as those described herein, to express and secrete the polypeptides. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

H. CERTAIN METHODS OF DETECTION AND DIAGNOSIS

In certain embodiments, antibodies against ANGPTL4 are used to detect the presence of ANGPTL4 in vivo or in vitro. in certain embodiments, the level of ANGPTL4 in vivo is correlated with a medical condition, such as a disorder of lipid metabolism, thereby allowing diagnosis of the medical condition. Certain exemplary medical conditions that may be diagnosed by an antibody against ANGPTL4 are set forth above.

Certain exemplary detection methods are known in the art and include, but are not limited to, ELISA, radioimmunoassay, immunoblot, Western blot, immunofluorescence, and immunoprecipitation. In certain embodiments, antibodies against ANGPTL4 are modified so that they may be directly detected, for example, by linking the antibody to a label. Certain exemplary labels include, but are not limited to, fluorophores, chromophores, radioactive atoms, electron-dense reagents, enzymes, and ligands. In certain embodiments, antibodies against ANGPTL4 are detected by using a labeled "secondary" antibody that binds to a class of antibodies (e.g., a goat anti-mouse antibody).

I. CERTAIN SCREENING METHODS FOR ANGPTL4 ANTAGONISTS AND AGONISTS

In certain embodiments, a method of screening for an agent that binds to ANGPTL4 is provided. In certain embodiments, a screening method comprises exposing ANGPTL4 to one or more candidate agents under suitable conditions and assessing binding of ANGPTL4 to the one or more candidate agents. In certain embodiments, a screening method comprises using an antibody against ANGPTL4 in a competitive binding assay. In certain such embodiments, a first binding mixture comprising an antibody against ANGPTL4 and ANGPTL4 is used. The amount of binding between ANGPTL4 and the antibody in the first binding mixture ($M_0$) is measured. A second binding mixture comprising the antibody, ANGPTL4, and an agent to be screened is also used. The amount of binding between ANGPTL4 and the antibody in the second binding mixture ($M_1$) is measured. The amount of binding in the first binding mixture is compared with the amount of binding in the second binding mixture, for example, by calculating the $M_1/M_0$ ratio. An agent is considered to be capable of binding ANGPTL4 if the amount of binding of antibody to ANGPTL4 in the second binding mixture is less than the amount of binding of antibody to ANGPTL4 in the first binding mixture. In certain embodiments, an agent that binds ANGPTL4 decreases the binding of antibody to ANGPTL4 by at least about 10% (i.e., $M_1/M_0<0.9$), by at least about 30% (i.e., $M_1/M_0<0.7$), by at least about 50% (i.e., $M_1/M_0<0.5$), by at least about 70% (i.e., $M_1/M_0<0.3$), by at least about 80% (i.e., $M_1/M_0<0.2$), by at least about 90% (i.e., $M_1/M_0<0.1$), or by at least about 95% (i.e., $M_1/M_0<0.05$).

In certain embodiments, the ANGPTL4 to be used in any of the screening methods described above is the N-terminal coiled-coil domain of ANGPTL4 or a fragment thereof. Based on the applicants' observation that certain antibodies that bind within the N-terminal coiled-coil domain of ANGPTL4 have neutralizing activity (see below, Part VI.L. and VI.P.), an agent (e.g., an antibody or a non-antibody agent) identified by a screening method as binding to the N-terminal coiled-coil domain of ANGPTL4 is a candidate antagonist of ANGPTL4 activity. In certain embodiments, antagonist activity is verified by demonstrating that the candidate antagonist neutralizes ANGPTL4 in an in vivo or in vitro assay, such as those describe in Part VI.D. and VI.I. In certain embodiments, antagonists of ANGPTL4 are used in the treatment of disorders of lipid metabolism.

In certain embodiments, methods of screening for agents that bind to the fibrinogen domain of ANGPTL4 are provided. Based on the applicants' observation that an antibody (6G11) that binds within the fibrinogen domain of ANGPTL4 enhances ANGPTL4 activity (see Part VI.L., VI.P), an agent (e.g., an antibody or a non-antibody agent) identified by a screening method as binding to the fibrinogen domain of ANGPTL4 is a candidate agonist of ANGPTL4 activity. In certain embodiments, agonist activity is verified by demonstrating that the candidate agonist enhances ANGPTL4 in an in vitro assay, such as the assay describe in Part VI.I., or by administering the candidate agonist in vivo and testing for increased levels of one or more serum lipids. In certain embodiments, agonists of ANGPTL4 are used in the treatment of certain disorders related to excessive weight loss, such as anorexia nervosa, bulimia nervosa and the cachexia (wasting) associated with diseases such as cancer, cystic fibrosis, and AIDS.

Certain exemplary agents that can be screened for binding to ANGPTL4 include, but are not limited to, antibodies, small molecules (e.g., organic compounds, organometallic compounds, salts of organic and organometallic compounds, saccharides, amino acids, nucleosides, and nucleotides), aptamers, peptides, and peptide mimetics. Certain exemplary peptides include soluble peptides, which include, but are not limited to, members of random peptide libraries (see, e.g., Lam et al. (1991) *Nature* 354:82-84; Houghten et al. (1991) *Nature* 354:84-86) and members of combinatorial chemistry-derived molecular libraries made of D- and/or L-configuration amino acids; and phosphopeptides, which include, but are not limited to, members of random or partially degenerate, directed phosphopeptide libraries (see, e.g., Songyang (1993) *Cell* 72:767-778).

In certain embodiments, computer modeling and searching technologies permit identification of compounds, or the improvement of already identified compounds, that bind ANGPTL4. Certain exemplary molecular modeling systems include, but are not limited to, the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

J. NUCLEIC ACID ANTAGONISTS OF ANGPTL4

In certain embodiments, an isolated nucleic acid that decreases the expression of a nucleic acid encoding ANGPTL4 is provided. In certain embodiments, the nucleic acid encoding ANGPTL4 encodes mouse ANGPTL4. In certain embodiments, the nucleic encoding ANGPTL4 encodes human ANGPTL4. In certain embodiments, the isolated nucleic acid is an antisense nucleic acid. In certain such embodiments, the antisense nucleic acid is a single stranded DNA molecule that promotes the degradation of a target mRNA by an RNaseH-based mechanism. In certain embodiments, an antisense nucleic acid is an oligonucleotide of about 8-30 nucleotides in length (including all points between the end points). In certain embodiments, an antisense nucleic acid is an oligonucleotide of about 18-26 nucleotides in length.

In certain embodiments, an antisense nucleic acid encompasses an RNA molecule that reduces expression of a target nucleic acid by an RNA interference (RNAi)-based mechanism. Certain exemplary RNA molecules suitable for RNAi include, but are not limited to, short interfering RNAs (siRNAs), microRNAs (mRNAs), tiny non-coding RNAs (tncRNAs), and small modulatory RNA (smRNA). For review of certain exemplary RNAi mechanisms and RNA molecules for use in RNAi, see, e.g., Novina et al. (2004) *Nature* 430:161-164.

In certain embodiments, an siRNA that decreases expression of a nucleic acid encoding ANGPTL4 is provided. In certain embodiments, an siRNA is an oligonucleotide of about 18-26 nucleotides in length (including all points between the endpoints). In certain embodiments, an siRNA is an oligonucleotide of about 20-24 nucleotides in length, or an oligonucleotide of about 21-23 nucleotides in length. In certain embodiments, an siRNA is double-stranded RNA. In certain embodiments, an siRNA will induce the degradation of a target mRNA molecule that is complementary to the antisense strand of the siRNA. See, e.g., Novina et al. (2004) Nature 430:161-164.

The activity of an antisense nucleic acid, such as an antisense DNA molecule or an siRNA, is often affected by the secondary structure of the target mRNA. See, e.g., Vickers et al. (2003) *J. Biol. Chem.* 278:7108-7118. Thus, in certain embodiments, an antisense nucleic acid is selected that is complementary to a region of a target mRNA that is available for base-pairing. In certain embodiments, a suitable region of a target mRNA is identified by performing a "gene walk," e.g., by empirically testing a number of antisense oligonucleotides for their ability to hybridize to various regions along a target mRNA and/or to reduce target mRNA expression. See, e.g., Vickers et al. (2003) *J. Biol. Chem.* 278:7108-7118; Hill et al. (1999) *Am. J. Respir. Cell Mol. Biol.* 21:728-737. In certain embodiments, a suitable region of a target mRNA is identified using an mRNA secondary structure prediction program or related algorithm to identify regions of a target mRNA that do not hybridize to any other regions of the target mRNA. See, e.g., Hill et al. (1999) *Am. J. Respir. Cell Mol. Biol.* 21:728-737. In certain embodiments, a combination of both of the above methods is used to identify a suitable region of a target mRNA. See e.g., Hill et al. (1999) *Am. J. Respir. Cell Mol. Biol.* 21:728-737.

In certain embodiments, a method of reducing ANGPTL4 activity by reducing expression of a nucleic acid encoding ANGPTL4 is provided. In certain embodiments, the method comprises reducing expression of a nucleic acid encoding ANGPTL4 in a cell in vitro or in vivo. In certain embodiments, the method comprises administering an antisense nucleic acid that reduces expression of a nucleic acid encoding ANGPTL4 to a cell in vitro or in vivo. In certain embodiments, the nucleic acid encoding ANGPTL4 encodes human ANGPTL4. In certain embodiments, the nucleic acid encoding ANGPTL4 encodes mouse ANGPTL4.

In certain embodiments, a method of treating a disorder of lipid metabolism, such as any of those described above (Part V.G.), is provided. In certain embodiments, the method comprises administering to a patient an effective amount of an antisense nucleic acid that reduces expression of a nucleic acid encoding ANGPTL4. In certain embodiments, antisense nucleic acid is delivered to an organ that expresses a nucleic acid encoding ANGPTL4. Certain studies have shown that ANGPTL4 is induced under fasting conditions in the liver, the pituitary, and adipose tissue. Ge et al. (2004) *J. Lipid Res.* 45:2071-2079. Thus, in certain embodiments, antisense nucleic acid is delivered to the liver, the pituitary, or adipose tissue. Certain exemplary guidance for the in vivo administration of antisense nucleic acids and the sustained delivery of antisense nucleic acids in vivo, including sustained delivery to specific organs such as the liver, is provided, for example, in Khan et al. (2004) *J. Drug Targeting* 12:393-404. In certain embodiments, sustained delivery is achieved by administering antisense nucleic acid that is encapsulated or otherwise contained by a biodegradable polymer. For example, in certain embodiments, antisense nucleic acid may be contained within poly(glycolic acid) (PLGA) microspheres (e.g., 0.5-20 µm; 3000 MW). In certain embodiments, the antisense nucleic acid is conjugated to a lipophilic moiety. See Khan et al. (2004) *J. Drug Targeting* 12:393-404.

VI. EXAMPLES

A. Mouse Care and Dietary Studies

Mouse studies were performed according to federal guidelines. Mice were housed at 24° C. on a fixed 12 hour light/12 hour dark cycle and had ad libitum access to water and rodent chow (22% calories from fat) (product no. 5001; Purina, St. Louis, Mo.) or high fat diet (60% calories from fat) (product no. D12492; Research Diets, New Brunswick, N.J.) as indicated below. Mice that were fed HFD received that diet from the age of 4-5 weeks onward. Mice referred to below as being in the "fasted state" were deprived of food for 16 hours.

B. In Vivo Overexpression of ANGPTL4 Caused Hyperlipidemia

1. Overexpression of Mouse ANGPTL4 cDNA encoding full-length mouse ANGPTL4 (SEQ ID NO:1) was inserted into the Ad E1-deleted region of the adenovirus vector pFAD, thereby placing the cDNA under the control of the cytomegalovirus promoter. See Hitt et al., "Construction and propagation of human adenovirus vectors," in *Cell Biology: A Laboratory Handbook* Vol. 1, pp. 500-512 (J. E. Celis, ed., 2nd ed. 1998). The resultant construct, Ad5-mAngptl-4T, was used to infect CHO cells. As a control, cDNA encoding β-galactosidase was inserted into the Ad E1-deleted region of the adenovirus vector pFAD, thereby placing the cDNA under the control of the cytomegalovirus promoter. The resultant construct, Ad5-β-gal, was also used to infect CHO cells. Expression of either the mouse ANGPTL4 cDNA or the β-galactosidase cDNA was confirmed by Western blot of infected CHO cell extracts.

Ad5-mAngptl-4T or Ad5-P-gal was injected at $5 \times 10^{10}$ vp into C57BL/6J mice via the tail vein. Blood samples from adenovirus-infected mice were collected at various time points after infection. Triglyceride and cholesterol levels in serum were measured using the Cobas Integra 500 (Roche, Basel, Switzerland). Free fatty acid (FFA) levels in serum were measured using the NEFA C kit (99475409, Wako, Richmond, Va.).

Figure 1:
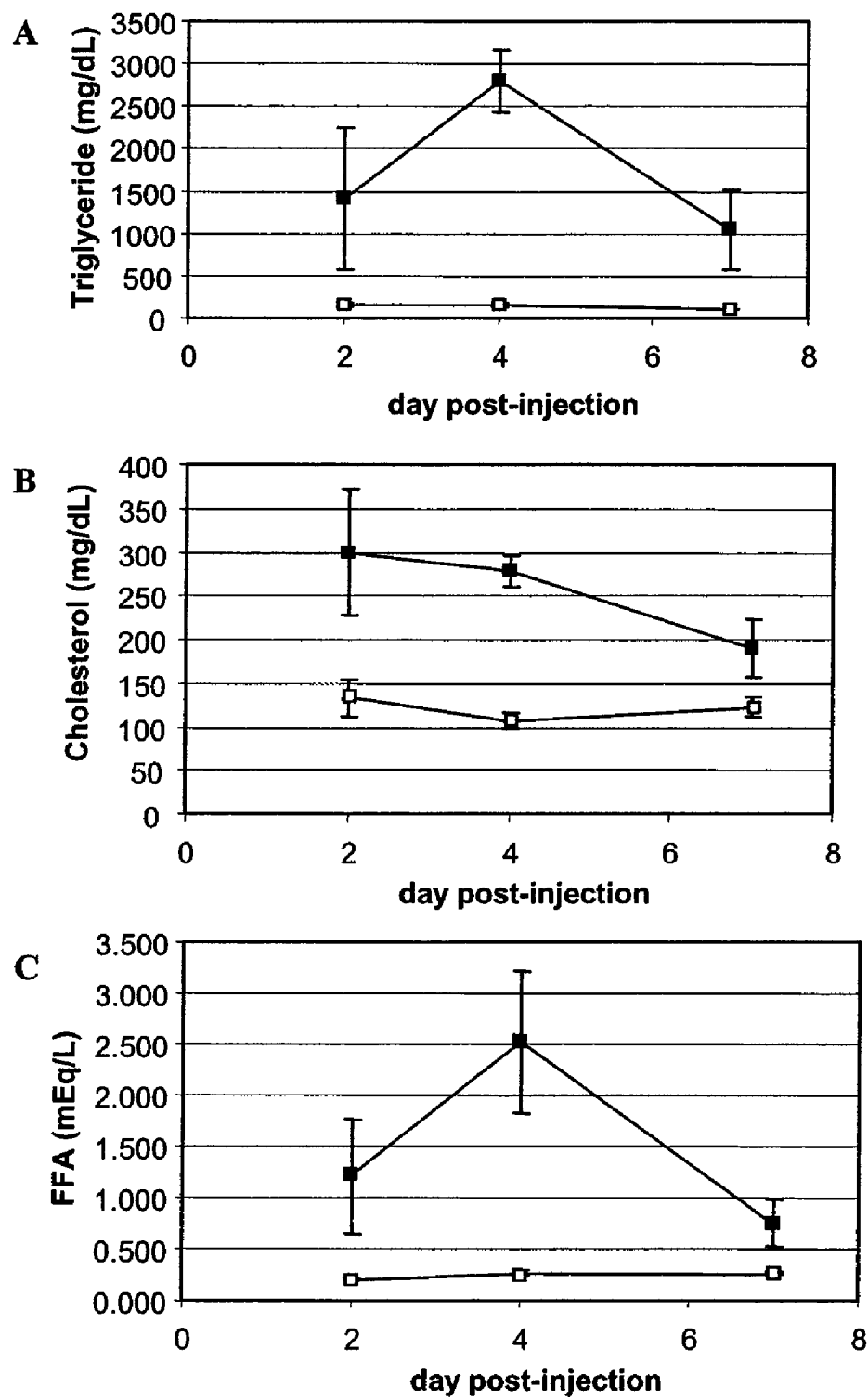
FIG. 1 shows fasted serum triglyceride (A), cholesterol (B), and free fatty acid (FFA; (C)) levels in wild-type mice at various time points following injection with an adenovirus construct overexpressing full-length mouse ANGPTL4, as described in Example B.1.
Figure 2:
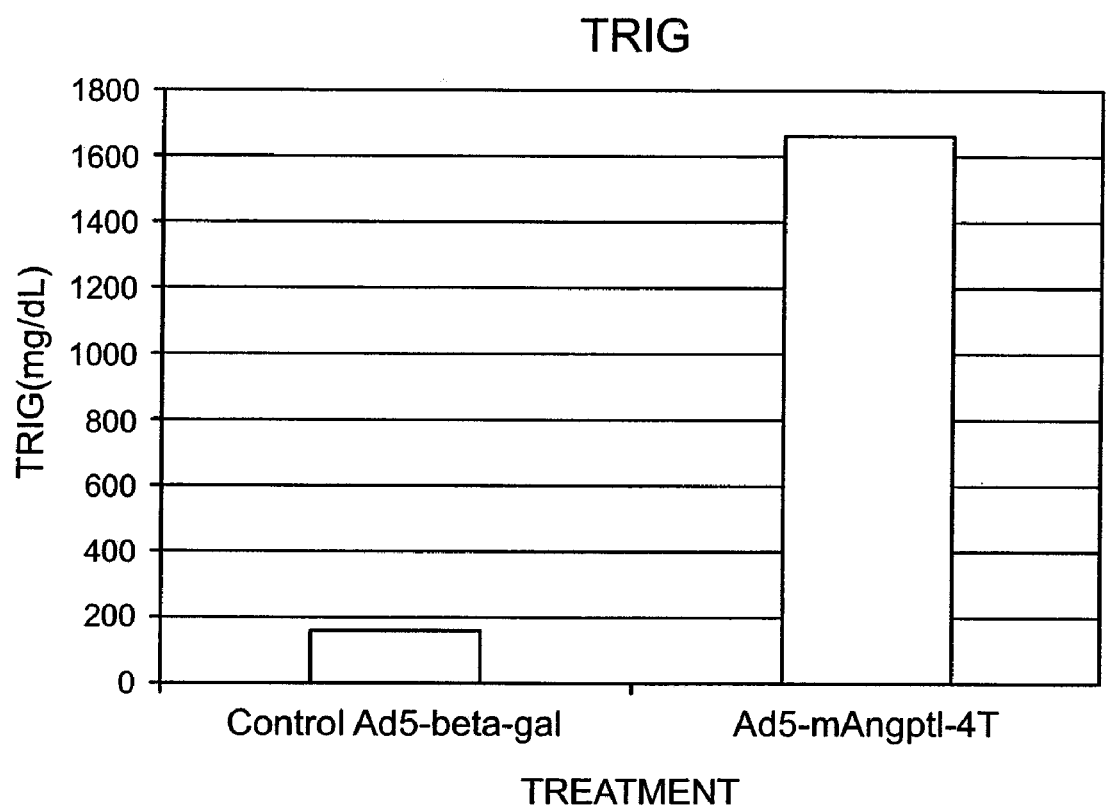
FIG. 2 shows fasted serum triglyceride levels in wild-type mice three days after injection with an adenovirus construct (Ad5-mAngptl-4T) expressing full-length mouse ANGPTL4, as described in Example B.1.
Figure 3:
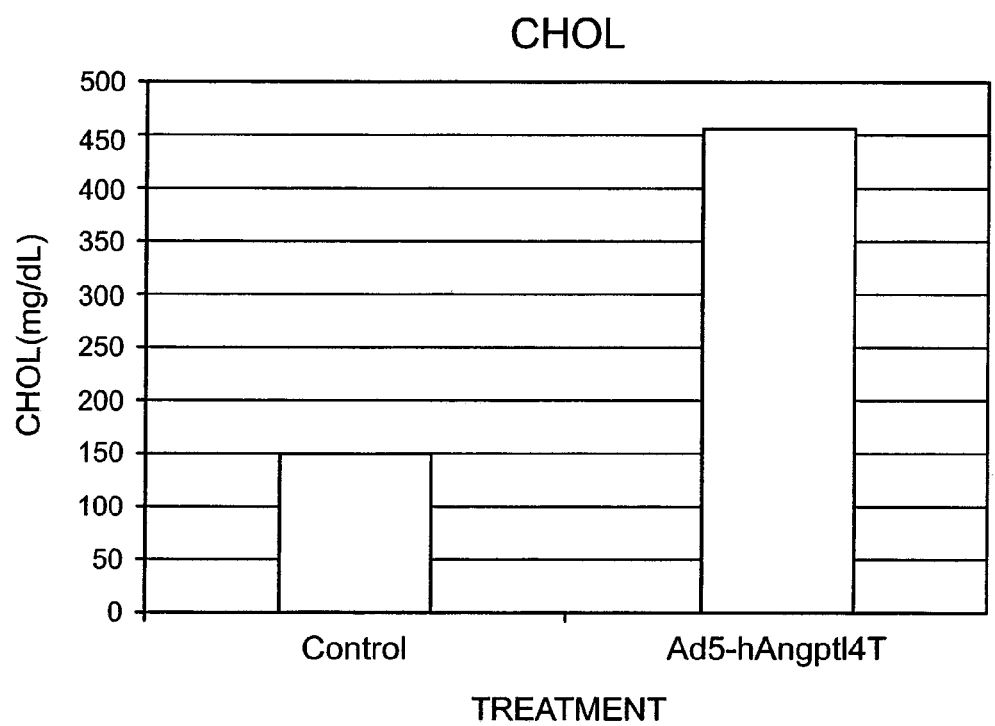
FIG. 3 shows fasted serum cholesterol levels in wild-type mice three days after injection with an adenovirus construct (Ad5-mAngptl-4T) expressing full-length mouse ANGPTL4, as described in Example B.1.

As shown in FIGS. 1A, 1B, and 1C, mice injected with Ad5-mAngptl-4T (filled squares) showed increased fasted serum levels of triglyceride, total cholesterol, and free fatty acid (FFA) relative to the control mice injected with Ad5-β-gal (open squares). Specifically, fasted serum levels of triglyceride and FFA in Ad5-mAngptl-4T-injected mice increased within two days after injection and reached a peak after 4 days (FIGS. 1A and 1C). At day 4, triglyceride was increased by about 18 fold, and FFA by about 9 fold, in mice injected with Ad5-mAngptl-4T relative to control mice. Fasted serum level of total cholesterol also increased significantly in mice injected with Ad5-mAngptl-4 relative to control mice (FIG. 1B). Fasted serum triglyceride and cholesterol levels three days after injection with either Ad5-mAngptl-4T or Ad5-β-gal are also shown in FIGS. 2 and 3.

2. Overexpression of Human ANGPTL4

Figure 4:
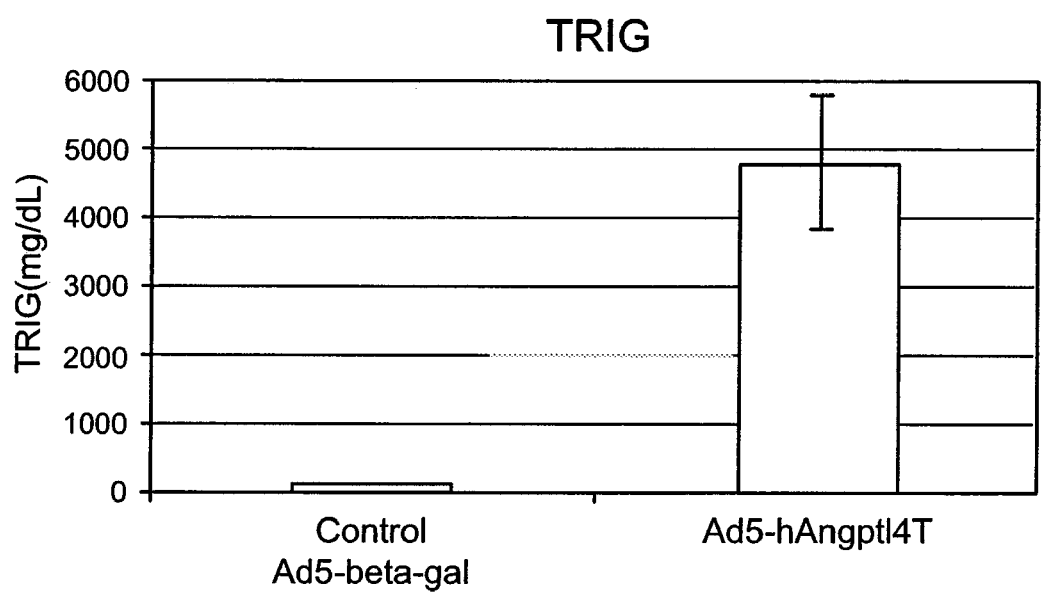
FIG. 4 shows fasted serum triglyceride levels in wild-type mice four days after injection with an adenovirus construct (Ad5-mAngptl-4T) expressing full-length human ANGPTL4, as described in Example B.2.
Figure 5:
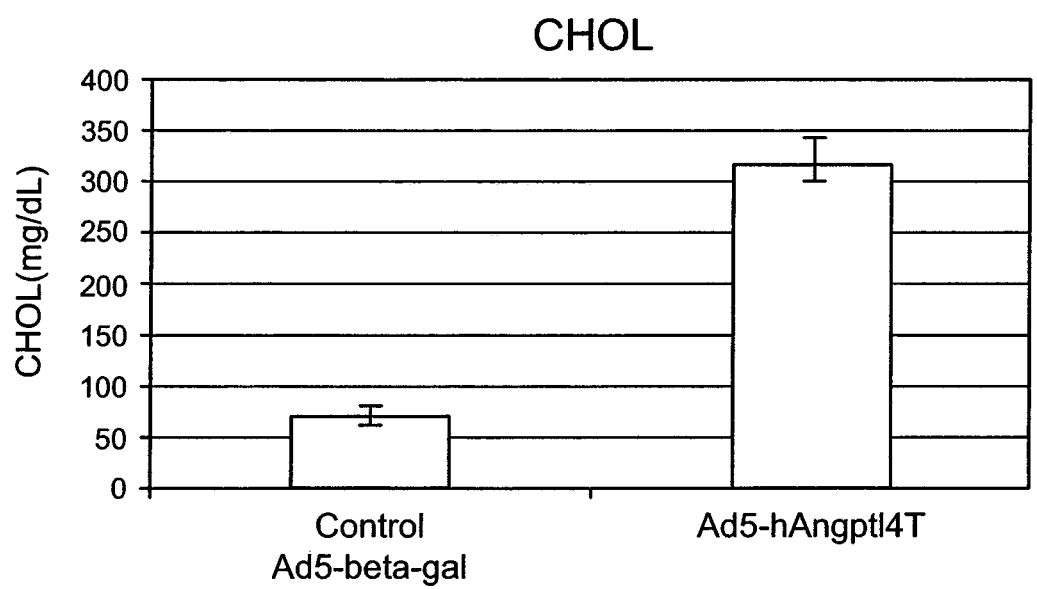
FIG. 5 shows fasted serum cholesterol levels in wild-type mice four days after injection with an adenovirus construct (Ad5-mAngptl-4T) expressing full-length human ANGPTL4, as described in Example B.2.

To determine the effects of human ANGPTL4 on mice, human ANGPTL4 was overexpressed in wild-type mice. cDNA encoding full-length human ANGPTL4 (SEQ ID NO:2) was inserted into the Ad E1-deleted region of the adenovirus vector pFAD, thereby placing the cDNA under the control of the cytomegalovirus promoter. The resulting construct, Ad5-hAngptl4T, or the control construct, Ad5-β-gal, was injected at $5 \times 10^{10}$ vp into the tail vein of C57BL/6J mice. Triglyceride and cholesterol levels in serum were measured four days after injection. As shown in FIGS. 4 and 5, human ANGPTL4 significantly raised fasted serum triglyceride and cholesterol levels relative to the control construct. Human ANGPTL4 had no effect on glucose levels in mice in this study. (Data not shown.) These results demonstrate that human ANGPTL4 is capable of raising fasted serum lipid levels in mice similar to mouse ANGPTL4.

C. Angptl4 Knockout Mice Had Reduced Serum Lipid Levels

Angptl4 was "knocked out" in mice to determine if lack of ANGPTL4 would have the opposite effect on serum lipid levels as overexpression of ANGPTL4 (i.e., to determine if lack of ANGPTL4 would decrease serum lipid levels). To knock out Angptl4 in mice, an ES cell clone with a retroviral vector inserted into the Angptl4 locus was injected into C57BL/6-Tyr$^{c-Brd}$ host blastocysts. See Zambrowicz et al. (1998) *Nature* 392:608-611. Chimeric mice were generated and bred to C57BL/6-Tyr$^{c-Brd}$ mice. The resulting Angptl4$^{+/-}$ offspring were interbred to produce Angptl4$^{-/-}$ mice. Tail DNA was genotyped by quantitative dot blots (Bio-Rad, Hercules, Calif.) using the neomycin phosphotransferase gene fragment and a fragment containing exon 1 of the murine Csk gene (MMU05247) as probes to detect virus integration and a single-copy endogenous gene, respectively.

Knockout mice had moderately reduced viability, as shown in FIG. 29. Furthermore, some pups were found to have a distended abdomen and intestinal lymphangiectasia before weaning.

In addition, knockout mice fed a high fat diet (HFD) had lower survival rates than wild-type mice fed a HFD. See FIG. 30. Some dead knockout mice were found to have distended abdomens, and some were found to have chronic inflammation and/or lipid-laden macrophages in their mesenteric lymph nodes. In addition, some mice were found to have dilated lymphatics.

Figure 6:
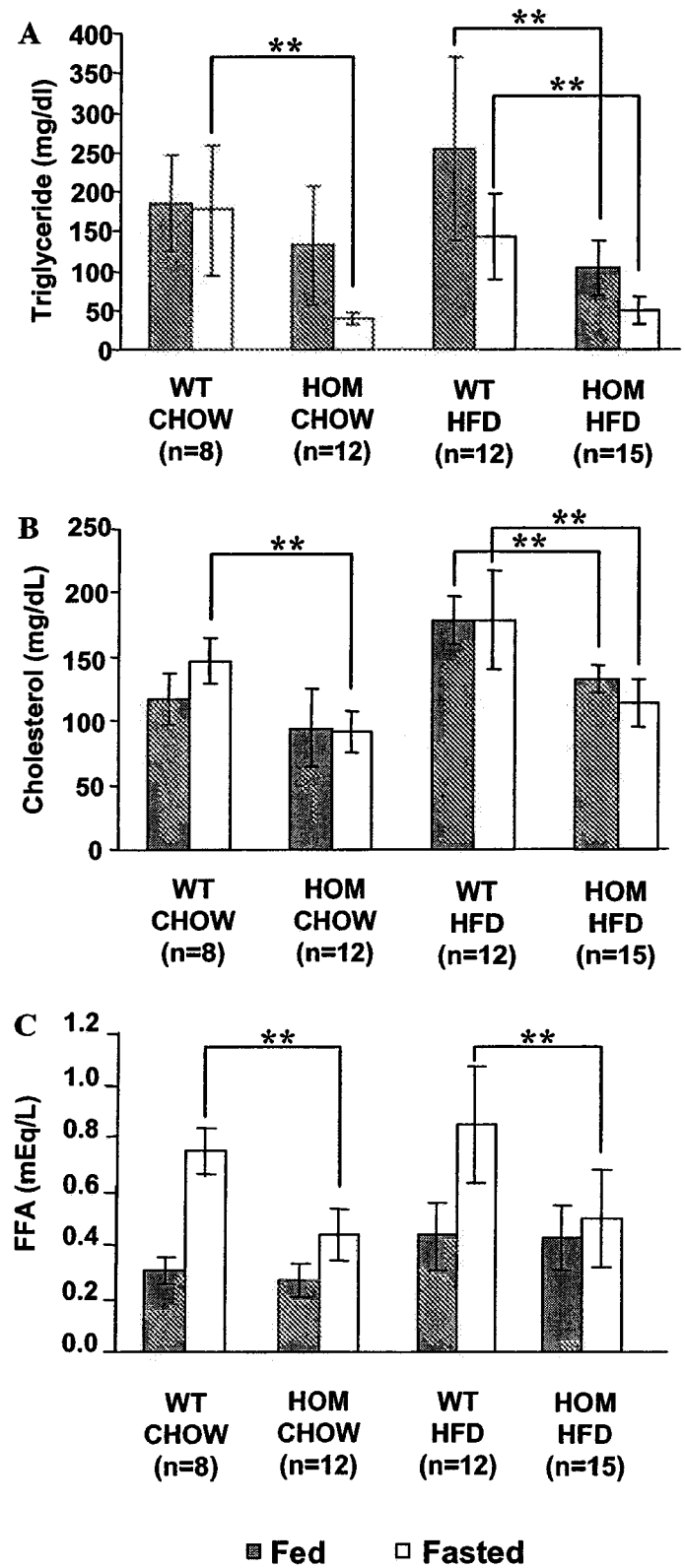
FIG. 6 shows serum triglyceride (A), cholesterol (B), and free fatty acid (FFA; (C)) levels in wild-type mice (WT) and Angptl4 knockout (HOM) mice subjected to various dietary conditions, as described in Example C.

To assess the effect of Angptl4 deficiency on serum lipid levels in mice fed a standard ("chow") diet, serum triglyceride and cholesterol levels were examined in the fed and fasted states of knockout mice and wild-type mice. The results are shown in FIG. 6 ("n" indicates the number of mice used). Serum triglyceride levels in knockout mice ("HOM") in the fasted state were 70% lower than serum triglyceride levels in wild-type mice in the fasted state (FIG. 6A). Total serum cholesterol levels and free fatty acid (FFA) levels in knockout mice in the fasted state were also significantly lower than total serum cholesterol levels and free fatty acid (FFA) levels in wild-type mice in the fasted state (FIGS. 6B and 6C).

FIG. 25, panel A, shows fasted serum triglyceride, total cholesterol, high density lipoprotein (HDL), and low density lipoprotein (LDL) levels in male wild-type, heterozygous, and knockout mice fed a standard ("chow") diet. Fasted serum triglyceride levels for heterozygous male mice were 41% lower than for wild-type male mice in that experiment. Fasted serum triglyceride levels for knockout male mice were 59% lower than for wild-type male mice in that experiment. Fasted total cholesterol levels for heterozygous and knockout male mice were 10% and 21% lower, respectively, than for wild-type male mice in that experiment.

FIG. 25, panel B, shows fasted serum triglyceride, total cholesterol, high density lipoprotein (HDL), and low density lipoprotein (LDL) levels in female wild-type and knockout mice fed a standard ("chow") diet. Fasted serum triglyceride levels for knockout female mice were 27% lower than for wild-type female mice in that experiment. Fasted total cholesterol levels for knockout female mice were 33% lower than for female wild-type male mice in that experiment. Fasted HDL levels for female knockout mice were 31% lower than for female wild-type mice in that experiment.

The effects of Angptl4 deficiency on serum lipid levels of knockout and wild-type mice with diet-induced obesity (DIO) were also examined. Knockout mice and wild-type mice were fed a high fat diet (HFD) to induce DIO. Serum lipid levels in those mice were then examined in the fed and fasted states. As shown in FIGS. 6A and 6B, serum triglycerides and total cholesterol levels were significantly reduced in knockout mice in both the fed and fasted states. Additionally, FFA levels were also significantly reduced in knockout mice in the fasted state. See FIG. 6C.

FIG. 26 shows fasted serum triglyceride, total cholesterol, HDL, and LDL levels in wild-type and knockout male mice fed a high fat diet (HFD). In that experiment, fasted serum triglyceride levels in knockout male mice fed a HFD diet were 77% lower than in wild-type mice fed a HFD. The fasted total cholesterol level in knockout male mice fed a HFD diet were 35% lower than in wild-type mice fed a HFD in that experiment.

Figure 7:
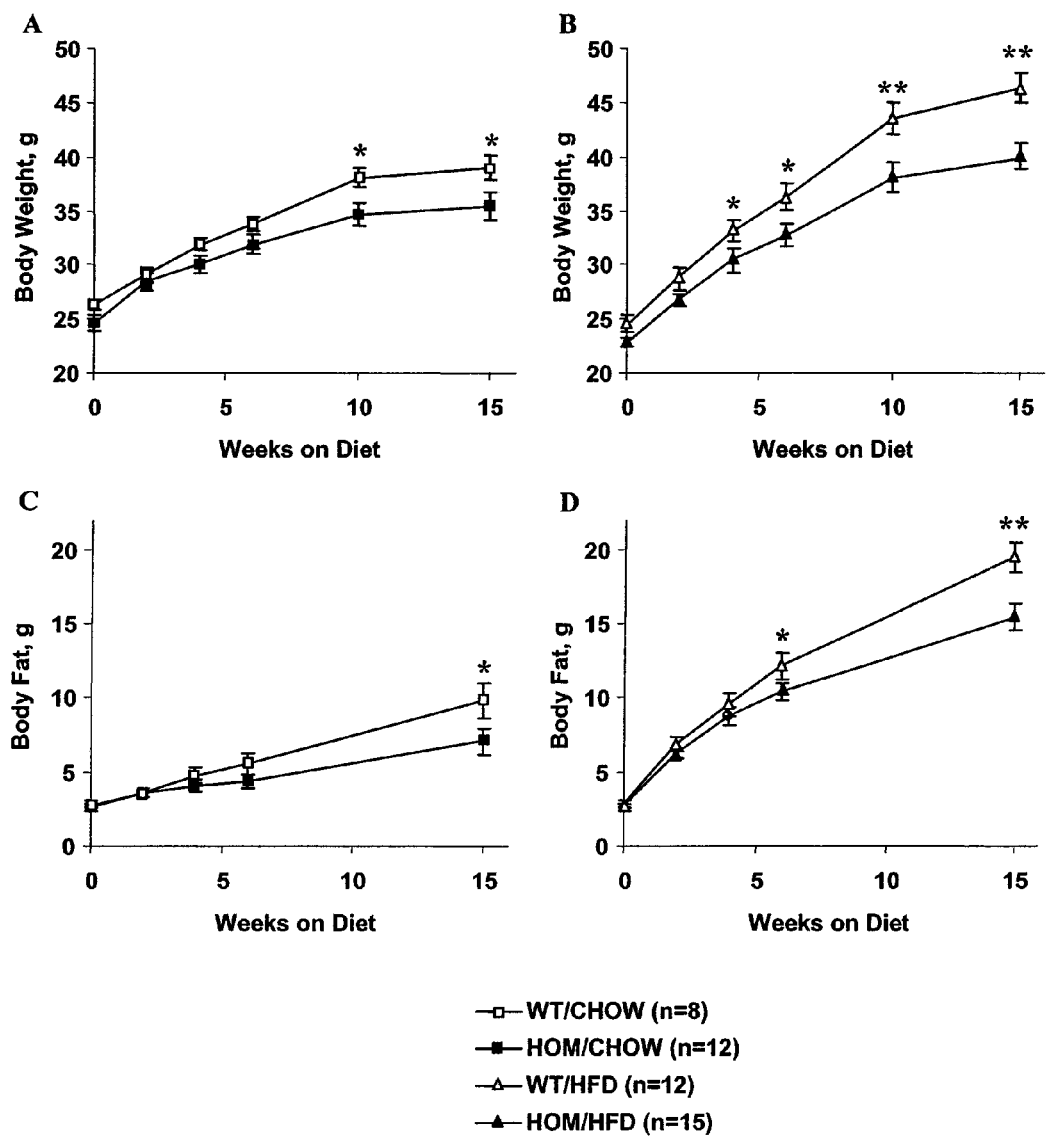
FIG. 7 shows body weight (A, B) and body fat (C, D) of wild-type (WT) mice and Angptl4 knockout (HOM) mice fed a standard ("chow") diet (A, C) or a high fat diet (HFD; B, D), as described in Example C.

Additionally, knockout mice were protected from DIO to a significant extent. Wild-type mice fed an HFD developed marked obesity in comparison with wild-type mice on a standard diet. See FIGS. 7A and 7B. However, body weight gain and body fat gain were significantly decreased for the Angptl4 knockout mice fed either standard or HFD. See FIGS. 7A-7D. The majority of decreased body weight is attributed to a decrease in the amount of body fat and not a decrease in lean body mass.

FIG. 27, panel A, shows total grams of body fat in male wild-type ("WT") and knockout ("Hom") mice fed a high fat diet (HFD). The knockout male mice fed a HFD had significantly lower body fat than the wild-type male mice fed a HFD. FIG. 27, panel B, shows total grams of body fat over time in female wild-type ("WT") and knockout ("Hom") mice fed a HFD. That experiment shows a trend toward lower body fat in the female knockout mice fed a HFD versus the female wild-type mice fed a HFD.

Male knockout mice fed a HFD had similar food intake as male wild-type mice fed a HFD. See FIG. 28, panel A. Male knockout mice fed a HFD also had similar levels of fecal fat content as male wild-type mice fed a HFD. See FIG. 28, panel B.

Overall, these results showed that Angptl4 deficiency lowered serum lipids and conferred protection against obesity.

D. Angptl4 Knockout Mice Did not Show Decreased Adipocyte LPL Activity in the Fasted State Endogenous LPL activity in adipose tissue (epididymal fat pad tissue) from wild-type and knockout mice in the fed and fasted states was examined. Tissue samples (0.3-1.0 g) were homogenized in ice-cold homogenization buffer (0.025 M $NH_3$ (pH 8.2), BSA 1 mg/ml, 5 mM EDTA, heparin 5 IU/ml, and protease inhibitor cocktail) using a Kinematica homogenizer. Following centrifugation at 3,000 g for 10 minutes at 4° C., the supernatant was collected.

Figure 8:
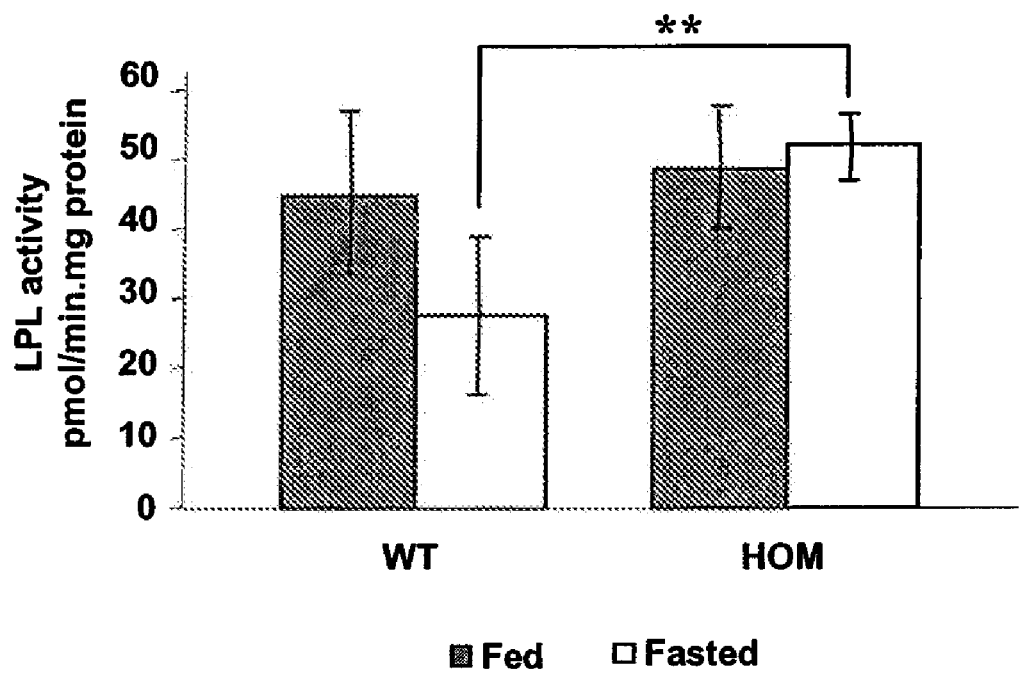
FIG. 8 shows the levels of endogenous lipoprotein lipase (LPL) activity in wild-type (WT) and Angptl4 knockout (HOM) mice in the fed and fasted states, as described in Example D.

LPL activity in the supernatant was measured by the amount of oleic acid released from a substrate, glycerol-tri[9,10(n)-$^3$H]oleate, based on the assay of Bergö et al. (1996) Biochem. J. 313:893-898). 100 µl of supernatant was added to an equal volume of substrate solution (2 mM glycerol tri[9, 10 (n)-$^3$H]oleate (131 kbeq/µmol), 189 ng/ml of L-α-phosphatidylcholine, 14 mg/ml bovine serum albumin (BSA), 140 mM Tris-HCl (pH 8.0), 15% glycerol, and 10% heat-inactivated fetal bovine serum) for 1 hour at 37° C. The reaction was stopped by adding 3.25 ml of methanol/chloroform/hexane mixture (141:125:100, v/v/v) and 1.05 ml of 0.1 M $K_2CO_3$-boric acid buffer (pH 10.5). Following vigorous vortexing and centrifugal separation at 3,000 g for 15 minutes at room temperature, the amount of $^3$H in 1 ml aliquots of the aqueous/methanol phase was determined using a Beckman Coulter LS6500 liquid scintillation counter In wild-type mice, endogenous LPL activity was significantly decreased in the fasted state relative to endogenous LPL activity in the fed state. See FIG. 8. This result was consistent with previous observations that ANGPTL4 expression is induced in the fasted state, thereby decreasing LPL activity. See, e.g., Ge et al. (2004) *J. Lipid Res.* 45:2071-2079. In knockout mice, however, endogenous LPL activity was not decreased in the fasted state relative to endogenous LPL activity in the fed state. That result was consistent with the absence of ANGPTL4 in knockout mice.

E. Angptl4 Knockout Mice were Protected from Hepatic Steatosis (Fatty Liver)

HFD has been associated with hepatic steatosis (fatty liver). To determine if Angptl4 deficiency protects against HFD-induced hepatic steatosis, localized proton magnetic resonance spectroscopy (MRS) was used to measure lipid levels in livers from wild-type and knockout mice on HFD and standard diet. Both liver fat concentration and the degree of fatty infiltration were evaluated.

In vivo MRS was performed using a 7 Tesla 16 cm bore PharmaScan system (Bruker BioSpin, Billerica, Mass.) using a birdcage coil with 38 mm inner diameter for radio-frequency transmitting and receiving. Mice were anesthetized with 1.5-2% isoflurane with their body temperature maintained by a pre-warmed water circulation system inside the magnet. Their respiratory activity was constantly monitored. The volume of interest (VOI) was selected based on a series of T1 scout images covering the whole liver and by carefully avoiding vessels and adipose tissues. Localized $^1$H-MRS was obtained using a PRESS sequence (TE=28 ms, TR=1.0 s, 196 averages, water suppression: off, VOI: 1.8×1.8×1.8 $mm^3$, or 2×2×2 mm) with respiratory synchronization. The integral of the area under the water and fat peaks was used to calculate the fat content (% fat). See Thomsen et al. (1994) *Magnetic Resonance Imaging* 12:487-495.

Livers from wild-type mice on HFD showed significantly higher lipid levels relative to livers from wild-type mice on standard ("chow") diet. See FIG. 9A. However, livers from knockout ("HOM") mice on HFD did not show significantly increased lipid levels relative to livers from knockout mice on standard diet. Further, livers from knockout mice on HFD showed significantly lower lipid levels relative to livers from wild-type mice on HFD. Consistent with these results, Oil red O staining of liver sections from knockout mice on HFD revealed significantly reduced number and size of lipid droplets relative to liver sections from wild-type mice on HFD. See FIG. 9B. Moreover, the number and size of lipid droplets in liver sections of knockout mice on HFD resembled those of wild-type mice on standard diet. These results indicate that Angptl4-deficient mice were protected against HFD-induced hepatic steatosis.

The intramyocellular lipid (IMCL) content of skeletal muscle was also measured in knockout and wild-type mice to determine if this tissue, like liver, was protected from lipid accumulation in knockout mice. For determination of the intramyocellular lipid content, in vivo MRS studies were performed on a 7 Tesla 16 cm bore PharmaScan system using a birdcage coil with 19 mm inner diameter for radio-frequency transmitting and receiving. Mice were anesthetized with 1.5-2% isoflurane, as described above, and positioned inside the coil with their hind-limbs aligned along the longitudinal axis of the magnet. The volume of interest (VOI) of $1.5 \times 1.5 \times 1.5$ mm$^3$ was selected in the left or right M. tibialis anterior, avoiding vascular structures and gross adipose tissue depots. Localized $^1$H-MRS was obtained using a PRESS sequence (TE=16 ms, TR=2.0 s, 292 averages, CHESS water suppression), to ensure that the peaks of IMCL and extramyocellular lipid (EMCL) were clearly distinct in the spectrum. The integral of the area under the ICML and tCr (total creation) peaks was used to calculate the ICML content (the ICML/tCr ratio). (The tCr concentrations for the M. tibialis anterior in obese ZDF rats at 8 weeks and 15 months of age were 136+/−2.2 and 132+/−1.0 µmol/g dry weight, respectively. See Kuhlmann et al. (2003) *Diabetes* 52:138-44.)

Figure 10:
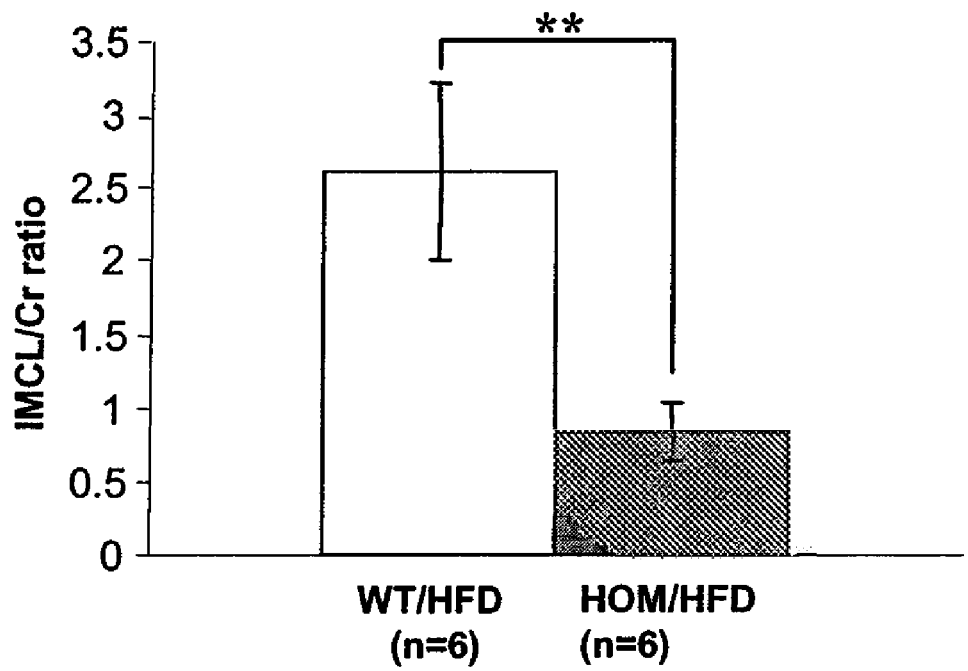
FIG. 10 shows the intramyocellular lipid content of wild-type (WT) and Angptl4 knockout (HOM) mice fed a high fat diet (HFD), as described in Example E.

Knockout mice on HFD showed significantly lower intramyocellular lipid content than did wild-type mice on HFD. See FIG. 10. Thus, Angptl4 deficiency protected important tissues, such as liver and skeletal muscle, from lipid accumulation.

F. Angptl4 Knockout Mice were Protected from Glucose Intolerance

Higher levels of hepatic and intramyocellular lipid content are known to be associated with insulin insensitivity. In addition, HFD is known to be associated with glucose intolerance. To determine if Angptl4 deficiency protected against those effects, serum levels of glucose and insulin in wild-type and knockout mice were examined.

Wild-type and knockout mice were fed a HFD. After 16 hours of fasting, blood glucose was measured by Accu-Check Advantage (2138930, Roche, Indianapolis, Ind.). Immediately thereafter, 2 g glucose/kg body weight was administered by oral gavage in a 20% sterile glucose solution. Blood glucose was subsequently measured at several time points. See FIG. 11, panel C. In that experiment, knockout mice fed a HFD were more glucose tolerant than wild-type mice fed a HFD, meaning that knockout mice receiving an oral gavage of 2 g glucose/kg body weight had lower blood glucose levels over time than wild-type mice receiving the same treatment. That result was statistically significant.

Wild-type and knockout mice were fed a HFD. After 6 hours of fasting at the start of the light cycle, blood glucose was measured. Immediately thereafter, 750 mU/kg body weight of insulin (Humulin R, Eli Lilly) was injected intraperitoneally using a 75 mU/ml solution of insulin. Blood glucose was subsequently measured at several time points. See FIG. 11, panel D. In that experiment, knockout mice fed a HFD were more insulin sensitive than wild-type mice fed a HFD, meaning that the injection of 75 mU/ml of insulin resulted in lower glucose levels over time than wild-type mice receiving the same treatment. That result was statistically significant.

Fasted serum levels of glucose and insulin in wild-type mice on HFD were significantly higher than those in wild-type mice on standard diet, indicating HFD-induced hyperglycemia and hyperinsulinemia. See FIG. 11, panels A and B. However, fasted serum levels of both glucose and insulin in knockout mice on HFD were not significantly different from levels in wild-type mice or knockout mice fed a standard diet, indicating that Angptl4 deficiency afforded protection from HFD-induced hyperglycemia and hyperinsulinemia. See FIG. 11, panels A and B.

G. Overexpression of Mouse ANGPTL4 Raised Serum Lipid Levels in Knockout Mice To determine if overexpression of mouse ANGPTL4 could rescue any of the phenotypes of Angptl4 knockout mice, the Ad5-mAngptl-4T construct (described above, Part VI.B.1.) was injected at $5 \times 10^{10}$ vp into the tail vein of knockout mice. As a control, the Ad5-β-gal construct (described above, Part VI.B.1.) was injected at $5 \times 10^{10}$ vp into the tail vein of knockout mice. Three days after injection, the knockout mice injected with the Ad5-mAngptl-4T construct showed significantly higher levels of fasted serum triglycerides and cholesterol than did knockout mice injected with a control construct. See FIGS. 12 and 13. In fact, the levels of triglycerides and cholesterol in knockout mice injected with the Ad5-mAngptl-4T construct were comparable to those in wild-type mice injected with the Ad5-mAngptl-4T construct. Compare FIGS. 12 and 13 with FIGS. 2 and 3. Those results demonstrated that overexpression of mouse ANGPTL4 reversed the reduced serum lipid levels of Angptl4 knockout mice.

H. Production and Purification of Mouse ANGPTL4

To express recombinant ANGPTL4, CHO cells were infected with $1.5 \times 10^{11}$ vp of recombinant adenovirus Ad5-mAngptl-4T (described above, Part VI.B.1.). The medium was changed to serum-free medium (EX-CELL 325-PF CHO medium, 14335, JRH, Lenexa, Kans.) 16-24 hours later. The conditioned medium was harvested and then replaced with fresh serum-free medium every 24-36 hours for a total of 5 harvests.

Conditioned medium (1 L) was loaded onto a 10-12 ml column of Nickel-Chelating Resin (R801-01, Invitrogen, Carlsbad, Calif.). The column was washed with 5 column volumes of wash buffer (10 mM imidazole, 20 mM Tris pH 7.8, 500 mM NaCl). Bound ANGPTL4 was eluted with elution buffer (500 mM imidazole, 20 mM Tris pH 7.8, 500 mM NaCl) and collected in a series of 1.5 ml fractions. The presence of ANGPTL4 in the collected fractions was determined by western blot and simply blue staining. Fractions containing ANGPTL4 were pooled together, aliquoted, and frozen at −70° C.

I. Inhibition of LPL Activity by ANGPTL4

The effect of mouse ANGPTL4 on LPL activity was determined using an in vitro assay. LPL activity was measured by the amount of oleic acid released from a substrate, glycerol-tri[9,10(n)-$^3$H]oleate, as follows (based on the method of Shimizugawa et al. (2002) *J. Biol. Chem.* 277:33742-33748).

A solution of reconstituted bovine LPL (L2254, Sigma, St. Louis, Mo.) was incubated with an equal volume of substrate solution (2 mM glycerol tri[9, 10 (n)-3H]oleate (131 kbeq/µmol), 189 ng/ml of L-α-phosphatidylcholine, 14 mg/ml bovine serum albumin (BSA), 140 mM Tris-HCl (pH 8.0), 15% glycerol, and 10% heat-inactivated fetal bovine serum) in the presence of 0 to 400 nM mouse ANGPTL4 (produced as described above, Part VI.H.) for 1 hour at 37° C. The reaction was stopped by adding 3.25 ml of methanol/chloroform/hexane mixture (141:125:100, v/v/v) and 1.05 ml of 0.1 M $K_2CO_3$-boric acid buffer (pH 10.5). Following vigorous vortexing and centrifugal separation at 3,000 g for 15 minutes at room temperature, the amount of $^3$H in 1 ml aliquots of the aqueous/methanol phase was determined using a Beckman Coulter LS6500 liquid scintillation counter. One unit of LPL activity was defined as the release of 1 µmol of $^3$H-labeled oleic acid per minute at 37° C. from the substrate. Mouse ANGPTL4 inhibited bovine LPL with an $IC_{50}$ (concentration required for 50% inhibition) of about 25 nM. See FIG. 14.

J. Generation of Monoclonal Antibodies Against ANGPTL4 in Angptl4 Knockout Mice To generate monoclonal antibodies against mouse ANGPTL4, Angptl4 knockout mice were primed and then boosted every two to three weeks with purified mouse ANGPTL4 produced as described above, Part VI.H. Complete and Incomplete Freund's Adjuvant was also used for the priming and the boosting, respectively. After two to three boosts, serum titers were monitored by ELISA. Once suitably high titers were achieved, splenocytes were harvested from the immunized mice and fused with myeloma cells (P3/NSI/1-Ag4-1) using PEG1500 as a fusion agent. The resulting cell fusion products were diluted into hybridoma medium and seeded into 96-well tissue culture plates. After 1 day, HAT medium was added to the hybridoma cultures. The medium was changed every three or four days as necessary. After ten to fourteen days of selection and culture, hybridomas were screened by ELISA with mouse ANGPTL4 used as an antigen. Nine monoclonal antibodies, designated 14D12, 15F2, 2G12, 10E4, 1A4, 5A6, 14D2, and 6G11, showed specific binding to mouse ANGPTL4.

Monoclonal antibodies were also raised against a peptide having the sequence of LAPTHLDNGVDKTSRGKR, corresponding to amino acid residues 151-168 of full-length mouse ANGPTL4 (SEQ ID NO:1). (The peptide is identical to amino acid residues 151-168 of SEQ ID NO:1, except that the C-terminal amino acid of the peptide is arginine, whereas the amino acid at position 168 of SEQ ID NO:1 is lysine.) The peptide was conjugated to KLH prior to injection. A monoclonal antibody against that peptide was able to specifically bind to full length mouse ANGPTL4. That monoclonal antibody was designated 4A8.

K. ELISA Methods

Antibodies were screened for binding to mouse ANGPTL4 using ELISA. Ninety-six well Nunc Maxi-Sorp Immuno-Plates™ (Nunc #446612, Roskilde, Denmark) were coated by adding 50 µl per well of a 2.5 µg/ml solution of ANGPTL4 in coating buffer (BupH™ Carbonate-Bicarbonate Buffer, Pierce #28382, Rockford, Ill.) overnight at 4° C. Coating buffer was removed and the plate was blocked by adding 250 µl per well of blocking buffer (1% Blocker™ BSA, Pierce #37525, in PBS) for two hours at room temperature. 50 µl of hybridoma supernatant (undiluted or diluted in blocking buffer) or isolated anti-ANGPTL4 antibody (undiluted or diluted in blocking buffer) were added to the wells and incubated for at least one hour at room temperature. Wells were washed four times with PBS/Tween 20. 100 µl of diluted (1:5,000 to 1:10,000) HRP-conjugated goat anti-mouse IgG (Pierce #31446) were added to the wells and incubated for one hour at 37° C. Wells were washed six times with PBS/Tween 20. Anti-ANGPTL4 antibody was detected by adding 50 µl of TMB (tetramethyl benzidine) solution (ImmunoPure® TMB Substrate Kit, Pierce #34021) to the wells for 5 to 10 minutes. Plates were read spectrophotometrically at 450 nm using a microplate reader (Molecular Devices, Sunnyvale, Calif.).

L. In Vitro Neutralizing Activity of Monoclonal Antibodies

Monoclonal antibodies were assayed for their ability to neutralize ANGPTL4 activity in the in vitro assay for LPL activity discussed above, Part VI.I. Separate LPL activity assays were conducted in the presence of 25 nM mouse ANGPTL4 and about 125 nM of each of the above nine monoclonal antibodies. The results are shown in FIG. 15. For each antibody, neutralizing activity is demonstrated by the antibody's ability to increase LPL activity, i.e., to "rescue," LPL from inhibition by ANGPTL4. Rescuing activity is indicated in FIG. 15 by the percentage increase in LPL activity in the presence of both ANGPTL4 and anti-ANGPTL4 antibody relative to LPL activity in the presence of ANGPTL4 alone. Five of the nine antibodies, 4A8, 14D12, 15F2, 2G12, and 10E4, resulted in an increase in LPL activity, indicating that those antibodies rescued LPL activity by neutralizing ANGPTL4 activity. In particular, antibodies 4A8, 14D12, and 15F2 rescued LPL activity by over 50%. Four of the nine antibodies, 1A4, 5A6, 14D2, and 6G11, appeared to further inhibit LPL, indicating that those antibodies are capable of enhancing ANGPTL4 activity.

M. Isotyping

The isotypes of 14D12, 15F2, 4A8, and 6G11 were determined by standard methods. 4A8 and 6G11 are of the IgG1 isotype, and 14D12 and 15F2 are of the IgG2a isotype. (See the third and fourth columns of Table 2 below, Part VI.P.)

N. Epitope Mapping of Monoclonal Antibodies

Monoclonal antibodies 14D12, 15F2, and 6G11 were tested for binding to the N-terminal coiled-coil domain of mouse ANGPTL4 (from amino acids 21-174 of SEQ ID NO:1) and the C-terminal fibrinogen-like domain of mouse ANGPTL4 (from amino acids 174-410 of SEQ ID NO:1) using ELISA. 14D12 and 15F2 specifically bound to the N-terminal coiled-coil domain of mouse ANGPTL4. 6G11 specifically bound to the C-terminal fibrinogen-like domain of mouse ANGPTL4.

O. Epitope Binning

To determine if monoclonal antibodies 14D12, 15F2, and 4A8 bind the same epitopes, epitope binning was performed using Luminex® 100 multiplex technology and the Luminex® 100™ analyzer (Luminex Corporation, Austin, Tex.). See Jia et al. (2004) *J. Immunol. Methods* 288:91-98. Epitope binning typically utilizes an antibody sandwich-type competition assay, in which a "probe" antibody is tested for binding to an antigen that is bound by a "reference" antibody. If the probe antibody binds to the same epitope as the reference antibody, it will not bind efficiently to the antigen, because that epitope is masked by the reference antibody.

To perform epitope binning, differentially labeled xMAP™ carboxylated microspheres (Luminex, Austin, Tex.) were protected from light and coated with capture antibody (rabbit monoclonal anti-mouse IgG). Coated microspheres having a given label were then allowed to selectively capture one of three reference antibodies (14D12, 15F2, or 4A8), so that each reference antibody was associated with a different label. The differentially labeled microspheres were combined and added to the wells of a microwell plate. The microspheres were dispensed into the wells and incubated overnight at 4° C. Mouse ANGPTL4 was added to the wells and incubated with agitation at 25° C. for 1 hour followed by washing. One of three probe antibodies (14D12, 15F2, or 4A8) was added to each well and incubated at 25° C. for 1 hour followed by washing. Biotinylated detection antibody (rabbit monoclonal anti-mouse IgG) was added to the wells to detect binding of ANGPTL4 by the probe antibody. Streptavidin-PE was added to the wells and incubated for 30 minutes. For each well, the Luminex® 100™ analyzer (a dual laser, flow-based, sorting and detection platform) was used to detect the particular label associated with each microsphere (and thus the identity of the reference antibody) and the magnitude of PE-derived signal associated with each microsphere. The magnitude of PE-derived signal is directly proportional to the amount of probe antibody bound to the mouse ANGPTL4.

The results are shown in FIG. 16. When 4A8 was used as a probe antibody (first set of three bars), it bound mouse ANGPTL4 when both 14D12 and 15F2 were used as reference antibodies, as indicated by a strong fluorescence signal (black and white bars). Thus, 4A8 does not bind the same epitope as 14D12 and 15F2. When 14D12 was used as a probe antibody (second set of three bars), it bound mouse ANGPTL4 when 4A8 was used as a reference antibody, but it demonstrated weak binding when 15F2 was used as a reference antibody (compare gray and white bars). Thus, 14D12 and 15F2 likely bind to the same epitope. Similarly, when 15F2 was used as a probe antibody (last set of three bars), it bound mouse ANGPTL4 when 4A8 was used as a reference antibody, but it demonstrated weak binding when 14D12 was used as a reference antibody (compare gray and black bars), thus confirming that 14D12 and 15F2 likely bind to the same epitope.

A second epitope binning experiment was performed using a BIACORE® 3000 system (Biacore AB, Uppsala Sweden) according to the manufacturer's instructions. The BIACORE® 3000 system allows real time biomolecular interaction analysis using surface plasmon resonance technology. Essentially, the ability of an antigen-antibody complex to inhibit the binding of free antibody is used to determine common epitope binding in a process of competitive inhibition.

The experiment was performed using antibodies 14D12, 15F2, 90B4, 16B10, 4A8, and 9C10. The antibodies were either directly immobilized on the BIACORE chip or linked to the chip by capture with chip bound anti-mouse IgG Fc. In order to determine the epitope bin for each antibody, the bound antibody was incubated with N-mANGPTL4 and either the same antibody in solution or a different antibody in solution. The system was then allowed to reach equilibrium. Based on reciprocal binding inhibition, the following epitope bins were assigned: Bin I contained 14D12 and 15F2, Bin II contained 90B4 and 16B10, Bin III contained only 4A8 and Bin IV contained 9C10. Those results are consistent with the first epitope binning experiment, discussed above.

P. In Vivo Administration of Monoclonal Antibodies with Neutralizing Activity Recapitulated the Knockout Phenotype Antibodies with in vitro neutralizing activity were administered to mice to determine if such antibodies could recapitulate the phenotype of Angptl4 knockout mice. To administer the antibodies in vivo, mice fed a standard diet ("chow-fed" mice) or mice with HFD-induced DIO were injected with 30 µg of a monoclonal antibody in a volume of 10 µl per gram of body weight, as indicated below in Table 2. Anti-KLH antibody was administered as a control antibody. Fasted serum levels of triglyceride, cholesterol, and FFA were measured after four days.

TABLE 2

| Groups (n = 8 mice/group) | Diet | MAb (30 mg/kg) | Isotype |
|---|---|---|---|
| 1 | Chow-Fed | Anti-KLH | IgG1 |
| 2 | Chow-Fed | Anti-KLH | IgG2a |
| 3 | Chow-Fed | 4A8 | IgG1 |
| 4 | Chow-Fed | 14D12 | IgG2a |
| 5 | Chow-Fed | 15F2 | IgG2a |
| 6 | Chow-Fed | 6G11 | IgG1 |
| 7 | HFD | Anti-KLH | IgG1 |
| 8 | HFD | Anti-KLH | IgG2a |
| 9 | HFD | 4A8 | IgG1 |
| 10 | HFD | 14D12 | IgG2a |
| 11 | HFD | 15F2 | IgG2a |
| 12 | HFD | 6G11 | IgG1 |

The results are shown in FIGS. 17-19. In mice fed a standard diet, a single administration of 14D12 significantly reduced fasted serum triglyceride levels by 72.7% and 67.0% (in two independent studies), fasted total cholesterol levels by 27.1% and 21.3% (in two independent studies), and fasted FFA levels by 44.3% (in a single study). Similarly, a single administration of 15F2 reduced fasted serum triglyceride levels by 67.6% and 71.8% (in two independent studies), fasted total cholesterol levels by 22.8% and 28.0% (in two independent studies), and fasted FFA levels by 39.3% (in a single study). Those observations are consistent with the ability of 14D12 and 15F2 to rescue LPL activity in vitro. However, a single administration of 4A8 had no significant effect on fasted serum triglyceride, cholesterol, and FFA levels (see bar graphs, FIGS. 17-19), even though that antibody was able to rescue LPL activity in vitro. In contrast, a single administration of 6G11 raised fasted serum triglyceride levels by 66.4%, which is consistent with the ability of that antibody to further inhibit LPL activity in vitro. Administration of 6G11 had no significant effect on fasted total cholesterol and FFA levels (see bar graphs, FIGS. 18-19).

The results obtained using mice with HFD-induced DIO are shown in FIGS. 20-21. A single administration of 14D12 reduced fasted serum triglyceride levels by 53.2% and fasted total cholesterol levels by 27.6%. Similarly, 15F2 reduced fasted serum triglyceride levels by 56.6% and cholesterol levels by 31.0%. 4A8 had no significant effect on either fasted serum triglyceride or total cholesterol levels (see bar graphs, FIGS. 20-21). A single administration of 6G11 significantly raised fasted serum triglyceride levels by 60.9% but had no significant effect on fasted total cholesterol levels (see bar graph, FIG. 21). FFA levels were not measured in DIO mice.

The above results showed that administration of certain antibodies that neutralize ANGPTL4 activity recapitulated the decreased serum lipid levels seen in Angptl4 knockout mice. Based on those results, it is expected that administration of such antibodies would recapitulate other aspects of the Angptl4 knockout phenotype, for example, increased endogenous LPL activity in the fasted state, increased protection from hepatic steatosis and intramyocellular lipid accumulation, and increased protection from glucose tolerance.

Neutralizing antibodies were also administered over the course of five weeks to assess the effects of continued administration. Mice with HFD-induced DIO were injected once a week with 14D12, 15F2, or an isotype-matched control antibody (antiKLH) for five weeks. The dosage was 30 µg of monoclonal antibody in a volume of 10 µl per gram of body weight. Fasted serum lipid levels were measured and compared with fasted serum lipid levels from mice receiving only a single administration of antibody. As shown in FIGS. 22-23, a single administration of 14D12 decreased fasted serum triglycerides by 53.22% and cholesterol by 27.58%, whereas weekly administration of 14D12 over the course of five weeks decreased fasted serum triglycerides by 59.36% and cholesterol by 44.21%. Similarly, a single administration of 15F2 decreased fasted serum triglycerides by 56.61% and cholesterol by 30.97%, whereas weekly administration of 15F2 over the course of five weeks decreased fasted serum triglycerides by 64.45% and cholesterol by 32.73%. In this study, weekly administration of 14D12 or 15F2 over five weeks did not have a significant effect on FFA, glucose tolerance, or body weight, compared to a single administration. (Data not shown.) These results showed that continued administration of antibodies that neutralize ANGPTL4 activity maintained or further lowered fasted serum triglyceride and total cholesterol levels relative to a single administration.

Fasted serum levels of ketone bodies (KB) were also measured in DIO mice injected weekly with 14D12, 15F2, or a control antibody (antiKLH) for five weeks as described above. DIO mice injected with 14D12 or 15F2 had significantly higher levels of ketone bodies than did DIO mice injected with control antibody. See FIG. 24. It is known that ketone bodies are produced when the body breaks down lipids. Thus, increased levels of ketone bodies may be a possible mechanism by which hepatic and intramyocellular lipid levels are reduced in mice injected with neutralizing antibody.

Q. Generation in Angptl4 Knockout Mice of Monoclonal Antibodies that Cross-React with Human and Mouse ANGPTL4

Monoclonal antibodies that cross-react with both human and mouse ANGPTL4 were raised in Angptl4 knockout mice using N-mANGPTL4, which contains a portion of the amino terminal domain of mouse ANGPTL4.

A polynucleotide sequence encoding amino acids 23 to 180 of mouse ANGPTL4 was cloned into expression vector pET22b(+) (Novagen). That vector encodes an N-terminal pelB leader sequence, as well as a C-terminal His tag. The resulting expression vector is called pET-N-mANGPTL4. Following translation of the protein and removal of all but 11 amino acids of the pelB sequence, N-mANGPTL4 has the sequence shown in SEQ ID NO: 10. That sequence contains 11 amino acids from the pelB sequence, followed by amino acids 23 to 180 of mouse ANGPTL4 (underlined in Table 6), followed by a 2 amino acid linker and the His tag.

N-mANGPTL4 is expressed and purified from *E. coli* as follows. Ten ml of LB containing 50 µg/ml of chloramphenicol and 100 µg/ml of carbenicillin is inoculated with one colony of *E. coli* transformed with pET-N-mANGPTL4. The culture is incubated at 37° C. overnight. The 10 ml culture is then transferred to 500 ml of LB without antibiotics and incubated at 37° C. until the $OD_{600}$ reaches 0.6 (about 2 hours). IPTG is added to a final concentration of 1 mM and the culture is incubated with shaking at 200 rpm at 30° C. for 4 hours. The culture is then placed on ice for 5 minutes. The cells are pelleted by centrifuging at 8000 rpm in a JLA16.25 rotor for 15 minutes. The pellet is then resuspended in 50 ml of lysis buffer (50 mM Tris, pH 7.5, 0.5 M NaCl, 1% Triton X-100, 1× protease inhibitor cocktail (Roche) and 0.25 ml PMSF (0.1 M in isopropanol)). The lysed cells are then centrifuged at 9700 rpm in a JA25.5 rotor for 30 minutes. The supernatant is removed and further clarified by centrifuging it at 28,000 rpm in an SW28 rotor for 30 minutes. Recombinant N-mANGPTL4 can then be purified from the clarified supernatant using Probond (Ni) chromatography (Invitrogen).

To purify recombinant N-mANGPTL4 from the insoluble pellet remaining after centrifuging the lysed cells, the pellet is washed with 30 ml lysis buffer and centrifuged at 9700 rpm in a JA25.5 rotor. The wash step is repeated twice, for a total of three washes. Insoluble protein from the pellet is then dissolved in 10 ml of denaturing buffer (50 mM Tris, pH 8.0, 6 M Guanadine HCl). The solution is then centrifuged at 28,000 rpm in a JA25.5 rotor for 30 minutes. The supernatant is then loaded onto a 5 ml Probond resin column. The column is washed with 50 ml of washing buffer (50 mM Tris, pH 8.0, 1 M NaCl, 8 M urea, 15 mM imidazole). Recombinant protein is refolded in the column with a 50 ml gradient going from washing buffer to renaturing buffer (50 mM Tris, pH 8.0, 1 M NaCl, 0.5% Tween 20). The recombinant protein is then eluted with elution buffer (renaturing buffer with 250 mM imidazole). The fractions containing recombinant protein are collected and dialyzed against storage buffer (50 mM Tris, pH 8.0, 100 mM NaCl, 0.2% Tween 20). The purified N-mANGPTL4 is aliquoted and stored at −70° C.

The mice were primed with 40 µg of N-mANGPTL4 in Complete Freund's Adjuvant intraperitoneally. The mice were boosted after two weeks with 30 µg of N-mANGPTL4 in Incomplete Freud's Adjuvant (IFA) intraperitoneally, and then boosted again after another two weeks with 20 µg N-mANGPTL4 in IFA intraperitoneally. Alternatively, chitosan based adjuvants can be used. See, e.g., U.S. Pat. Nos. 5,912,000; 5,965,144; and 5,980,912. One week after the second boost, serum titers were measured by ELISA, as described above in Example K, except the wells were coated with 50 µl of 0.25 µg/ml mANGPTL4. Two weeks after the second boost, the mice were boosted with 10 µg purified mouse ANGPTL4 produced as described above, Part VI.H., in IFA intraperitoneally. One week after the third boost, serum titers were again measured by ELISA as described above in this paragraph. About two and a half weeks after the third boost, the mice were boosted with 10 µg N-mANGPTL4 intravenously.

Splenocytes were harvested three days later from the immunized mice and fused with myeloma cells (NSI) using PEG1500 as a fusion agent. The resulting cell fusion products were diluted into hybridoma medium and seeded into 96-well tissue culture plates. After 1 day, HAT medium was added to the hybridoma cultures. The medium was changed every three or four days as necessary.

After ten to fourteen days of selection and culture, hybridomas were screened by ELISA to identify those that express antibody that cross-reacts with human and mouse ANGPTL4. ELISAs were performed as discussed above in Example K, except the plates were coated with 50 µl of a 0.25 µg/ml solution of protein and each antibody was separately tested against both mouse ANGPTL4 and human ANGPTL4. Mouse ANGPTL4 and human ANGPTL4 were purified from the conditioned medium of CHO cells infected with Ad5-mAngptl4T and Ad5-mAngptl4T, respectively, as discussed above in Example H. Fifteen monoclonal antibodies that cross-reacted with mouse and human ANGPTL4 were selected. The isotypes of the selected antibodies were determined, and are shown in Table 3.

TABLE 3

| Antibody designation | Isotype |
|---|---|
| 3H1 | IgG1 |
| 5A8 | IgG1 |
| 8D8 | IgG1 |
| 9C10 | IgG1 |
| 19C9 | IgG1 |
| 20C9 | IgG1 |
| 18A2 | IgG2a |
| 5F2 | IgG2b |
| 7H8 | IgG2b |
| 11C11 | IgG2b |
| 16A11 | IgG2b |
| 18G3 | IgG2b |
| 90B4 | IgG2b |

R. In Vivo Activity of Monoclonal Antibodies Against ANGPTL4

Antibodies 14D12, 19C9, 18G3, 18A2, 9C10, and 90B4, as well as anti-KLH as a control, were tested for certain in vivo activities in mice as follows. Thirty mg/kg body weight of antibody was injected into a C57 albino wild type mouse intraperitoneally. Each antibody was tested in five mice. After four days, fasted serum triglyceride and total cholesterol levels were measured. The fasted serum triglyceride levels of the antibody-injected mice in that experiment are shown in FIG. 31. Antibodies 14D12 and 90B4 reduced fasted serum triglycerides to a statistically significant extent, by 73.6% and 54.9%, respectively. Fasted total cholesterol levels of the antibody-injected mice in that experiment are shown in FIG. 32. Antibodies 14D12 and 90B4 reduced fasted total cholesterol to a statistically significant extent, by 25.2% and 22.2%, respectively.

S. Relative Binding Affinity of Monoclonal Antibodies Against ANGPTL4

The binding affinity of antibodies 90B4, 15F2, and 14D12 were determined for each of N-mANGPTL4 and N-hANGPTL4 by ELISA. N-hANGPTL4 was expressed and purified from bacteria as described above for N-mANGPTL4 in Example Q. A polynucleotide sequence encoding amino acids 24 to 175 of human ANGPTL4 was cloned into expression vector pET22b(+), which encodes an N-terminal pelB leader sequence and a C-terminal His tag. Following translation of the protein and removal of all but 11 amino acids of the pelB sequence, N-hANGPTL4 has the sequence shown in SEQ ID NO: 11. That sequence contains 11 amino acids from the pelB sequence, followed by amino acids 24 to 175 of human ANGPTL4 (underlined in Table 6), followed by a 2 amino acid linker and the His tag. ELISAs were performed as discussed above in Example K, except the plates were coated with 50 μl of 0.25 μg/ml of protein (N-mANGPTL4 or N-hANGPTL4) per well. Binding was measured at 0 μg/ml, 0.08 μg/ml, 0.4 μg/ml, 2 μg/ml, and 10 μg/ml antibody. The results of that experiment are shown in FIG. 33. 90B4 had greater affinity for both N-mANGPTL4 (panel A) and N-hANGPTL4 (panel B) than either 15F2 or 14D12. 15F2 had greater affinity for N-mANGPTL4 than 14D12, but comparable affinity as 14D12 for N-hANGPTL4.

T. Dose Response of 14D12 in Lowering Serum Triglycerides

Five C57 albino wild-type mice fed a HFD were injected subcutaneously with the specific concentrations discussed below of either 14D12 antibody or anti-KLH antibody. After 4 days and 7 days, the percent reduction in total triglycerides relative to time 0 was determined. The antibody concentrations tested in that experiment were 0.3 mg/kg body weight, 1 mg/kg body weight, 3 mg/kg body weight, 10 mg/kg body weight, 30 mg/kg body weight, and 90 mg/kg body weight. The results of that experiment are shown in FIG. 34. After 4 days, administration of 10 mg/kg body weight, 30 mg/kg body weight, and 90 mg/kg body weight resulted in a statistically significant reduction in serum triglycerides. See FIG. 34, panel A. That effect continued, and remained statistically significant after 7 days. See FIG. 34, panel B.

U. Pharmacodynamics and Pharmacokinetics of Monoclonal Antibodies Against ANGPTL4 to determine the pharmacodynamics of 14D12, C57 albino mice were injected with 30 μg/g body weight of 14D12 and their fasted serum triglyceride and total cholesterol levels were measured after certain time intervals set forth in Table 4, below. Mice were fed a regular ("chow") diet. A total of eight groups of three mice each were used in the experiment. One group of three mice was not injected with antibody and was used as baseline. The remaining seven groups of mice received 14D12 injections. The mice were injected, fasted, and bled according to the following schedule:

TABLE 4

| Group | Day injected | Day fasted | Day bled | Timepoint (day) |
|---|---|---|---|---|
| 1 | 3 | 3 | 4 | 1 |
| 2 | 2 | 3 | 4 | 2 |
| 3 | 1 | 3 | 4 | 3 |
| 4 | 4 | 7 | 8 | 4 |
| 5 | 3 | 7 | 8 | 5 |
| 6 | 2 | 7 | 8 | 6 |
| 7 | 1 | 7 | 8 | 7 |

To determine the pharmacokinetics of 14D12, four C57 albino mice were injected with 30 mg/kg body weight of 14D12 at 8 a.m. on day 1. Four additional C57 albino mice were injected with 30 mg/kg anti-KLH at 8 a.m. on day 1 as a control. Each mouse was then bled after 1 hour, 5 hours, 10 hours, 1 day, 2 days, 4 days, 7 days, 10 days, and 14 days, and the concentration of antibody in the blood determined as follows. An ELISA was performed as discussed above in Example K, except each well was coated with 50 μl of 0.5 μg/ml of N-mANGPTL4. The following dilutions of mouse serum were tested by ELISA: $1:10^3$, $1:10^4$, $1:10^5$, $1:10^6$. Standards containing 0.08 μg/ml, 0.4 μg/ml, 2 μg/ml, and 10 μg/ml of 14D12 were tested in parallel with the mouse serum dilutions.

The results of those experiments are shown in FIG. 35. Panel A shows a plot of 14D12 concentration and fasted serum triglyceride levels over time. 14D12 concentration peaks at about 24 hours after injection, while fasted serum triglyceride concentration reaches a minimum about 96 hours after injection, and remains lowered until at least 336 hours after injection, when the experiment ended. Panel B shows a plot of 14D12 concentration and fasted total cholesterol levels over time. As stated above, 14D12 concentration peaks at about 24 hours after injection. Fasted total cholesterol reaches a minimum about 168 hours after injection, and remains lowered until at least 336 hours after injection, when the experiment ended.

V. Administration of Monoclonal Antibodies Against ANGPTL4 in Mice that Overexpress Human ANGPTL4

To determine whether certain monoclonal antibodies can reduce fasted serum triglycerides and total cholesterol in mice that overexpress human ANGPTL4, Ad5-hAngptl4T (described in Example B.2., above) was injected at $1\times10^9$ IU/mouse into the tail veins of C57 albino mice. A total of four groups of five mice each were injected with Ad5-hAngptl4T. Each of the four groups were also injected with 30 mg/kg of an antibody at the same time as virus infection. The antibodies injected were anti-KLH, 14D12, 15F2, and 90B4. After four days, fasted serum triglyceride and total cholesterol levels were measured in the mice.

FIG. 36 shows fed serum triglyceride levels in the mice in that experiment. Each of the five mice in each group is represented by a different symbol in FIG. 36. Mice injected with anti-KLH had serum triglyceride levels of between about 750 mg/dl and about 1900 mg/dl. Three of the mice injected with 14D12 had serum triglyceride levels below those of mice injected with anti-KLH. The remaining mice injected with 14D12 had elevated triglyceride levels relative to mice injected with anti-KLH. Three of the mice injected with 15F2 had serum triglyceride levels well below those of mice injected with anti-KLH, while the remaining two mice injected with 15F2 had serum triglyceride levels that were similar to mice injected with anti-KLH. Finally, three of the mice injected with 90B4 had serum triglyceride levels below those of mice injected with anti-KLH, while two of the mice injected with 90B4 had elevated serum triglyceride levels relative to mice injected with anti-KLH.

The results show that about half of the mice injected with antibodies against ANGPTL4 had reduced serum triglyceride levels relative to the mice injected with anti-KLH antibody. Some mice injected with antibodies against ANGPTL4 had elevated serum triglyceride levels, which may be due to the variation of Ad-hANGPTL4T infection and possible expression in the liver.

FIG. 37 shows the fasted total cholesterol levels in the mice in that experiment. Each of the five mice in each group is represented by the same symbol as in FIG. 36. All five of the mice injected with anti-KLH had total cholesterol levels of between about 180 mg/dl and about 240 mg/dl. Three of the mice injected with 14D12 had total cholesterol levels below those of mice injected with anti-KLH. The remaining two mice injected with 14D12 had total cholesterol levels above those of mice injected with anti-KLH. Four of the mice injected with 15F2 had total cholesterol levels below those of mice injected with anti-KLH, while one mouse injected with 15F2 had a total cholesterol level comparable to mice injected with anti-KLH. Finally, two of the mice injected with 90B4 had total cholesterol levels lower than those of mice injected with anti-KLH, while one of the mice injected with 90B4 had a comparable cholesterol level to mice injected with anti-KLH, and one of the mice injected with 90B4 had a total cholesterol level greater than mice injected with anti-KLH.

Overall, about half of the mice infected with Ad5-hANGPTL4T and injected with antibodies against ANGPTL4 had total cholesterol levels lower than mice infected with Ad5-hANGPTL4T and injected with anti-KLH. Again, the mice infected with Ad5-hANGPTL4T and injected with antibodies against ANGPTL4 that had elevated cholesterol levels may be the result of variation of Ad5-ANGPTL4T infection and possible expression in the liver.

These results demonstrate that injection with antibodies 14D12, 15F2, and 90B4 may reduce serum triglycerides and total cholesterol in mice overexpressing human ANGPTL4.

W. Administration of Monoclonal Antibodies Against ANGPTL4 in LDLr Knockout Mice LDLr knockout mice have been found to have elevated serum cholesterol levels, especially when fed a high fat diet. See, e.g., Ishibashi et al. (1993) *J. Clin. Invest.* 92 :883-93. To determine if certain monoclonal antibodies against ANGPTL4 could reduce serum cholesterol and triglyceride levels in LDLr knockout mice, the following experiment was performed. Three groups of fifteen 12- to 13-week old LDLr knockout mice (Jackson Laboratories, strain B6.129S7-Ldlr$^{tm1Her}$/J) were injected with vehicle alone, 30 mg/kg anti-KLH, or 30 mg/kg 14D12 intraperitoneally. Each mouse received one injection per week for fifteen weeks. A fourth group of fifteen mice was left untreated. All mice were fed a Clinton diet (Research Diets, product no. D12107 beginning on the day of the first injection.

Fasted serum triglyceride levels were determined in each mouse at the end of 15 weeks. See FIG. 38. Serum triglyceride levels in mice injected with 14D12 were significantly lower than serum triglyceride levels in mice injected with anti-KLH, vehicle, or mice that were untreated.

Fasted total cholesterol levels were determined in each mouse at the end of 15 weeks. See FIG. 39. Total cholesterol levels in mice injected with 14D12 were significantly lower than total cholesterol levels in mice injected with anti-KLH, vehicle, or mice that were untreated.

In that experiment, LDLr knockout mice injected with 14D12 each week for 14 weeks showed no difference in glucose tolerance or insulin levels relative to LDLr knockout mice injected with anti-KLH or vehicle each week for 14 weeks. Furthermore, in that experiment, there was no difference in body fat content, body fat percentage, or lean body mass between mice injected with 14D12 each week for 8 weeks and mice injected with anti-KLH or vehicle each week for 8 weeks. Finally, the percentage of plaque in the aortic tree of mice injected with 14D12 each week for 15 weeks was not statistically significantly different from the percentage of plaque in the aortic tree of mice injected with either anti-KLH or vehicle each week for 15 weeks in that experiment. (Data not shown.)

Those results showed that 14D12 can lower serum triglyceride and total cholesterol levels in LDLr knockout mice. In that experiment, monoclonal antibody 14D12, however, did not cause increased glucose tolerance or changes in insulin levels in those mice. In that experiment, monoclonal antibody 14D12 did not alter body composition in those mice or reduce the percentage of plaque in the aortic tree. In addition, at the end of the experiment, one of thirteen LDLr knockout mice that received 15 weekly injections of 14D12 had a distended abdomen, while two of thirteen LDLr knockout mice that received 15 weekly injections of 14D12 had typical lesions in the mesenteric lymph nodes and lymphatics. Finally, serum inflammatory cytokines were not elevated in LDLr knockout mice who received 15 weekly injections of 14D12 relative to mice who received anti-KLH or vehicle. (Data not shown.)

Next, the effect of a single injection of 14D12 in LDLr knockout mice was determined. Each mouse received a single intraperitoneal injection of 30 mg/kg body weight of either anti-KLH or 14D12. Six mice were injected with 14D12 and five mice were injected with anti-KLH. After four days, fasted serum triglyceride and total cholesterol levels in the mice were determined.

Fasted serum triglyceride levels are shown in FIG. 42. A single injection of 14D12 resulted in a 68.8% reduction in serum triglycerides after 4 days. That result was statistically significant. Fasted total cholesterol levels are shown in FIG. 43. 14D12 did not reduce cholesterol levels to a statistically significant extent in that experiment.

Those results demonstrated that a single injection of the monoclonal antibody against ANGPTL4 tested in that experiment resulted in a significant reduction in serum triglycerides in LDLr knockout mice.

X. Administration of Monoclonal Antibodies Against ANGPTL4 in ApoE Knockout Mice ApoE knockout mice have been found to develop spontaneous hypercholesterolemia. See, e.g., Piedrahita et al. (1992) *Proc. Natl. Acad. Sci. USA* 89(10):4471-5; and Zhang et al. (1992) *Science* 258(5081):468-71. To determine if certain monoclonal antibodies against ANGPTL4 can reduce serum cholesterol and triglyceride levels in ApoE knockout mice, the following experiment was performed. Three groups of fifteen 14-week old ApoE knockout mice (Taconic Aminal Models, strain B6.129P2-Apoe$^{tm1Unc}$ N11) were injected with vehicle alone, 30 mg/kg anti-KLH, or 30 mg/kg 14D12 intraperitoneally. Each mouse received one injection per week for fifteen weeks. A fourth group of fifteen mice was left untreated. All mice were fed a Western diet (Research Diets, product no. D12079B) beginning on the day of the first injection.

Fasted serum triglyceride levels were determined in each mouse at the end of 15 weeks. See FIG. 40. Serum triglyceride levels in mice injected with 14D12 were significantly lower than serum triglyceride levels in mice injected with anti-KLH or mice that were untreated. However, serum triglyceride levels in mice injected with 14D12 were not significantly lower than serum triglyceride levels in mice treated only with vehicle in that experiment.

Fasted total cholesterol levels were determined in each mouse at the end of 15 weeks. See FIG. 41. Total cholesterol levels in mice injected with 14D12 were not significantly lower than total cholesterol levels in mice injected with anti-KLH or vehicle in that experiment, but were significantly lower than total cholesterol levels in mice left untreated.

In that experiment, there was no difference in body fat content, body fat percentage, or lean body mass between mice injected with 14D12 each week for 15 weeks and mice injected with anti-KLH or vehicle each week for 15 weeks. Furthermore, the percentage of plaque in the aortic tree of mice injected with 14D12 each week for 15 weeks not statistically significantly different from the percentage of plaque in the aortic tree of mice injected with either anti-KLH or vehicle each week for 15 weeks in that experiment. (Data not shown.)

Those results showed that 14D12 can lower serum triglyceride levels in ApoE knockout mice. In that experiment, however, monoclonal antibody 14D12 did not reduce total cholesterol levels in ApoE knockout mice. In that experiment, monoclonal antibody 14D12 also did not alter body composition in those mice or reduce the percentage of plaque in the aortic tree. In addition, at the end of the experiment, three out of fifteen ApoE knockout mice that received 15 weekly injections of 14D12 had a distended abdomen, while thirteen out of fifteen of the ApoE knockout mice that received 15 weekly injections of 14D12 had typical lesions in the mesenteric lymph nodes and lymphatics. Finally, six out of fifteen of the ApoE knockout mice that received 15 weekly injections of 14D12 had chylous ascites. Serum inflammatory cytokines were not elevated in ApoE knockout mice who received 15 weekly injections of 14D12 relative to mice who received anti-KLH or vehicle. (Data not shown.)

Next, the effect of a single injection of 14D12 in ApoE knockout mice was determined. Each mouse received a single intraperitoneal injection of 30 mg/kg body weight of either anti-KLH or 14D12. Six mice were injected with 14D12 and seven mice were injected with anti-KLH. After four days, fasted serum triglyceride and total cholesterol levels in the mice were determined.

Fasted serum triglyceride levels are shown in FIG. 44. A single injection of 14D12 resulted in a 55.4% reduction in serum triglycerides after 4 days. That result was statistically significant. Fasted total cholesterol levels are shown in FIG. 45. A single injection of 14D12 resulted in a 39.5% reduction in serum triglycerides after 4 days. That result was also statistically significant.

Those results demonstrated that a single injection of monoclonal antibody 14D12 can results in a significant reduction in serum triglycerides and total cholesterol levels in ApoE knockout mice.

Y. Administration of a Monoclonal Antibody Against ANGPTL4 to db/db mice

Db/db mice have been found to display obesity and diabetic phenotypes. See, e.g., Chen et al. (1996) *Cell* 84:491-495; and Chua Jr et al. (1996) *Science* 271:994-996. To determine the effect of certain monoclonal antibodies against ANGPTL4 on obesity and diabetes parameters, the following experiment was performed.

Each mouse in a first group of ten db/db mice was injected with 30 mg/kg body weight of anti-KLH subcutaneously. Each mouse in a second group of ten db/db mice was injected with 30 mg/kg body weight of 14D12 subcutaneously. Fasted serum triglyceride levels were measured prior to injection, and then measured one week after injection. The mice then received weekly injections, and the fasted serum triglyceride levels were measured after 8 weekly injections. Mice were fed a chow diet.

The results are shown in FIG. 46. Panel A shows fasted serum triglyceride levels one week after a single injection with anti-KLH or 14D12. In that experiment, injection of 14D12 reduced serum triglycerides to a statistically significant extent. Panel B shows fasted serum triglycerides in mice after 8 weekly injections with 14D12 or anti-KLH. In that experiment, 14D12 reduced serum triglycerides by 56%, which was statistically significant.

Serum glucose and insulin levels were not changed by 14D12 injection in that experiment. Body weights of the mice were also not changed by 14D12 injection in that experiment.

Z. Sequencing of Certain Monoclonal Antibodies Against ANGPTL4

The heavy chain and light chain variable regions of 14D12, 15F2, and 90B4 were cloned and sequenced using a modified version of the method described in Gilliland et al (1996)

Tissue Antigens 47: 1-20. The method was modified to use RACE and PCR primers suitable for the mouse genetic background. An alignment of the heavy chain variable regions, including a consensus sequence (SEQ ID NO: 15), is shown in FIG. 47. In addition, the percent homology of the heavy chain variable regions between each of the antibodies is shown in that Figure. The heavy chain variable regions of 14D12 (SEQ ID NO: 12) and 15F2 (SEQ ID NO: 13) are 99% identical, while the heavy chain variable region of 90B4 (SEQ ID NO: 14) is only 40% identical to the heavy chain variable regions of 14D12 and 15F2.

An alignment of the light chain variable regions, including a consensus sequence (SEQ ID NO: 19), is shown in FIG. 48. The percent homology of the light chain variable regions is shown as well. The light chain variable regions of 15F2 (SEQ ID NO: 17) and 90B4 (SEQ ID NO: 18) are 99% identical, while the light chain variable region of 14D12 (SEQ ID NO: 16) is only 52% and 51% identical to the light chain variable regions of 15F2 and 90B4, respectively.

AA. Epitope Mapping of Certain Monoclonal Antibodies Against ANGPTL4

To identify the epitopes for monoclonal antibodies 15F2.14D12, and 90B4, the following experiment was performed. Various fragments of mouse ANGPTL4 were translated in vitro. The location of the fragments are shown in Table 5 and the sequence of the fragments are shown in Table 6 (SEQ ID NOs: 40 to 48). The starting amino acid and ending amino acid in Table 5 refer to the amino acid sequence of mANGPTL4 shown in SEQ ID NO: 50.

TABLE 5

| fragment | Starting amino acid | Ending amino acid |
| --- | --- | --- |
| gs1 | Q24 | M73 |
| gs2 | L49 | P98 |
| gs3 | A74 | L123 |
| gs4 | E99 | L151 |
| gs5 | F124 | P180 |
| gs1-2 | L49 | M73 |
| gs2-3 | A74 | P98 |
| gs3-4 | E99 | L123 |
| gs4-5 | F124 | L151 |

Each fragment was expressed from a construct that was generated using PCR. Each PCR-derived construct contained a T7 promoter, a sequence encoding a His$_6$ tag, a sequence encoding a small-ubiquitin-like modifier (SUMO), and the sequence encoding the ANGPTL4 fragment. The PCR constructs were translated in vitro using RTS E. coli Linear Template Generation Set (Roche Diagnostics) and RTS 100 E. coli HY kit (Roche Diagnostics), both as directed by the manufacturer. The ANGPTL4 portion of a fragment is referred to as "gs1," "gs2," etc., as shown in Table 5. The in vitro translated protein fragments, including the His tag and SUMO sequence, are referred to as "His-SUMO-gs1," "His-SUMO-gs2," etc., as shown in FIG. 49.

The in vitro translated protein fragments were separated on four SDS-PAGE gels, along with N-mANGPTL4, and transferred to four nitrocellulose blots. The blots were then blocked for 1 to 2 hours with TBS containing 5% nonfat dried milk (TBS-NFDM). After blocking, the blots were rinsed with TBS containing 0.5% Tween-20 (TBS-Tween) four times for five minutes each rinse. The blots were then incubated in TBS-NFDM containing tester antibody (14D12.15F2.90B4, or anti-His) overnight at 40C. The blots were rinsed with TBS-Tween four times for five minutes each rinse and then incubated in TBS-NFDM containing a 1:6000 dilution of HRP-coupled goat anti-mouse antibody (Southern Biotechnology Associates) for 1 hour. The blots were rinsed with TBS-Tween four times for five minutes each rinse and then developed using SuperSignal West Pico Chemiluminescent Substrate (Pierce Biotechnology) as directed by the manufacturer. Alternatively, blots can be developed using the Western Breeze™ Immunodetection Kit (Invitrogen).

The results of that experiment are shown in FIG. 49. Antibody 14D12 bound only to N-mANGPTL4 in that experiment. 14D12 did not appear to bind to any of the other fragments in that experiment. That result may be due to the fact that 14D12 is a weaker binder than 15F2 and 90B4. See, e.g., Example S and F1G. 33. Antibody 15F2 bound His-SUMO-gs1. That result suggests that 15F2 binds at least to a region between Q24 and P98 of mANGPTL4 (SEQ ID NO: 40). Antibody 90B4 bound to His-SUMO-gs2 and His-SUMO-gs4. That result suggests that the 90B4 epitope contains portions of mANGPTL4 between L49 and P98 (SEQ ID NO: 41) and between E99 and L151 (SEQ ID NO: 43).

BB. siRNA

Oligonucleotides for use as siRNAs were identified using the SMARTselection™ process (Dharmacon, Inc., Lafayette, Colo.). This process uses a multi-component algorithm for identifying siRNAs with a high probability of potent and specific degradation of the target mRNA. Four double stranded RNA oligonucleotides for use as siRNAs were identified using this process. The sequences of the four oligonucleotides are set forth in SEQ ID NOs:5-8.

The oligonucleotides are used to induce the degradation, and thus the expression, of mRNA encoding human ANGPTL4. The four oligonucleotides are combined within a single reagent, the SMARTpool® reagent (Dharmacon, Inc., Lafayette, Colo.), which is resuspended in a buffered RNase-free solution to a final concentration of about 20 μM. The oligonucleotides are transfected into cultured cells using standard transfection methods at a concentration of about 1-200 nM siRNA.

A cell-based assay is used to confirm that the oligonucleotides induce the degradation of mRNA encoding human ANGPTL4 in vitro. Hela cells transfected with the oligonucleotides are seeded onto 6-well plates and allowed to grow overnight in a 37° C. incubator with 5% CO$_2$ supplement. Seeding density is about 100,000 cells/well. The oligonucleotides are transfected into cells the next day at a final concentration of about 10-100 nM in 1 ml growth medium. Cells are harvested 48 hours after transfection. Total RNA is isolated using the Qiagen RNeasy kit. The amount of Angptl4 mRNA is analyzed by Northern blot analysis.

While the above examples describe, inter alia, certain neutralizing monoclonal antibodies against mouse ANGPTL4 and the in vivo effects of those antibodies in mice, one skilled in the art would readily recognize that neutralizing monoclonal antibodies against human ANGPTL4 may be generated, and such antibodies would have the same or similar in vivo effects in humans. That conclusion is based, in part, on the observation that human and mouse ANGPTL4 are evolutionarily conserved proteins that share structural and functional features. See, e.g., Ge et al. (2004) J. Biol. Chem. 279:2038-2045. For example, human and mouse ANGPTL4 share about 77% amino acid sequence identity. Human and mouse ANGPTL4 also share common secondary structural elements, e.g., an N-terminal coiled-coil domain and a C-terminal fibrinogen-like domain. Furthermore, human ANGPTL4 has a similar function as mouse ANGPTL4, as demonstrated by the ability of human ANGPTL4 to raise serum lipid levels when overexpressed in mice. See Part VI.B.2.

It is also generally recognized in the art that mice are routinely used as models for the treatment of various conditions and diseases using neutralizing antibodies. For example, neutralizing antibodies have been used to treat prion disease, diabetes, and inflammation in mice. See, e.g., White et al. (2003) *Nature* 422:80-83; Cailleau et al. (1997) *Diabetes* 46:937-940; and Lochner et al. (2002) *J. Immunol. Methods* 259:149-157. In the latter study, monoclonal antibodies that neutralize mouse IL-18 were raised in IL-18 deficient mice. Those mouse monoclonal antibodies were capable of suppressing lipopolysaccharide-induced inflammatory response in wild-type mice. Thus, one skilled in the art would conclude that the foregoing examples support the use of neutralizing monoclonal antibodies against human ANGPTL4 in the treatment of human medical conditions.

TABLE 6

Table of Sequences

| Description | SEQ ID NO: | Sequence |
|---|---|---|
| mouse ANGPTL4 (Accession No. NP_065606) | 1 | mrcaptagaa lvlcaatagl lsaqgrpaqp epprfaswde mnllahgllq lghglrehve rtrgqlgale rrmaacgnac qgpkgkdapf kdsedrvpeg qtpetlqslq tqlkaqnski qqlfqkvaqq qrylskqnlr iqnlqsqidl lapthldngv dktsrgkkls kmtqliglts nathlhrpar dcqelfqege rhsglfqiqp lgsppflvnc emtsdggwtv iqrrlngsvd fnqsweaykd gfgdpqgefw lglekmhsit gdrgsqlavq lqdwdgnakl lqfpihlgge dtayslqlte ptanelgatn vspnglslpf stwdqdhdlr gdlncaksls ggwwfgtcsh snlngqyfhs iprqrqerkk gifwktwkgr yyplqattll iqpmeataas |
| mouse ANGPTL4 (Swiss-Prot. Accession No. Q9Z1P8) | 50 | MRCAPTAGAA LVLCAATAGL LSAQGRPAQP EPPRFASWDE MNLLAHGLLQ LGHGLREHVE RTRGQLGALE RRMAACGNAC QGPKGKDAPF KDSEDRVPEG QTPETLQSLQ TQLKAQNSKI QQLFQKVAQQ QRYLSKQNLR IQNLQSQIDL LAPTHLDNGV DKTSRGKRLP KMTQLIGLTP NATHLHRPPR DCQELFQEGE RHSGLFQIQP LGSPPFLVNC EMTSDGGWTV IQRRLNGSVD FNQSWEAYKD GFGDPQGEFW LGLEKMHSIT GNRGSQLAVQ LQDWDGNAKL LQFPIHLGGE DTAYSLQLTE PTANELGATN VSPNGLSLPF STWDQDHDLR GDLNCAKSLS GGWWFGTCSH SNLNGQYFHS IPRQRQERKK GIFWKTWKGR YYPLQATTLL IQPMEATAAS |
| human ANGPTL4 (Accession No. NP_647475) | 2 | msgaptagaa lmlcaatavl lsaqggpvqs ksprfaswde mnvlahgllq lgqglrehae rtrsqlsale rrlsacgsac qgtegstdlp lapesrvdpe vlhslqtqlk aqnsriqqlf hkvaqqqrhl ekqhlriqhl qsqfglldhk hldhevakpa rrkrlpemaq pvdpahnvsr lhrlprdcqe lfqvgerqsg lfeiqpqgsp pflvnckmts dggwtviqrr hdgsvdfnrp weaykagfgd phgefwlgle kvhsitgdrn srlavqlrdw dgnaellqfs vhlggedtay slqltapvag qlgattvpps glsvpfstwd qdhdlrrdkn cakslsggww fgtcshsnln gqyfrsipqq rqklkkgifw ktwrgryypl qattmliqpm aaeaas |
| mouse Angptl4 (Accession No. NM_020581) (mRNA/cDNA) | 3 | gcaccagagc aagtctaagt ctgagccggc tcccccagaa ctccagctgc tgggtcttga actcctgcgt tccggagtcc tagcgttgct gcacccaagg ccaccccag aatcatgcgc tgcgctccga cagcaggcgc tgccctggtg ctatgcgcgg ctactgcggg gcttttgagc gctcaagggc gccctgcaca gccagagcca ccgcgctttg catcctggga cgagatgaac ttgctggctc acgggctgct acagctcggc catgggctgc gcgaacacgt ggagcgcacc cgtgggcagc tgggcgcgct ggagcgccgc atggctgcct gtggtaacgc ttgtcagggg cccaagggaa aagatgcacc cttcaaagac tccgaggata gagtccctga aggccagact cctgagactc tgcagagttt gcagactcag ctcaaggctc aaaacagcaa gatccagcaa ttgttccaga aggtggccca gcagcagaga tacctatcaa agcagaatct gagaatacag aatcttcaga gccagataga cctcttggcc cccacgcacc tggacaatgg agtagacaag acttcgaggg gaaagaagct ttccaagatg acccagctca ttggcttgac ttccaacgcc acccacttac acaggccggc ccgggactgc caggaactct tccaagaagg ggagaggcac agtggacttt tccagatcca gcctctgggg tctccaccat ttttggtcaa ctgtgagatg acttcagatg gaggctggac agtgattcag agacgcctga acggctctgt ggacttcaac cagtcctggg aagcctacaa ggatggcttc ggagatccca aaggcgagtt ctggctgggc ctggaaaaga tgcacagcat cacagggggac cgaggaagcc aattggctgt gcagctccag gactgggatg gcaatgccaa attgctccaa tttcccatcc atttgggggg tgaggacaca gcctacagcc tgcagctcac tgagcccacg gccaatgagc tgggtgccac caatgtttcc |

TABLE 6-continued

Table of Sequences

| Description | SEQ ID NO: | Sequence |
|---|---|---|
| | | cccaatggcc tttccctgcc cttctctact tgggaccaag<br>accatgacct ccgtggggac cttaactgtg ccaagagcct<br>ctctggtggc tggtggtttg gtacctgtag ccattccaat<br>ctcaatggac aatacttcca ctctatccca cggcaacggc<br>aggagcgtaa aaagggtatc ttctggaaaa catggaaggg<br>ccgctactat cctctgcagg ctaccaccct gttgatccag<br>cccatggagg ctacagcagc ctcttagcct cctcactgga<br>gcctggttcc aggcctaaga agacagtgac tttggttgtg<br>gccctgagat ttggccattc tctgctgggg gcaggagctc<br>taagtagggc tatctgcgtc ttgtggacaa agaagaagcc<br>cgtaactgga gagactggag gaccccttt ccgtgttggg<br>gtctgcaagc attgttgtct gaaacagtca gagcaacagg<br>aaacaaatgg cccagatcca gaaaacatgg gctcgagggg<br>cactgaatat cacttctcgc ctaccagaga agttggggat<br>gcagagggac cactacagtc caactagctg ggcccttaat<br>ggcggactca gtcatattga ctgactggag acagggtgcc<br>aggagccctg gatacactca tggtgctgtt gtaggtgctg<br>tggatgcaca ggtgctaact gtggttccca ggcacagctc<br>acagcattct tacaataaaa acaacctcag aacaaaacaa<br>aaaaaaaaaa aaaaaaaa |
| mouse Angptl4<br>(Accession No.<br>AF169313)<br>(mRNA/cDNA) | 49 | GTTCCGGAGT CCTAGCGTTG CTGCACCCAA GGCCACCCCC<br>AGAATCATGC GCTGCGCTCC GACAGCAGGC GCTGCCCTGG<br>TGCTATGCGC GGCTACTGCG GGGCTTTTGA GCGCGCAAGG<br>GCGCCCTGCA CAGCCAGAGC CACCGCGCTT TGCATCCTGG<br>GACGAGATGA ACTTGCTGGC TCACGGGCTG CTACAGCTCG<br>GCCATGGGCT GCGCGAACAC GTGGAGCGCA CCCGTGGGCA<br>GCTGGGCGCG CTGGAGCGCC GCATGGCTGC CTGTGGTAAC<br>GCTTGTCAGG GGCCCAAGGG AAAAGATGCA CCCTTCAAAG<br>ACTCCGAGGA TAGAGTCCCT GAAGGCCAGA CTCCTGAGAC<br>TCTGCAGAGT TTGCAGACTC AGCTCAAGGC TCAAAACAGC<br>AAGATCCAGC AATTGTTCCA GAAGGTGGCC CAGCAGCAGA<br>GATACCTATC AAAGCAGAAT CTGAGAATAC AGAATCTTCA<br>GAGCCAGATA GACCTCTTGG CCCCCACGCA CCTAGACAAT<br>GGAGTAGACA AGACTTCGAG GGGAAAGAGG CTTCCCAAGA<br>TGACCCAGCT CATTGGCTTG ACTCCCAACG CCACCCACTT<br>ACACAGGCCG CCCCGGGACT GCCAGGAACT CTTCCAAGAA<br>GGGGAGAGGC ACAGTGGACT TTTCCAGATC CAGCCTCTGG<br>GGTCTCCACC ATTTTTGGTC AACTGTGAGA TGACTTCAGA<br>TGGAGGCTGG ACAGTGATTC AGAGACGCCT GAACGGCTCT<br>GTGGACTTCA ACCAGTCCTG GGAAGCCTAC AAGGATGGCT<br>TCGGAGATCC CCAAGGCGAG TTCTGGCTGG GCCTGGAAAA<br>GATGCACAGC ATCACAGGGA ACCGAGGAAG CCAATTGGCT<br>GTGCAGCTCC AGGACTGGGA TGGCAATGCC AAATTGCTCC<br>AATTTCCCAT CCATTTGGGG GGTGAGGACA CAGCCTACAG<br>CCTGCAGCTC ACTGAGCCCA CGGCCAATGA GCTGGGTGCC<br>ACCAATGTTT CCCCCAATGG CCTTTCCCTG CCCTTCTCTA<br>CTTGGGACCA AGACCATGAC CTCCGTGGGG ACCTTAACTG<br>TGCCAAGAGC CTCTCTGGTG GCTGGTGGTT TGGTACCTGT<br>AGCCATTCCA ATCTCAATGG ACAATACTTC CACTCTATCC<br>CACGGCAACG GCAGGAGCGT AAAAAGGGTA TCTTCTGGAA<br>AACATGGAAG GGCCGCTACT ATCCTCTGCA GGCTACCACC<br>CTGCTGATCC AGCCCATGGA GGCTACAGCA GCCTCTTAGC<br>CTCCTCACTG GAGCCTGGTT CCAGGCTAAG AAG |
| human Angptl4<br>(Accession No.<br>NM_139314)<br>(mRNA/cDNA) | 4 | ataaaaaccg tcctcgggcg cggcggggag aagccgagct<br>gagcggatcc tcacacgact gtgatccgat tctttccagc<br>ggcttctgca accaagcggg tcttaccccc ggtcctccgc<br>gtctccagtc ctcgcacctg gaacccaac gtccccgaga<br>gtccccgaat ccccgctccc aggctaccta agaggatgag<br>cggtgctccg acggccgggg cagccctgat gctctgcgcc<br>gccaccgccg tgctactgag cgctcagggc ggacccgtgc<br>agtccaagtc gccgcgcttt gcgtcctggg acgagatgaa<br>tgtcctggcg cacggactcc tgcagctcgg ccaggggctg<br>cgcgaacacg cggagcgcac ccgcagtcag ctgagcgcgc<br>tggagcggcg cctgagcgcg tgcgggtccg cctgtcaggg<br>aaccgagggg tccaccgacc tcccgttagc ccctgagagc<br>cgggtggacc ctgaggtcct tcacagcctg cagacacaac<br>tcaaggctca gaacagcagg atccagcaac tcttccacaa<br>ggtggcccag cagcagcggc acctggagaa gcagcacctg<br>cgaattcagc atctgcaaag ccagtttggc ctcctggacc<br>acaagcacct agaccatgag gtggccaagc ctgcccgaag<br>aaagaggctg cccgagatgg cccagccagt tgacccggct<br>cacaatgtca gccgcctgca ccggctgccc agggattgcc<br>aggagctgtt ccaggttggg gagaggcaga gtggactatt |

TABLE 6-continued

Table of Sequences

| Description | SEQ ID NO: | Sequence |
|---|---|---|
| | | tgaaatccag cctcagggt ctccgccatt tttggtgaac<br>tgcaagatga cctcagatgg aggctggaca gtaattcaga<br>ggcgccacga tggctcagtg gacttcaacc ggccctggga<br>agcctacaag gcggggtttg gggatcccca cggcgagttc<br>tggctgggtc tggagaaggt gcatagcatc acgggggacc<br>gcaacagccg cctggccgtg cagctgcggg actgggatgg<br>caacgccgag ttgctgcagt ctccgtgca cctgggtggc<br>gaggacacgg cctatagcct gcagctcact gcacccgtgg<br>ccggccagct gggcgccacc accgtccac ccagcggcct<br>ctccgtaccc ttctccactt gggaccagga tcacgacctc<br>cgcagggaca agaactgcgc caagagcctc tctggaggct<br>ggtggtttgg cacctgcagc cattccaacc tcaacgcca<br>gtacttccgc tccatcccac agcagcggca gaagcttaag<br>aagggaatct tctggaagac ctggcggggc cgctactacc<br>cgctgcaggc caccaccatg ttgatccagc ccatggcagc<br>agaggcagcc tcctagcgtc ctggctgggc ctggtcccag<br>gcccacgaaa gacggtgact cttggctctg cccgaggatg<br>tggccgttcc ctgcctgggc aggggctcca aggaggggcc<br>atctggaaac ttgtggacag agaagaagac cacgactgga<br>gaagccccct ttctgagtgc aggggggctg catgcgttgc<br>ctcctgagat cgaggctgca ggatatgctc agactctaga<br>ggcgtggacc aaggggcatg gagcttcact ccttgctggc<br>cagggagttg gggactcaga gggaccactt ggggccagcc<br>agactggcct caatggcgga ctcagtcaca ttgactgacg<br>gggaccaggg cttgtgtggg tcgagagcgc cctcatggtg<br>ctggtgctgt tgtgtgtagg tccctgggg acacaagcag<br>gcgccaatgg tatctgggcg gagctcacag agttcttgga<br>ataaaagcaa cctcagaaca cttaaaaaaa aaaaaaaaaa<br>aaaaaaaaaa aaaaaaaaaa aaaaaaaaaa aaaaaaaaaa<br>aaaaaaa |
| oligo 1 for siRNA | 5 | GAGGCAGAGUGGACUAUUUUU |
| oligo 2 for siRNA | 6 | UUGGUGAACUGCAAGAUGAUU |
| oligo 3 for siRNA | 7 | GAUGGAGGCUGGACAGUAAUU |
| oligo 4 for siRNA | 8 | GACAAGAACUGCGCCAAGAUU |
| peptide that 4A8 was raised against | 9 | LAPTHLDNGVDKTSRGKR |
| N-mANGPTL4 | 10 | MAMDIGINSD PQGRPAQPEP PRFASWDEMN LLAHGLLQLG<br>HGLREHVERT RGQLGALERR MAACGNACQG PKGKDAPFKD<br>SEDRVPEGQT PETLQSLQTQ LKAQNSKIQQ LFQKVAQQQR<br>YLSKQNLRIQ NLQSQIDLLA PTHLDNGVDK TSRGKRLPKM<br>TQLIGLTPLE HHHHHH |
| N-hANGPTL4 | 11 | MAMDIGINSD PNSSQGGPV QSKSPRFASW DEMNVLAHGL<br>LQLGQGLREH AERTRSQLSA LERRLSACGS ACQGTEGSTD<br>LPLAPESRVD PEVLHSLQTQ LKAQNSRIQQ LFHKVAQQQR<br>HLEKQHLRIQ HLQSQFGLLD HKHLDHEVAK PARRKRLPEM<br>AQPVDPAHLE HHHHHH |
| 14D12 heavy chain variable region | 12 | MNFGLSLIFL VLILKGVQCE VKLVESGGGL VKPGGSLKLS<br>CAASGFAFSR YDMSWVRQTP EKRLEWVATI STGGSYTYYP<br>DSVKGRFTIS RDNARNTLYL QMGSLRSEDT ALYFCVRHEQ<br>STVVPHYPLD YWGQGTSVTV SSA |
| 15F2 heavy chain variable region | 13 | MNFGLSLIFL VLILKGVQCE VKLVESGGGL VKPGGSLKLS<br>CAASGFAFSR YDMSWVRQTP EKRLEWVATI STDGSYTYYP<br>DSVKGRFTIS RDNARNTLYL QMGSLRSEDT ALYFCVRHEQ<br>STIVPHYPLD YWGQGTSVTV SSA |
| 90B4 heavy chain variable region | 14 | MGWSWIFLFL LSETAGVLSE VQLQQSGPEL MKPGASVKMS<br>CRTSGYTFTD YSIHWVKQSH GKRLEWIGYI NPYNGDTYCD<br>QNFKGKATLT FNKASSTAYM EIPRLTSDDS AVYYCTRWKT<br>IQAPFAYWGQ GTLVTVSA |

TABLE 6-continued

Table of Sequences

| Description | SEQ ID NO: | Sequence |
|---|---|---|
| heavy chain variable region consensus | 15 | MNFGLSLIFL VLILKGVQCE VKLVESGGGL VKPGGSLKLS CAASGFAFSR YDMSWVRQTP EKRLEWVATI STXGSYTYYP DSVKGRFTIS RDNARNTLYL QMGSLRSEDT ALYFCVRHEQ STIVPHYPLD YWGQGTSVTV SSA |
| 14D12 light chain variable region | 16 | MVSTSQLLGL LLFWTSASRC DIVMTQSPAT LSVTPGDRVS LSCRASQSIG DYLHWYQQKS HESPRLLIKY ASQSISGIPS RFSGSGSGSD FTLSIDSVEP EDVGVYYCQN GHSFPFTFGS GTKLEIKR |
| 15F2 light chain variable region | 17 | MDMRAPAQFL GILLLWFPGA RCEIQMTQSP SSMSASLGDR ITITCQATQD IVKNLNWYQQ KPGKPPSFLI HYATELAEGV PSRFSGSGSG SDYSLTISNL ESEDFADYYC LQSYDFPYTF GGGTKLEINR |
| 90B4 light chain variable region | 18 | MDMRAPAQFL GILLLWFPGA RCEIQMTQSP SSMSASLGDR ITITCQATQD IVKNLNWYQQ KPGKPPSFLI HYATELAEGV PSRFSGSGSG SDYSLTISNL ESEDFADYYC LQSYDFPYTF GGGTKLEIN |
| light chain variable region consensus | 19 | RAPAQFLGIL LLWFPGARCE IQMTQSPSSM SASLGDRITI TCQATQDIVK NLNWYQQKPG KPPSFLIHYA TELAEGVPSR FSGSGSGSDY SLTISNLESE DFADYYCLQS YDFPYTFGGG TKLEINR |
| 14D12 heavy chain CDR1 | 21 | RYDMS |
| 14D12 heavy chain CDR2 | 22 | TISTGGSYTYYPDSVKG |
| 14D12 heavy chain CDR3 | 23 | RHEQSTVVPHYPL |
| 15F2 heavy chain CDR1 | 24 | RYDMS |
| 15F2 heavy chain CDR2 | 25 | TISTDGSYTYYPDSVKG |
| 15F2 heavy chain CDR3 | 26 | RHEQSTIVPHYPL |
| 90B4 heavy chain CDR1 | 27 | DYSIH |
| 90B4 heavy chain CDR2 | 28 | YINPYNGDTYCDQNFK |
| 90B4 heavy chain CDR3 | 29 | RWKTIQAPF |
| 14D12 light chain CDR1 | 30 | RASQSIGDYLH |
| 14D12 light chain CDR2 | 31 | YASQSIS |
| 14D12 light chain CDR3 | 32 | QNGHSFP |
| 15F2 light chain CDR1 | 33 | QATQDIVKNLN |
| 15F2 light chain CDR2 | 34 | YATELAE |
| 15F2 light chain CDR3 | 35 | LQSYDFP |
| 90B4 light chain CDR1 | 36 | QATQDIVKNLN |
| 90B4 light chain CDR2 | 37 | YATELAE |

TABLE 6-continued

Table of Sequences

| Description | SEQ ID NO: | Sequence |
|---|---|---|
| 90B4 light chain CDR3 | 38 | LQSYDFP |
| 14D12 and 15F2 heavy chain CDR2 consensus | 39 | TISTDXSYTYYPDSVKG |
| 14D12 and 15F2 heavy chain CDR3 consensus | 20 | RHEQSTXVPHYPL |
| gs-1 fragment of mANGPTL4 | 40 | QGRPAQPEPPRFASWDEMNLLAHGLLQLGHGLREHVE RTRGQLGALERRM |
| gs-2 fragment of mANGPTL4 | 41 | LQLGHGLREHVERTRGQLGALERRMAACGNAC QGPKGKDAPFKDSEDRVP |
| gs-3 fragment of mANGPTL4 | 42 | AACGNACQGPKGKDAPFKDSEDRVPEGQTPETLQSLQ TQLKAQNSKIQQL |
| gs4 fragment of mANGPTL4 | 43 | EGQTPETLQSLQTQLKAQNSKIQQLFQKVAQQ QRYLSKQNLRIQNLQSQIDLL |
| gs5 fragment of mANGPTL4 | 44 | FQKVAQQQRYLSKQNLRIQNLQSQIDLLAPTHLDNGV DKTSRGKRLPKMTQLIGLTP |
| gs1-2 fragment of mANGPTL4 | 45 | LQLGHGLREHVERTRGQLGALERRM |
| gs2-3 fragment of mANGPTL4 | 46 | AACGNACQGPKGKDAPFKDSEDRVP |
| gs3-4 fragment of mANGPTL4 | 47 | EGQTPETLQSLQTQLKAQNSKIQQL |
| gs 4-5 fragment of mANGPTL4 | 48 | FQKVAQQQRYLSKQNLRIQNLQSQIDLL |

The invention claimed is:

1. A monoclonal antibody comprising a heavy chain and a light chain, wherein the heavy chain comprises a first CDR1, a first CDR2, and a first CDR3, wherein the first CDR1 comprises an amino acid sequence as set forth in SEQ ID NO: 21, the first CDR2 comprises an amino acid sequence as set forth in SEQ ID NO: 22, and the first CDR3 comprises an amino acid sequence as set forth in SEQ ID NO: 23, and the light chain comprises a second CDR1, a second CDR2, and a second CDR3, wherein the second CDR1 comprises an amino acid sequence as set forth in SEQ ID NO: 30, the second CDR2 comprises an amino acid sequence as set forth in SEQ ID NO: 31, and the second CDR3 comprises a sequence as set forth in SEQ ID NO: 32.

2. The antibody of claim 1, wherein the antibody is a mouse antibody.

3. The antibody of claim 1, wherein the antibody is a humanized antibody.

4. The antibody of claim 1, wherein the antibody is a fragment selected from an scFv, a Fab, a Fab', and a (Fab')$_2$.

5. The antibody of claim 1, wherein the heavy chain comprises an amino acid sequence as set forth in SEQ ID NO: 12 and the light chain comprises an amino acid sequence as set forth in SEQ ID NO: 16.

6. A pharmaceutical composition comprising the antibody of claim 1 and at least one pharmaceutically acceptable ingredient selected from a diluent, a carrier, a solubilizer, an emulsifier, a preservative, and an adjuvant.

7. A monoclonal antibody comprising a heavy chain and a light chain, wherein the heavy chain comprises a first CDR1, a first CDR2, and a first CDR3, wherein the first CDR1 comprises an amino acid sequence as set forth in SEQ ID NO: 24, the first CDR2 comprises an amino acid sequence as set forth in SEQ ID NO: 25, and the first CDR3 comprises an amino acid sequence as set forth in SEQ ID NO: 26, and the light chain comprises a second CDR1, a second CDR2, and a second CDR3, wherein the second CDR1 comprises an amino acid sequence as set forth in SEQ ID NO: 33, the second CDR2 comprises an amino acid sequence as set forth in SEQ ID NO: 34, and the second CDR3 comprises an amino acid sequence as set forth in SEQ ID NO: 35.

8. The antibody of claim 7, wherein the heavy chain comprises an amino acid sequence as set forth in SEQ ID NO: 13 and the light chain comprises an amino acid sequence as set forth in SEQ ID NO: 17.

9. The antibody of claim 7, wherein the antibody is a mouse antibody.

10. The antibody of claim 7, wherein the antibody is a humanized antibody.

11. The antibody of claim 7, wherein the antibody is a fragment selected from an scFv, a Fab, a Fab', and a (Fab')$_2$.

12. A pharmaceutical composition comprising the antibody of claim 7 and at least one pharmaceutically acceptable ingredient selected from a diluent, a carrier, a solubilizer, an emulsifier, a preservative, and an adjuvant.

13. A monoclonal antibody comprising a heavy chain and a light chain, wherein the heavy chain comprises a first CDR1, a first CDR2, and a first CDR3, wherein the first CDR1 comprises an amino acid sequence as set forth in SEQ ID NO: 27, the first CDR2 comprises an amino acid sequence as set forth in SEQ ID NO: 28, and the first CDR3 comprises an amino acid sequence as set forth in SEQ ID NO: 29, and the light chain comprises a second CDR1, a second CDR2, and a second CDR3, wherein the second CDR1 comprises an amino acid sequence as set forth in SEQ ID NO: 36, the second CDR2 comprises an amino acid sequence as set forth in SEQ ID NO: 37, and the second CDR3 comprises an amino acid sequence as set forth in SEQ ID NO: 38.

14. The antibody of claim 13, wherein the heavy chain comprises an amino acid sequence as set forth in SEQ ID NO: 14 and the light chain comprises an amino acid sequence as set forth in SEQ ID NO: 18.

15. The antibody of claim 13, wherein the antibody is a mouse antibody.

16. The antibody of claim 13, wherein the antibody is a humanized antibody.

17. The antibody of claim 13, wherein the antibody is a fragment selected from an scFv, a Fab, a Fab', and a (Fab')$_2$.

18. A pharmaceutical composition comprising the antibody of claim 13 and at least one pharmaceutically acceptable ingredient selected from a diluent, a carrier, a solubilizer, an emulsifier, a preservative, and an adjuvant.

* * * * *

SEQUENCE LISTING

<160> NUMBER OF SEQ ID NOS: 50

<210> SEQ ID NO 1
<211> LENGTH: 410
<212> TYPE: PRT
<213> ORGANISM: Mus musculus

<400> SEQUENCE: 1

```
Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45

Leu Gln Leu Gly His Gly Leu Arg Glu His Val Glu Arg Thr Arg Gly
    50                  55                  60

Gln Leu Gly Ala Leu Glu Arg Met Ala Ala Cys Gly Asn Ala Cys
65                  70                  75                  80

Gln Gly Pro Lys Gly Lys Asp Ala Pro Phe Lys Asp Ser Glu Asp Arg
                85                  90                  95
```

-continued

Val Pro Glu Gly Gln Thr Pro Glu Thr Leu Gln Ser Leu Gln Thr Gln
            100                 105                 110

Leu Lys Ala Gln Asn Ser Lys Ile Gln Gln Leu Phe Gln Lys Val Ala
        115                 120                 125

Gln Gln Gln Arg Tyr Leu Ser Lys Gln Asn Leu Arg Ile Gln Asn Leu
    130                 135                 140

Gln Ser Gln Ile Asp Leu Leu Ala Pro Thr His Leu Asp Asn Gly Val
145                 150                 155                 160

Asp Lys Thr Ser Arg Gly Lys Lys Leu Ser Lys Met Thr Gln Leu Ile
                165                 170                 175

Gly Leu Thr Ser Asn Ala Thr His Leu His Arg Pro Ala Arg Asp Cys
            180                 185                 190

Gln Glu Leu Phe Gln Glu Gly Glu Arg His Ser Gly Leu Phe Gln Ile
        195                 200                 205

Gln Pro Leu Gly Ser Pro Pro Phe Leu Val Asn Cys Glu Met Thr Ser
    210                 215                 220

Asp Gly Gly Trp Thr Val Ile Gln Arg Arg Leu Asn Gly Ser Val Asp
225                 230                 235                 240

Phe Asn Gln Ser Trp Glu Ala Tyr Lys Asp Gly Phe Gly Asp Pro Gln
                245                 250                 255

Gly Glu Phe Trp Leu Gly Leu Glu Lys Met His Ser Ile Thr Gly Asp
            260                 265                 270

Arg Gly Ser Gln Leu Ala Val Gln Leu Gln Asp Trp Asp Gly Asn Ala
        275                 280                 285

Lys Leu Leu Gln Phe Pro Ile His Leu Gly Gly Glu Asp Thr Ala Tyr
    290                 295                 300

Ser Leu Gln Leu Thr Glu Pro Thr Ala Asn Glu Leu Gly Ala Thr Asn
305                 310                 315                 320

Val Ser Pro Asn Gly Leu Ser Leu Pro Phe Ser Thr Trp Asp Gln Asp
                325                 330                 335

His Asp Leu Arg Gly Asp Leu Asn Cys Ala Lys Ser Leu Ser Gly Gly
            340                 345                 350

Trp Trp Phe Gly Thr Cys Ser His Ser Asn Leu Asn Gly Gln Tyr Phe
        355                 360                 365

His Ser Ile Pro Arg Gln Arg Gln Glu Arg Lys Lys Gly Ile Phe Trp
    370                 375                 380

Lys Thr Trp Lys Gly Arg Tyr Tyr Pro Leu Gln Ala Thr Thr Leu Leu
385                 390                 395                 400

Ile Gln Pro Met Glu Ala Thr Ala Ala Ser
                405                 410

<210> SEQ ID NO 2
<211> LENGTH: 406
<212> TYPE: PRT
<213> ORGANISM: Homo sapiens

<400> SEQUENCE: 2

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

| | | | | | | | | | | | | | | | |
|---|---|---|---|---|---|---|---|---|---|---|---|---|---|---|---|
| Gln | Leu | Ser | Ala | Leu | Glu | Arg | Arg | Leu | Ser | Ala | Cys | Gly | Ser | Ala | Cys |
| 65 | | | | 70 | | | | 75 | | | | 80 | | | |
| Gln | Gly | Thr | Glu | Gly | Ser | Thr | Asp | Leu | Pro | Leu | Ala | Pro | Glu | Ser | Arg |
| | | | | 85 | | | | | 90 | | | | | 95 | |
| Val | Asp | Pro | Glu | Val | Leu | His | Ser | Leu | Gln | Thr | Gln | Leu | Lys | Ala | Gln |
| | | | 100 | | | | | 105 | | | | | 110 | | |
| Asn | Ser | Arg | Ile | Gln | Gln | Leu | Phe | His | Lys | Val | Ala | Gln | Gln | Gln | Arg |
| | | | 115 | | | | | 120 | | | | | 125 | | |
| His | Leu | Glu | Lys | Gln | His | Leu | Arg | Ile | Gln | His | Leu | Gln | Ser | Gln | Phe |
| | 130 | | | | | 135 | | | | | 140 | | | | |
| Gly | Leu | Leu | Asp | His | Lys | His | Leu | Asp | His | Glu | Val | Ala | Lys | Pro | Ala |
| 145 | | | | | 150 | | | | | 155 | | | | | 160 |
| Arg | Arg | Lys | Arg | Leu | Pro | Glu | Met | Ala | Gln | Pro | Val | Asp | Pro | Ala | His |
| | | | | 165 | | | | | 170 | | | | | 175 | |
| Asn | Val | Ser | Arg | Leu | His | Arg | Leu | Pro | Arg | Asp | Cys | Gln | Glu | Leu | Phe |
| | | | 180 | | | | | 185 | | | | | 190 | | |
| Gln | Val | Gly | Glu | Arg | Gln | Ser | Gly | Leu | Phe | Glu | Ile | Gln | Pro | Gln | Gly |
| | | | 195 | | | | | 200 | | | | | 205 | | |
| Ser | Pro | Pro | Phe | Leu | Val | Asn | Cys | Lys | Met | Thr | Ser | Asp | Gly | Gly | Trp |
| | 210 | | | | | 215 | | | | | 220 | | | | |
| Thr | Val | Ile | Gln | Arg | Arg | His | Asp | Gly | Ser | Val | Asp | Phe | Asn | Arg | Pro |
| 225 | | | | | 230 | | | | | 235 | | | | | 240 |
| Trp | Glu | Ala | Tyr | Lys | Ala | Gly | Phe | Gly | Asp | Pro | His | Gly | Glu | Phe | Trp |
| | | | | 245 | | | | | 250 | | | | | 255 | |
| Leu | Gly | Leu | Glu | Lys | Val | His | Ser | Ile | Thr | Gly | Asp | Arg | Asn | Ser | Arg |
| | | | 260 | | | | | 265 | | | | | 270 | | |
| Leu | Ala | Val | Gln | Leu | Arg | Asp | Trp | Asp | Gly | Asn | Ala | Glu | Leu | Leu | Gln |
| | | | 275 | | | | | 280 | | | | | 285 | | |
| Phe | Ser | Val | His | Leu | Gly | Gly | Glu | Asp | Thr | Ala | Tyr | Ser | Leu | Gln | Leu |
| | 290 | | | | | 295 | | | | | 300 | | | | |
| Thr | Ala | Pro | Val | Ala | Gly | Gln | Leu | Gly | Ala | Thr | Thr | Val | Pro | Pro | Ser |
| 305 | | | | | 310 | | | | | 315 | | | | | 320 |
| Gly | Leu | Ser | Val | Pro | Phe | Ser | Thr | Trp | Asp | Gln | Asp | His | Asp | Leu | Arg |
| | | | | 325 | | | | | 330 | | | | | 335 | |
| Arg | Asp | Lys | Asn | Cys | Ala | Lys | Ser | Leu | Ser | Gly | Gly | Trp | Trp | Phe | Gly |
| | | | 340 | | | | | 345 | | | | | 350 | | |
| Thr | Cys | Ser | His | Ser | Asn | Leu | Asn | Gly | Gln | Tyr | Phe | Arg | Ser | Ile | Pro |
| | | | 355 | | | | | 360 | | | | | 365 | | |
| Gln | Gln | Arg | Gln | Lys | Leu | Lys | Lys | Gly | Ile | Phe | Trp | Lys | Thr | Trp | Arg |
| | 370 | | | | | 375 | | | | | 380 | | | | |
| Gly | Arg | Tyr | Tyr | Pro | Leu | Gln | Ala | Thr | Thr | Met | Leu | Ile | Gln | Pro | Met |
| 385 | | | | | 390 | | | | | 395 | | | | | 400 |
| Ala | Ala | Glu | Ala | Ala | Ser | | | | | | | | | | |
| | | | | 405 | | | | | | | | | | | |

<210> SEQ ID NO 3
<211> LENGTH: 1858
<212> TYPE: DNA
<213> ORGANISM: Mus musculus

<400> SEQUENCE: 3
gcaccagagc aagtctaagt ctgagccggc tcccccagaa ctccagctgc tgggtcttga    60
actcctgcgt tccggagtcc tagcgttgct gcacccaagg ccaccccag aatcatgcgc    120 tgcgctccga cagcaggcgc tgccctggtg ctatgcgcgg ctactgcggg gcttttgagc    180

```
gctcaagggc gccctgcaca gccagagcca ccgcgctttg catcctggga cgagatgaac    240
ttgctggctc acgggctgct acagctcggc catgggctgc gcgaacacgt ggagcgcacc    300
cgtgggcagc tgggcgcgct ggagcgccgc atggctgcct gtggtaacgc ttgtcagggg    360
cccaagggaa aagatgcacc cttcaaagac tccgaggata gagtccctga aggccagact    420
cctgagactc tgcagagttt gcagactcag ctcaaggctc aaaacagcaa gatccagcaa    480
ttgttccaga aggtggccca gcagcagaga tacctatcaa agcagaatct gagaatacag    540
aatcttcaga gccagataga cctcttggcc cccacgcacc tggacaatgg agtagacaag    600
acttcgaggg gaaagaagct ttccaagatg acccagctca ttggcttgac ttccaacgcc    660
acccacttac acaggccggc ccgggactgc caggaactct tccaagaagg ggagaggcac    720
agtggacttt tccagatcca gcctctgggg tctccaccat ttttggtcaa ctgtgagatg    780
acttcagatg gaggctggac agtgattcag agacgcctga acggctctgt ggacttcaac    840
cagtcctggg aagcctacaa ggatggcttc ggagatcccc aaggcgagtt ctggctgggc    900
ctggaaaaga tgcacagcat cacaggggac cgaggaagcc aattggctgt gcagctccag    960
gactgggatg gcaatgccaa attgctccaa tttcccatcc atttgggggg tgaggacaca   1020
gcctacagcc tgcagctcac tgagcccacg gccaatgagc tgggtgccac caatgtttcc   1080
cccaatggcc tttccctgcc cttctctact tgggaccaag accatgacct ccgtggggac   1140
cttaactgtg ccaagagcct ctctggtggc tggtggtttg gtacctgtag ccattccaat   1200
ctcaatggac aatacttcca ctctatccca cggcaacggc aggagcgtaa aaagggtatc   1260
ttctggaaaa catggaaggg ccgctactat cctctgcagg ctaccaccct gttgatccag   1320
cccatggagg ctacagcagc ctcttagcct cctcactgga gcctggttcc aggcctaaga   1380
agacagtgac tttggttgtg gccctgagat ttggccattc tctgctgggg gcaggagctc   1440
taagtagggc tatctgcgtc ttgtggacaa agaagaagcc cgtaactgga gagactggag   1500 gaccccttt ccgtgttggg gtctgcaagc attgttgtct gaaacagtca gagcaacagg   1560
aaacaaatgg cccagatcca gaaaacatgg gctcgagggg cactgaatat cacttctcgc   1620
ctaccagaga agttggggat gcagagggac cactacagtc caactagctg ggcccttaat   1680
ggcggactca gtcatattga ctgactggag acagggtgcc aggagccctg gatacactca   1740
tggtgctgtt gtaggtgctg tggatgcaca ggtgctaact gtggttccca ggcacagctc   1800
acagcattct tacaataaaa acaacctcag aacaaaacaa aaaaaaaaa aaaaaaa      1858
```

<210> SEQ ID NO 4
<211> LENGTH: 1967
<212> TYPE: DNA
<213> ORGANISM: Homo sapiens

<400> SEQUENCE: 4

```
ataaaaaccg tcctcgggcg cggcggggag aagccgagct gagcggatcc tcacacgact     60
gtgatccgat tctttccagc ggcttctgca accaagcggg tcttacccccc ggtcctccgc    120 gtctccagtc ctcgcacctg aaccccaacg tccccgaga gtcccgaat cccgctccc      180 aggctaccta agaggatgag cggtgctccg acggccgggg cagccctgat gctctgcgcc    240
gccaccgccg tgctactgag cgctcagggc ggacccgtgc agtccaagtc gccgcgcttt    300
gcgtcctggg acgagatgaa tgtcctggcg cacggactcc tgcagctcgg ccaggggctg    360
cgcgaacacg cggagcgcac ccgcagtcag ctgagcgcgc tggagcggcg cctgagcgcg    420
tgcgggtccg cctgtcaggg aaccgagggg tccaccgacc tcccgttagc ccctgagagc    480
```

```
cgggtggacc ctgaggtcct tcacagcctg cagacacaac tcaaggctca gaacagcagg    540
atccagcaac tcttccacaa ggtgcccag cagcagcggc acctggagaa gcagcacctg    600
cgaattcagc atctgcaaag ccagtttggc ctcctggacc acaagcacct agaccatgag    660
gtggccaagc ctgcccgaag aaagaggctg cccgagatgg cccagccagt tgacccggct    720
cacaatgtca gccgcctgca ccggctgccc agggattgcc aggagctgtt ccaggttggg    780
gagaggcaga gtggactatt tgaaatccag cctcaggggt ctccgccatt tttggtgaac    840
tgcaagatga cctcagatgg aggctggaca gtaattcaga ggcgccacga tggctcagtg    900
gacttcaacc ggccctggga agcctacaag gcggggtttg ggatcccca cggcgagttc    960 tggctgggtc tggagaaggt gcatagcatc acggggacc gcaacagccg cctggccgtg   1020
cagctgcggg actgggatgg caacgccgag ttgctgcagt tctccgtgca cctgggtggc   1080
gaggacacgg cctatagcct gcagctcact gcacccgtgg ccggccagct gggcgccacc   1140
accgtcccac ccagcggcct ctccgtaccc ttctccactt gggaccagga tcacgacctc   1200
cgcagggaca agaactgcgc caagagcctc tctggaggct ggtggtttgg cacctgcagc   1260
cattccaacc tcaacggcca gtacttccgc tccatcccac agcagcggca gaagcttaag   1320
aagggaatct tctgaaagac ctggcggggc cgctactacc cgctgcaggc caccaccatg   1380
ttgatccagc ccatggcagc agaggcagcc tcctagcgtc ctggctgggc ctggtcccag   1440
gcccacgaaa gacggtgact cttggctctg cccgaggatg tggccgttcc ctgcctgggc   1500
aggggctcca aggaggggcc atctggaaac ttgtggacag agaagaagac cacgactgga   1560
gaagccccct ttctgagtgc aggggggctg catgcgttgc ctcctgagat cgaggctgca   1620
ggatatgctc agactctaga ggcgtggacc aaggggcatg gagcttcact ccttgctggc   1680
cagggagttg gggactcaga gggaccactt ggggccagcc agactggcct caatggcgga   1740
ctcagtcaca ttgactgacg gggaccaggg cttgtgtggg tcgagagcgc cctcatggtg   1800
ctggtgctgt tgtgtgtagg tcccctgggg acacaagcag gcgccaatgg tatctgggcg   1860
gagctcacag agttcttgga ataaaagcaa cctcagaaca cttaaaaaaa aaaaaaaaa    1920 aaaaaaaaaa aaaaaaaaaa aaaaaaaaaa aaaaaaaaaa aaaaaaa                 1967

<210> SEQ ID NO 5
<211> LENGTH: 21
<212> TYPE: RNA
<213> ORGANISM: Artificial
<220> FEATURE:
<223> OTHER INFORMATION: Oligonucleotide for siRNA

<400> SEQUENCE: 5
gaggcagagu ggacuauuuu u                                               21

<210> SEQ ID NO 6
<211> LENGTH: 21
<212> TYPE: RNA
<213> ORGANISM: Artificial
<220> FEATURE:
<223> OTHER INFORMATION: oligonucleotide for siRNA

<400> SEQUENCE: 6
uuggugaacu gcaagaugau u                                               21

<210> SEQ ID NO 7
<211> LENGTH: 21
<212> TYPE: RNA
<213> ORGANISM: Artificial
<220> FEATURE:
```

-continued

<223> OTHER INFORMATION: oligonucleotide for siRNA

<400> SEQUENCE: 7
gauggaggcu ggacaguaau u                                                  21

<210> SEQ ID NO 8
<211> LENGTH: 21
<212> TYPE: RNA
<213> ORGANISM: Artificial
<220> FEATURE:
<223> OTHER INFORMATION: oligonucleotide for siRNA

<400> SEQUENCE: 8
gacaagaacu gcgccaagau u                                                  21

<210> SEQ ID NO 9
<211> LENGTH: 18
<212> TYPE: PRT
<213> ORGANISM: Artificial
<220> FEATURE:
<223> OTHER INFORMATION: peptide for immunization

<400> SEQUENCE: 9

Leu Ala Pro Thr His Leu Asp Asn Gly Val Asp Lys Thr Ser Arg Gly
1               5                   10                  15

Lys Arg

<210> SEQ ID NO 10
<211> LENGTH: 176
<212> TYPE: PRT
<213> ORGANISM: Artificial
<220> FEATURE:
<223> OTHER INFORMATION: fusion protein

<400> SEQUENCE: 10

Met Ala Met Asp Ile Gly Ile Asn Ser Asp Pro Gln Gly Arg Pro Ala
1               5                   10                  15

Gln Pro Glu Pro Pro Arg Phe Ala Ser Trp Asp Glu Met Asn Leu Leu
            20                  25                  30

Ala His Gly Leu Leu Gln Leu Gly His Gly Leu Arg Glu His Val Glu
        35                  40                  45

Arg Thr Arg Gly Gln Leu Gly Ala Leu Glu Arg Met Ala Ala Cys
    50                  55                  60

Gly Asn Ala Cys Gln Gly Pro Lys Gly Lys Asp Ala Pro Phe Lys Asp
65                  70                  75                  80

Ser Glu Asp Arg Val Pro Glu Gly Gln Thr Pro Glu Thr Leu Gln Ser
                85                  90                  95

Leu Gln Thr Gln Leu Lys Ala Gln Asn Ser Lys Ile Gln Gln Leu Phe
            100                 105                 110

Gln Lys Val Ala Gln Gln Arg Tyr Leu Ser Lys Gln Asn Leu Arg
        115                 120                 125

Ile Gln Asn Leu Gln Ser Gln Ile Asp Leu Leu Ala Pro Thr His Leu
    130                 135                 140

Asp Asn Gly Val Asp Lys Thr Ser Arg Gly Lys Arg Leu Pro Lys Met
145                 150                 155                 160

Thr Gln Leu Ile Gly Leu Thr Pro Leu Glu His His His His His His
                165                 170                 175

<210> SEQ ID NO 11
<211> LENGTH: 176
<212> TYPE: PRT

<213> ORGANISM: Artificial
<220> FEATURE:
<223> OTHER INFORMATION: fusion protein

<400> SEQUENCE: 11

Met Ala Met Asp Ile Gly Ile Asn Ser Asp Pro Asn Ser Ser Ser Gln
1               5                   10                  15

Gly Gly Pro Val Gln Ser Lys Ser Pro Arg Phe Ala Ser Trp Asp Glu
            20                  25                  30

Met Asn Val Leu Ala His Gly Leu Leu Gln Leu Gly Gln Gly Leu Arg
        35                  40                  45

Glu His Ala Glu Arg Thr Arg Ser Gln Leu Ser Ala Leu Glu Arg Arg
    50                  55                  60

Leu Ser Ala Cys Gly Ser Ala Cys Gln Gly Thr Glu Gly Ser Thr Asp
65                  70                  75                  80

Leu Pro Leu Ala Pro Glu Ser Arg Val Asp Pro Glu Val Leu His Ser
                85                  90                  95

Leu Gln Thr Gln Leu Lys Ala Gln Asn Ser Arg Ile Gln Gln Leu Phe
            100                 105                 110

His Lys Val Ala Gln Gln Arg His Leu Glu Lys Gln His Leu Arg
        115                 120                 125

Ile Gln His Leu Gln Ser Gln Phe Gly Leu Leu Asp His Lys His Leu
    130                 135                 140

Asp His Glu Val Ala Lys Pro Ala Arg Arg Lys Arg Leu Pro Glu Met
145                 150                 155                 160

Ala Gln Pro Val Asp Pro Ala His Leu Glu His His His His His His
                165                 170                 175

<210> SEQ ID NO 12
<211> LENGTH: 143
<212> TYPE: PRT
<213> ORGANISM: Mus musculus

<400> SEQUENCE: 12

Met Asn Phe Gly Leu Ser Leu Ile Phe Leu Val Leu Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Ala Phe
        35                  40                  45

Ser Arg Tyr Asp Met Ser Trp Val Arg Gln Thr Pro Glu Lys Arg Leu
    50                  55                  60

Glu Trp Val Ala Thr Ile Ser Thr Gly Gly Ser Tyr Thr Tyr Tyr Pro
65                  70                  75                  80

Asp Ser Val Lys Gly Arg Phe Thr Ile Ser Arg Asp Asn Ala Arg Asn
                85                  90                  95

Thr Leu Tyr Leu Gln Met Gly Ser Leu Arg Ser Glu Asp Thr Ala Leu
            100                 105                 110

Tyr Phe Cys Val Arg His Glu Gln Ser Thr Val Val Pro His Tyr Pro
        115                 120                 125

Leu Asp Tyr Trp Gly Gln Gly Thr Ser Val Thr Val Ser Ser Ala
    130                 135                 140

<210> SEQ ID NO 13
<211> LENGTH: 143
<212> TYPE: PRT
<213> ORGANISM: Mus musculus -continued

<400> SEQUENCE: 13

Met Asn Phe Gly Leu Ser Leu Ile Phe Leu Val Leu Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Ala Phe
        35                  40                  45

Ser Arg Tyr Asp Met Ser Trp Val Arg Gln Thr Pro Glu Lys Arg Leu
    50                  55                  60

Glu Trp Val Ala Thr Ile Ser Thr Asp Gly Ser Tyr Thr Tyr Tyr Pro
65                  70                  75                  80

Asp Ser Val Lys Gly Arg Phe Thr Ile Ser Arg Asp Asn Ala Arg Asn
                85                  90                  95

Thr Leu Tyr Leu Gln Met Gly Ser Leu Arg Ser Glu Asp Thr Ala Leu
            100                 105                 110

Tyr Phe Cys Val Arg His Glu Gln Ser Thr Ile Val Pro His Tyr Pro
        115                 120                 125

Leu Asp Tyr Trp Gly Gln Gly Thr Ser Val Thr Val Ser Ser Ala
    130                 135                 140

<210> SEQ ID NO 14
<211> LENGTH: 138
<212> TYPE: PRT
<213> ORGANISM: Mus musculus

<400> SEQUENCE: 14

Met Gly Trp Ser Trp Ile Phe Leu Phe Leu Leu Ser Glu Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Arg Thr Ser Gly Tyr Thr Phe
        35                  40                  45

Thr Asp Tyr Ser Ile His Trp Val Lys Gln Ser His Gly Lys Arg Leu
    50                  55                  60

Glu Trp Ile Gly Tyr Ile Asn Pro Tyr Asn Gly Asp Thr Tyr Cys Asp
65                  70                  75                  80

Gln Asn Phe Lys Gly Lys Ala Thr Leu Thr Phe Asn Lys Ala Ser Ser
                85                  90                  95

Thr Ala Tyr Met Glu Ile Pro Arg Leu Thr Ser Asp Asp Ser Ala Val
            100                 105                 110

Tyr Tyr Cys Thr Arg Trp Lys Thr Ile Gln Ala Pro Phe Ala Tyr Trp
        115                 120                 125

Gly Gln Gly Thr Leu Val Thr Val Ser Ala
    130                 135

<210> SEQ ID NO 15
<211> LENGTH: 143
<212> TYPE: PRT
<213> ORGANISM: Mus musculus
<220> FEATURE:
<221> NAME/KEY: misc_feature
<222> LOCATION: (73)..(73)
<223> OTHER INFORMATION: Xaa can be any naturally occurring amino acid

<400> SEQUENCE: 15

Met Asn Phe Gly Leu Ser Leu Ile Phe Leu Val Leu Ile Leu Lys Gly
1               5                   10                  15

Val Gln Cys Glu Val Lys Leu Val Glu Ser Gly Gly Gly Leu Val Lys

```
                    20                  25                  30
Pro Gly Gly Ser Leu Lys Leu Ser Cys Ala Ala Ser Gly Phe Ala Phe
                35                  40                  45

Ser Arg Tyr Asp Met Ser Trp Val Arg Gln Thr Pro Glu Lys Arg Leu
    50                  55                  60

Glu Trp Val Ala Thr Ile Ser Thr Xaa Gly Ser Tyr Thr Tyr Tyr Pro
65                  70                  75                  80

Asp Ser Val Lys Gly Arg Phe Thr Ile Ser Arg Asp Asn Ala Arg Asn
                85                  90                  95

Thr Leu Tyr Leu Gln Met Gly Ser Leu Arg Ser Glu Asp Thr Ala Leu
                100                 105                 110

Tyr Phe Cys Val Arg His Glu Gln Ser Thr Ile Val Pro His Tyr Pro
                115                 120                 125

Leu Asp Tyr Trp Gly Gln Gly Thr Ser Val Thr Val Ser Ser Ala
                130                 135                 140

<210> SEQ ID NO 16
<211> LENGTH: 128
<212> TYPE: PRT
<213> ORGANISM: Mus musculus

<400> SEQUENCE: 16

Met Val Ser Thr Ser Gln Leu Leu Gly Leu Leu Leu Phe Trp Thr Ser
1               5                   10                  15

Ala Ser Arg Cys Asp Ile Val Met Thr Gln Ser Pro Ala Thr Leu Ser
                20                  25                  30

Val Thr Pro Gly Asp Arg Val Ser Leu Ser Cys Arg Ala Ser Gln Ser
                35                  40                  45

Ile Gly Asp Tyr Leu His Trp Tyr Gln Gln Lys Ser His Glu Ser Pro
            50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asp
                85                  90                  95

Ser Val Glu Pro Glu Asp Val Gly Val Tyr Tyr Cys Gln Asn Gly His
                100                 105                 110

Ser Phe Pro Phe Thr Phe Gly Ser Gly Thr Lys Leu Glu Ile Lys Arg
                115                 120                 125

<210> SEQ ID NO 17
<211> LENGTH: 130
<212> TYPE: PRT
<213> ORGANISM: Mus musculus

<400> SEQUENCE: 17

Met Asp Met Arg Ala Pro Ala Gln Phe Leu Gly Ile Leu Leu Leu Trp
1               5                   10                  15

Phe Pro Gly Ala Arg Cys Glu Ile Gln Met Thr Gln Ser Pro Ser Ser
                20                  25                  30

Met Ser Ala Ser Leu Gly Asp Arg Ile Thr Ile Thr Cys Gln Ala Thr
                35                  40                  45

Gln Asp Ile Val Lys Asn Leu Asn Trp Tyr Gln Gln Lys Pro Gly Lys
            50                  55                  60

Pro Pro Ser Phe Leu Ile His Tyr Ala Thr Glu Leu Ala Glu Gly Val
65                  70                  75                  80

Pro Ser Arg Phe Ser Gly Ser Gly Ser Gly Ser Asp Tyr Ser Leu Thr
                85                  90                  95
```

Ile Ser Asn Leu Glu Ser Glu Asp Phe Ala Asp Tyr Tyr Cys Leu Gln
            100                 105                 110

Ser Tyr Asp Phe Pro Tyr Thr Phe Gly Gly Gly Thr Lys Leu Glu Ile
            115                 120                 125

Asn Arg
    130

<210> SEQ ID NO 18
<211> LENGTH: 129
<212> TYPE: PRT
<213> ORGANISM: Mus musculus

<400> SEQUENCE: 18

Met Asp Met Arg Ala Pro Ala Gln Phe Leu Gly Ile Leu Leu Leu Trp
1               5                   10                  15

Phe Pro Gly Ala Arg Cys Glu Ile Gln Met Thr Gln Ser Pro Ser Ser
            20                  25                  30

Met Ser Ala Ser Leu Gly Asp Arg Ile Thr Ile Thr Cys Gln Ala Thr
        35                  40                  45

Gln Asp Ile Val Lys Asn Leu Asn Trp Tyr Gln Lys Pro Gly Lys
 50                 55                  60

Pro Pro Ser Phe Leu Ile His Tyr Ala Thr Glu Leu Ala Glu Gly Val
65                  70                  75                  80

Pro Ser Arg Phe Ser Gly Ser Gly Ser Gly Ser Asp Tyr Ser Leu Thr
                85                  90                  95

Ile Ser Asn Leu Glu Ser Glu Asp Phe Ala Asp Tyr Tyr Cys Leu Gln
            100                 105                 110

Ser Tyr Asp Phe Pro Tyr Thr Phe Gly Gly Gly Thr Lys Leu Glu Ile
            115                 120                 125

Asn

<210> SEQ ID NO 19
<211> LENGTH: 127
<212> TYPE: PRT
<213> ORGANISM: Mus musculus

<400> SEQUENCE: 19

Arg Ala Pro Ala Gln Phe Leu Gly Ile Leu Leu Leu Trp Phe Pro Gly
1               5                   10                  15

Ala Arg Cys Glu Ile Gln Met Thr Gln Ser Pro Ser Ser Met Ser Ala
            20                  25                  30

Ser Leu Gly Asp Arg Ile Thr Ile Thr Cys Gln Ala Thr Gln Asp Ile
        35                  40                  45

Val Lys Asn Leu Asn Trp Tyr Gln Gln Lys Pro Gly Lys Pro Pro Ser
 50                 55                  60

Phe Leu Ile His Tyr Ala Thr Glu Leu Ala Glu Gly Val Pro Ser Arg
65                  70                  75                  80

Phe Ser Gly Ser Gly Ser Gly Ser Asp Tyr Ser Leu Thr Ile Ser Asn
                85                  90                  95

Leu Glu Ser Glu Asp Phe Ala Asp Tyr Tyr Cys Leu Gln Ser Tyr Asp
            100                 105                 110

Phe Pro Tyr Thr Phe Gly Gly Gly Thr Lys Leu Glu Ile Asn Arg
            115                 120                 125

<210> SEQ ID NO 20
<211> LENGTH: 13
<212> TYPE: PRT

```
<213> ORGANISM: Mus musculus
<220> FEATURE:
<221> NAME/KEY: misc_feature
<222> LOCATION: (7)..(7)
<223> OTHER INFORMATION: Xaa can be any naturally occurring amino acid

<400> SEQUENCE: 20

Arg His Glu Gln Ser Thr Xaa Val Pro His Tyr Pro Leu
1               5                   10

<210> SEQ ID NO 21
<211> LENGTH: 5
<212> TYPE: PRT
<213> ORGANISM: Mus musculus

<400> SEQUENCE: 21

Arg Tyr Asp Met Ser
1               5

<210> SEQ ID NO 22
<211> LENGTH: 17
<212> TYPE: PRT
<213> ORGANISM: Mus musculus

<400> SEQUENCE: 22

Thr Ile Ser Thr Gly Gly Ser Tyr Thr Tyr Tyr Pro Asp Ser Val Lys
1               5                   10                  15

Gly

<210> SEQ ID NO 23
<211> LENGTH: 13
<212> TYPE: PRT
<213> ORGANISM: Mus musculus

<400> SEQUENCE: 23

Arg His Glu Gln Ser Thr Val Val Pro His Tyr Pro Leu
1               5                   10

<210> SEQ ID NO 24
<211> LENGTH: 5
<212> TYPE: PRT
<213> ORGANISM: Mus musculus

<400> SEQUENCE: 24

Arg Tyr Asp Met Ser
1               5

<210> SEQ ID NO 25
<211> LENGTH: 17
<212> TYPE: PRT
<213> ORGANISM: Mus musculus

<400> SEQUENCE: 25

Thr Ile Ser Thr Asp Gly Ser Tyr Thr Tyr Tyr Pro Asp Ser Val Lys
1               5                   10                  15

Gly

<210> SEQ ID NO 26
<211> LENGTH: 13
<212> TYPE: PRT
<213> ORGANISM: Mus musculus

<400> SEQUENCE: 26

Arg His Glu Gln Ser Thr Ile Val Pro His Tyr Pro Leu
1               5                   10
```

<210> SEQ ID NO 27
<211> LENGTH: 5
<212> TYPE: PRT
<213> ORGANISM: Mus musculus

<400> SEQUENCE: 27

Asp Tyr Ser Ile His
1               5

<210> SEQ ID NO 28
<211> LENGTH: 16
<212> TYPE: PRT
<213> ORGANISM: Mus musculus

<400> SEQUENCE: 28

Tyr Ile Asn Pro Tyr Asn Gly Asp Thr Tyr Cys Asp Gln Asn Phe Lys
1               5                   10                  15

<210> SEQ ID NO 29
<211> LENGTH: 9
<212> TYPE: PRT
<213> ORGANISM: Mus musculus

<400> SEQUENCE: 29

Arg Trp Lys Thr Ile Gln Ala Pro Phe
1               5

<210> SEQ ID NO 30
<211> LENGTH: 11
<212> TYPE: PRT
<213> ORGANISM: Mus musculus

<400> SEQUENCE: 30

Arg Ala Ser Gln Ser Ile Gly Asp Tyr Leu His
1               5                   10

<210> SEQ ID NO 31
<211> LENGTH: 7
<212> TYPE: PRT
<213> ORGANISM: Mus musculus

<400> SEQUENCE: 31

Tyr Ala Ser Gln Ser Ile Ser
1               5

<210> SEQ ID NO 32
<211> LENGTH: 7
<212> TYPE: PRT
<213> ORGANISM: Mus musculus

<400> SEQUENCE: 32

Gln Asn Gly His Ser Phe Pro
1               5

<210> SEQ ID NO 33
<211> LENGTH: 11
<212> TYPE: PRT
<213> ORGANISM: Mus musculus

<400> SEQUENCE: 33

Gln Ala Thr Gln Asp Ile Val Lys Asn Leu Asn
1               5                   10

<210> SEQ ID NO 34

```
<211> LENGTH: 7
<212> TYPE: PRT
<213> ORGANISM: Mus musculus

<400> SEQUENCE: 34

Tyr Ala Thr Glu Leu Ala Glu
1               5

<210> SEQ ID NO 35
<211> LENGTH: 7
<212> TYPE: PRT
<213> ORGANISM: Mus musculus

<400> SEQUENCE: 35

Leu Gln Ser Tyr Asp Phe Pro
1               5

<210> SEQ ID NO 36
<211> LENGTH: 11
<212> TYPE: PRT
<213> ORGANISM: Mus musculus

<400> SEQUENCE: 36

Gln Ala Thr Gln Asp Ile Val Lys Asn Leu Asn
1               5                   10

<210> SEQ ID NO 37
<211> LENGTH: 7
<212> TYPE: PRT
<213> ORGANISM: Mus musculus

<400> SEQUENCE: 37

Tyr Ala Thr Glu Leu Ala Glu
1               5

<210> SEQ ID NO 38
<211> LENGTH: 7
<212> TYPE: PRT
<213> ORGANISM: Mus musculus

<400> SEQUENCE: 38

Leu Gln Ser Tyr Asp Phe Pro
1               5

<210> SEQ ID NO 39
<211> LENGTH: 17
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 39

Thr Ile Ser Thr Asp Xaa Ser Tyr Thr Tyr Tyr Pro Asp Ser Val Lys
1               5                   10                  15

Gly

<210> SEQ ID NO 40
<211> LENGTH: 50
<212> TYPE: PRT
<213> ORGANISM: Artificial
<220> FEATURE:
<223> OTHER INFORMATION: ANGPTL4 protein fragment

<400> SEQUENCE: 40
```

Gln Gly Arg Pro Ala Gln Pro Glu Pro Arg Phe Ala Ser Trp Asp
1               5                   10                  15

Glu Met Asn Leu Leu Ala His Gly Leu Leu Gln Leu Gly His Gly Leu
            20                  25                  30

Arg Glu His Val Glu Arg Thr Arg Gly Gln Leu Gly Ala Leu Glu Arg
        35                  40                  45

Arg Met
    50

<210> SEQ ID NO 41
<211> LENGTH: 50
<212> TYPE: PRT
<213> ORGANISM: Artificial
<220> FEATURE:
<223> OTHER INFORMATION: ANGPTL4 protein fragment

<400> SEQUENCE: 41

Leu Gln Leu Gly His Gly Leu Arg Glu His Val Glu Arg Thr Arg Gly
1               5                   10                  15

Gln Leu Gly Ala Leu Glu Arg Arg Met Ala Ala Cys Gly Asn Ala Cys
            20                  25                  30

Gln Gly Pro Lys Gly Lys Asp Ala Pro Phe Lys Asp Ser Glu Asp Arg
        35                  40                  45

Val Pro
    50

<210> SEQ ID NO 42
<211> LENGTH: 50
<212> TYPE: PRT
<213> ORGANISM: Artificial
<220> FEATURE:
<223> OTHER INFORMATION: ANGPTL4 protein fragment

<400> SEQUENCE: 42

Ala Ala Cys Gly Asn Ala Cys Gln Gly Pro Lys Gly Lys Asp Ala Pro
1               5                   10                  15

Phe Lys Asp Ser Glu Asp Arg Val Pro Glu Gly Gln Thr Pro Glu Thr
            20                  25                  30

Leu Gln Ser Leu Gln Thr Gln Leu Lys Ala Gln Asn Ser Lys Ile Gln
        35                  40                  45

Gln Leu
    50

<210> SEQ ID NO 43
<211> LENGTH: 53
<212> TYPE: PRT
<213> ORGANISM: Artificial
<220> FEATURE:
<223> OTHER INFORMATION: ANGPTL4 protein fragment

<400> SEQUENCE: 43

Glu Gly Gln Thr Pro Glu Thr Leu Gln Ser Leu Gln Thr Gln Leu Lys
1               5                   10                  15

Ala Gln Asn Ser Lys Ile Gln Gln Leu Phe Gln Lys Val Ala Gln Gln
            20                  25                  30

Gln Arg Tyr Leu Ser Lys Gln Asn Leu Arg Ile Gln Asn Leu Gln Ser
        35                  40                  45

Gln Ile Asp Leu Leu
    50

<210> SEQ ID NO 44

```
<211> LENGTH: 57
<212> TYPE: PRT
<213> ORGANISM: Artificial
<220> FEATURE:
<223> OTHER INFORMATION: ANGPTL4 protein fragment

<400> SEQUENCE: 44

Phe Gln Lys Val Ala Gln Gln Arg Tyr Leu Ser Lys Gln Asn Leu
1               5                   10                  15

Arg Ile Gln Asn Leu Gln Ser Gln Ile Asp Leu Leu Ala Pro Thr His
            20                  25                  30

Leu Asp Asn Gly Val Asp Lys Thr Ser Arg Gly Lys Arg Leu Pro Lys
        35                  40                  45

Met Thr Gln Leu Ile Gly Leu Thr Pro
    50                  55

<210> SEQ ID NO 45
<211> LENGTH: 25
<212> TYPE: PRT
<213> ORGANISM: Artificial
<220> FEATURE:
<223> OTHER INFORMATION: ANGPTL4 protein fragment

<400> SEQUENCE: 45

Leu Gln Leu Gly His Gly Leu Arg Glu His Val Glu Arg Thr Arg Gly
1               5                   10                  15

Gln Leu Gly Ala Leu Glu Arg Arg Met
            20                  25

<210> SEQ ID NO 46
<211> LENGTH: 25
<212> TYPE: PRT
<213> ORGANISM: Artificial
<220> FEATURE:
<223> OTHER INFORMATION: ANGPTL4 protein fragment

<400> SEQUENCE: 46

Ala Ala Cys Gly Asn Ala Cys Gln Gly Pro Lys Gly Lys Asp Ala Pro
1               5                   10                  15

Phe Lys Asp Ser Glu Asp Arg Val Pro
            20                  25

<210> SEQ ID NO 47
<211> LENGTH: 25
<212> TYPE: PRT
<213> ORGANISM: Artificial
<220> FEATURE:
<223> OTHER INFORMATION: ANGPTL4 protein fragment

<400> SEQUENCE: 47

Glu Gly Gln Thr Pro Glu Thr Leu Gln Ser Leu Gln Thr Gln Leu Lys
1               5                   10                  15

Ala Gln Asn Ser Lys Ile Gln Gln Leu
            20                  25

<210> SEQ ID NO 48
<211> LENGTH: 28
<212> TYPE: PRT
<213> ORGANISM: Artificial
<220> FEATURE:
<223> OTHER INFORMATION: ANGPTL4 protein fragment

<400> SEQUENCE: 48

Phe Gln Lys Val Ala Gln Gln Arg Tyr Leu Ser Lys Gln Asn Leu
1               5                   10                  15
```

Arg Ile Gln Asn Leu Gln Ser Gln Ile Asp Leu Leu
         20                  25

<210> SEQ ID NO 49
<211> LENGTH: 1313
<212> TYPE: DNA
<213> ORGANISM: Mus musculus

<400> SEQUENCE: 49
gttccggagt cctagcgttg ctgcacccaa ggccaccccc agaatcatgc gctgcgctcc     60
gacagcaggc gctgccctgg tgctatgcgc ggctactgcg gggcttttga gcgcgcaagg    120
gcgccctgca cagccagagc caccgcgctt tgcatcctgg gacgagatga acttgctggc    180
tcacgggctg ctacagctcg gcatgggct gcgcgaacac gtggagcgca cccgtgggca    240
gctgggcgcg ctggagcgcc gcatggctgc ctgtggtaac gcttgtcagg ggcccaaggg    300
aaaagatgca cccttcaaag actccgagga tagagtccct gaaggccaga ctcctgagac    360
tctgcagagt ttgcagactc agctcaaggc tcaaaacagc aagatccagc aattgttcca    420
gaaggtggcc cagcagcaga gatacctatc aaagcagaat ctgagaatac agaatcttca    480
gagccagata gacctcttgg cccccacgca cctagacaat ggagtagaca agacttcgag    540
gggaaagagg cttcccaaga tgacccagct cattggcttg actcccaacg ccacccactt    600
acacaggccg ccccgggact gccaggaact cttccaagaa ggggagaggc acagtggact    660
tttccagatc cagcctctgg ggtctccacc attttttggtc aactgtgaga tgacttcaga    720
tggaggctgg acagtgattc agagacgcct gaacggctct gtggacttca ccagtcctg    780
ggaagcctac aaggatggct tcggagatcc ccaaggcgag ttctggctgg gcctggaaaa    840
gatgcacagc atcacaggga accgaggaag ccaattggct gtgcagctcc aggactggga    900
tggcaatgcc aaattgctcc aatttcccat ccatttgggg ggtgaggaca cagcctacag    960
cctgcagctc actgagccca cggccaatga gctgggtgcc accaatgttt cccccaatgg   1020
cctttccctg cccttctcta cttgggacca gaccatgac ctccgtgggg accttaactg    1080
tgccaagagc ctctctggtg gctggtggtt tggtacctgt agccattcca atctcaatgg   1140
acaatacttc cactctatcc cacggcaacg gcaggagcgt aaaaagggta tcttctggaa   1200
aacatggaag ggccgctact atcctctgca ggctaccacc ctgctgatcc agcccatgga   1260
ggctacagca gcctcttagc ctcctcactg gagcctggtt ccaggctaag aag          1313

<210> SEQ ID NO 50
<211> LENGTH: 410
<212> TYPE: PRT
<213> ORGANISM: Mus musculus

<400> SEQUENCE: 50

Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45

Leu Gln Leu Gly His Gly Leu Arg Glu His Val Glu Arg Thr Arg Gly
    50                  55                  60

Gln Leu Gly Ala Leu Glu Arg Arg Met Ala Ala Cys Gly Asn Ala Cys
65                  70                  75                  80

Gln Gly Pro Lys Gly Lys Asp Ala Pro Phe Lys Asp Ser Glu Asp Arg

-continued

```
                        85                      90                      95
Val Pro Glu Gly Gln Thr Pro Glu Thr Leu Gln Ser Leu Gln Thr Gln
                100                     105                     110

Leu Lys Ala Gln Asn Ser Lys Ile Gln Gln Leu Phe Gln Lys Val Ala
                115                     120                     125

Gln Gln Gln Arg Tyr Leu Ser Lys Gln Asn Leu Arg Ile Gln Asn Leu
                130                     135                     140

Gln Ser Gln Ile Asp Leu Leu Ala Pro Thr His Leu Asp Asn Gly Val
145                     150                     155                     160

Asp Lys Thr Ser Arg Gly Lys Arg Leu Pro Lys Met Thr Gln Leu Ile
                165                     170                     175

Gly Leu Thr Pro Asn Ala Thr His Leu His Arg Pro Pro Arg Asp Cys
                180                     185                     190

Gln Glu Leu Phe Gln Glu Gly Glu Arg His Ser Gly Leu Phe Gln Ile
                195                     200                     205

Gln Pro Leu Gly Ser Pro Pro Phe Leu Val Asn Cys Glu Met Thr Ser
                210                     215                     220

Asp Gly Gly Trp Thr Val Ile Gln Arg Arg Leu Asn Gly Ser Val Asp
225                     230                     235                     240

Phe Asn Gln Ser Trp Glu Ala Tyr Lys Asp Gly Phe Gly Asp Pro Gln
                245                     250                     255

Gly Glu Phe Trp Leu Gly Leu Glu Lys Met His Ser Ile Thr Gly Asn
                260                     265                     270

Arg Gly Ser Gln Leu Ala Val Gln Leu Gln Asp Trp Asp Gly Asn Ala
                275                     280                     285

Lys Leu Leu Gln Phe Pro Ile His Leu Gly Gly Glu Asp Thr Ala Tyr
                290                     295                     300

Ser Leu Gln Leu Thr Glu Pro Thr Ala Asn Glu Leu Gly Ala Thr Asn
305                     310                     315                     320

Val Ser Pro Asn Gly Leu Ser Leu Pro Phe Ser Thr Trp Asp Gln Asp
                325                     330                     335

His Asp Leu Arg Gly Asp Leu Asn Cys Ala Lys Ser Leu Ser Gly Gly
                340                     345                     350

Trp Trp Phe Gly Thr Cys Ser His Ser Asn Leu Asn Gly Gln Tyr Phe
                355                     360                     365

His Ser Ile Pro Arg Gln Arg Gln Glu Arg Lys Lys Gly Ile Phe Trp
                370                     375                     380

Lys Thr Trp Lys Gly Arg Tyr Tyr Pro Leu Gln Ala Thr Thr Leu Leu
385                     390                     395                     400

Ile Gln Pro Met Glu Ala Thr Ala Ala Ser
                405                     410
```